(12) United States Patent
Kinsella et al.

(10) Patent No.: US 9,718,781 B2
(45) Date of Patent: *Aug. 1, 2017

(54) METHODS AND COMPOUNDS FOR TREATING PROLIFERATIVE DISORDERS AND VIRAL INFECTIONS

(71) Applicant: University College Dublin, National University of Ireland, Dublin, Dublin (IE)

(72) Inventors: B. Therese Kinsella, Blackrock (IE); Helen Reid, Dublin (IE)

(73) Assignee: UNIVERSITY COLLEGE DUBLIN, NATIONAL UNIVERSITY OF IRELAND, DUBLIN, Belfield (IE)

( * ) Notice: Subject to any disclaimer, the term of this patent is extended or adjusted under 35 U.S.C. 154(b) by 77 days.

This patent is subject to a terminal disclaimer.

(21) Appl. No.: 14/391,917

(22) PCT Filed: Apr. 17, 2013

(86) PCT No.: PCT/IB2013/001104
§ 371 (c)(1),
(2) Date: Oct. 10, 2014

(87) PCT Pub. No.: WO2013/156861
PCT Pub. Date: Oct. 24, 2013

(65) Prior Publication Data
US 2016/0102051 A1    Apr. 14, 2016

Related U.S. Application Data

(60) Provisional application No. 61/625,540, filed on Apr. 17, 2012, provisional application No. 61/625,537, filed on Apr. 17, 2012, provisional application No. 61/625,516, filed on Apr. 17, 2012.

(51) Int. Cl.
| | | |
|---|---|---|
| *A61K 31/18* | (2006.01) | |
| *C07D 213/71* | (2006.01) | |
| *C07D 231/12* | (2006.01) | |
| *C07D 261/08* | (2006.01) | |
| *C07D 307/42* | (2006.01) | |
| *C07D 213/34* | (2006.01) | |
| *C07D 277/34* | (2006.01) | |
| *C07D 295/192* | (2006.01) | |
| *C07D 263/48* | (2006.01) | |
| *C07D 305/08* | (2006.01) | |
| *C07D 205/04* | (2006.01) | |
| *C07D 213/85* | (2006.01) | |

(52) U.S. Cl.
CPC ............ *C07D 213/71* (2013.01); *A61K 31/18* (2013.01); *C07D 205/04* (2013.01); *C07D 213/34* (2013.01); *C07D 213/85* (2013.01); *C07D 231/12* (2013.01); *C07D 261/08* (2013.01); *C07D 263/48* (2013.01); *C07D 277/34* (2013.01); *C07D 295/192* (2013.01); *C07D 305/08* (2013.01); *C07D 307/42* (2013.01)

(58) Field of Classification Search
CPC .... A61K 31/215; A61K 31/18; C07C 311/58; C07C 311/59; C07D 205/04; C07D 231/12; C07D 307/42; C07D 213/34; C07D 213/71; C07D 295/192; C07D 263/48; C07D 305/08; C07D 213/85; C07D 277/34
USPC ....... 514/210.17, 237.5, 344, 346, 357, 369, 514/377, 378, 406, 461, 522, 542, 562, 514/593
See application file for complete search history.

(56) References Cited

U.S. PATENT DOCUMENTS

| | | |
|---|---|---|
| 3,556,764 A | 1/1971 | Hamm |
| 3,714,209 A | 1/1973 | Tung et al. |
| 4,166,452 A | 9/1979 | Generales, Jr. |
| 4,256,108 A | 3/1981 | Theeuwes |
| 4,265,874 A | 5/1981 | Bonsen et al. |
| 5,434,124 A | 7/1995 | Mayer et al. |
| 5,697,967 A | 12/1997 | Dinh et al. |
| 6,136,157 A | 10/2000 | Lindeberg et al. |
| 6,214,841 B1 | 4/2001 | Jackson et al. |
| 6,231,600 B1 * | 5/2001 | Zhong .................. A61L 29/085 427/2.24 |
| 6,352,552 B1 | 3/2002 | Levinson et al. |
| 6,583,307 B2 | 6/2003 | Nolan et al. |
| 6,796,998 B2 | 9/2004 | Schaldach et al. |
| 7,135,038 B1 | 11/2006 | Limon |
| 7,618,949 B2 | 11/2009 | Boyer et al. |
| 7,713,538 B2 | 5/2010 | Lewis et al. |
| 7,833,544 B2 | 11/2010 | Lewis et al. |

(Continued)

FOREIGN PATENT DOCUMENTS

| | | |
|---|---|---|
| WO | 00/42004 A1 | 7/2000 |
| WO | 2009/089098 A1 | 7/2009 |
| WO | 2011/057262 A2 | 5/2011 |

OTHER PUBLICATIONS

Born et al., 1963, The Aggregation of Blood Platelets, J. Physiol 168:178-95.

(Continued)

*Primary Examiner* — Sabiha N Qazi
(74) *Attorney, Agent, or Firm* — Brown Rudnick LLP; Thomas C. Meyers

(57) ABSTRACT

The invention generally relates to methods and compounds for treating proliferative disorders, viral infections, or both. In some embodiments, the invention provides an anticancer or antiviral compound including a substituted nitro phenoxy phenyl, a sulfonylurea, and an alkyl group. In some embodiments, the invention provides a method of treating a proliferative disorder or a viral infection including administering an anticancer or antiviral compound that binds to a thromboxane receptor, has preferential binding for either TPalpha (TPα) or TPbeta (TPβ) receptor subtype.

4 Claims, 26 Drawing Sheets

(56) References Cited

U.S. PATENT DOCUMENTS

| | | | |
|---|---|---|---|
| 7,947,302 | B2 | 5/2011 | Falotico et al. |
| 8,486,994 | B2 | 7/2013 | Alberts et al. |
| 8,710,252 | B2 | 4/2014 | Pace-Asciak et al. |
| 2003/0232877 | A1 | 12/2003 | Sikorski et al. |
| 2004/0213818 | A1 | 10/2004 | Kashiwabara et al. |
| 2005/0010279 | A1 | 1/2005 | Tenerz et al. |
| 2005/0015136 | A1 | 1/2005 | Ikeuchi et al. |
| 2005/0025705 | A1 | 2/2005 | Wang |
| 2005/0043788 | A1 | 2/2005 | Luo et al. |
| 2005/0152943 | A1* | 7/2005 | Hezi-Yamit ............ A61F 2/90 424/423 |
| 2006/0122143 | A1 | 6/2006 | Boyer et al. |
| 2007/0168015 | A1 | 7/2007 | Momma et al. |
| 2009/0062904 | A1 | 3/2009 | Furst |
| 2009/0311299 | A1 | 12/2009 | Falotico et al. |
| 2010/0023115 | A1 | 1/2010 | Robaina et al. |
| 2011/0099785 | A1 | 5/2011 | Pacetti |

OTHER PUBLICATIONS

Custodi et al., 2012, Fitting the complexity of GPCRs modulation into simple hypotheses of ligand design, Journal of Molecular Graphics and Modelling 38:70-81.
Hanson et al., 2005, In vitro and in vivo pharmacological characterization of BM-613 [N-n-pentyl-N-[2-(4-methylphenylamino)-5-nitrobenzenesulfonyl]urea, a novel dual thromboxane synthase inhibitor and thromboxane receptor antagonist, The Journal of Phramacology and Experimental Therapeutics 313(1):293-301.
Hanson et al., 2006, Synthesis and Pharmacological Evaluation of Novel Nitrobenzenic Thromboxane Modulators as Antiplatelet Agents Acting on Both the Alpha and Beta Isoforms of the Human Thromboxane Receptor, Journal of Medicinal Chemistry 49(12):3701-3709.
Hanson et al., 2007, Design, Synthesis, and SAR study of a Series of N-Alkyl-N'[2-(aryloxy)-5-nitrobenzenesulfonyl]ureas and-cyanoguanidine as Selective Antagonists of the TP[alpha] and TP[beta] Isoforms of the Human Thromboxane A2 Receptor, Journal of Medicinal Chemistry 50(16):3928-3936.
Hirata et al., 2011, Prostanoid receptors, Chemical Reviews 111:6209-6230.
International Search Report and Written Opinion mailed on Oct. 11, 2013, for International Patent Application No. PCT/IB2013/001104, filed Apr. 17, 2013 (17 pages).
International Search Report and Written Opinion mailed on May 9, 2014, for International Patent Application No. PCT/IB2013/001258, filed Apr. 17, 2013 (22 pages).
Jenkins et al., 2005, Bioluminescent human breast cancer cell lines that permit rapid and sensitive in vivo detection of mammary tumors and multiple metastases in immune deficient mice, Breast Cancer Res 7:444-454.
Kassack et al., 2002, Quantitative comparison of functional screening by measuring intracellular Ca2+ with radioligand binding at recombinant human dopamine receptors, AAPS Pharmsci 4(4):102-111.
Matsui et al., 2012, Thromboxane A2 receptor signaling facilitates tumor colonization through P-selectin-mediated interaction of tumor cells with platelets and endothelial cells, Cancer Science 103(4):700-707.
Ogletree et al., 1985, Pharmacological actions of SQ 29,548, a novel selective thromboxane antagonist, J. Pharmacol Exp Ther 234:435-441.
Rolin et al, 2001, Activity of a novel dual thromboxane A2receptor antagonist and thromboxane synthase inhibitor (BM-573) on platelet function and isolated smooth muscles, Prostaglandins, Leukotrienes, and Essential Fatty Acids 65(2):67-72.
Rolin et al, 2003, BM-573, a dual 1-5, thromboxane synthase inhibitor and 10-19, thromboxane receptor antagonist, prevents 22-30 pig myocardial infarction induced by coronary thrombosis, The Journal of Phramacology and Experimental Therapeutics 306(1):59-65.
Ruef et al., 2006, Coronary stent thrombosis related to aspirin resistance: What are the underlying mechanisms?, J Inter. Cardiol. 19:507-509.
Bambi-Nyanguile et al., 2013, Synthesis and pharmacological evaluation of 2-aryloxy/arylamino-5-cyanobenzenesulfonyl ureas as novel thromboxane A2 receptor antagonists, European Journal of Medicinal Chemistry 35:32-40.
Dogne et al., 2004, Pharmacological Characterization ofN-tert-Butyl-N -[2-(4 -methylphenylamino)-5-nitrobenzenesulfonyl]urea (BM-573), a; Novel Thromboxane A2Receptor Antagonist and Thromboxane; Synthase Inhibitor in a Rat Model of Arterial Thrombosis and; Its Effects on Bleeding Time, JPET 309(2):498-505.
Turner et al., 2011, Identification of an interaction between the TPalpha and TPbeta isoforms of the human thromboxane A2 receptor with protein kinase C-related kinase (PRK) 1: implications for prostate cancer.; ; J. Biol. Chem., 29;286(17):15440-57.
Ghuysen et al., 2005, Pharmacological profile and therapeutic potential of BM-573, a combined thromboxane; receptor antagonist and synthase inhibitor, Cardiovasc Drug Rev. 23(1):1-14.
Kolh et al., 2005, Effects of dobutamine on left ventriculoarterial coupling and mechanical efficiency in; acutely schemic pigs, J Cardiovasc Pharmacol. 45(2):144-52.
Rolin et al., 2004, Pharmacological evaluation of both enantiomers of (R,S)-BM-591 as thromboxane A2; receptor antagonists and thromboxane synthase inhibitors, Other Lipid Mediat. 74(1-4):75-86.
Cherdon et al., 2011, BM-573 inhibits the development of early atherosclerotic lesions in Apo E deficient mice by; clocking TP receptors and thromboxane synthase, Prostaglandins Other Lipid Mediat. 94:124-32.
Choi et al., 2011, New therapeutic approaches to combat arterial thrombosis: better drugs for old targets,; novel targets, and future prospects, Mol Interv. 11(2):111-23.
Bousser et al., 2011, The Prevention of cerebrovascular and cardiovascular events of ischemic origin with terutroban in patients with a history of ischemic stroke or transient ischemic attack (PERFORM) study: baseline characteristics of the population, PERFORM Study Investigators. Cerebrovasc Dis. 27(6):608-13.
Bousser et al., 2009, Rationale and design of a randomized, double-blind, parallel-group study of terutroban 30; mg/day versus aspirin 100 mg/day in stroke patients: the prevention of cerebrovascular and; cardiovascular events of schemic origin with terutroban in patients with a history of ischemic; stroke or transient ischemic attack (PERFORM) study, PERFORM Study Investigators. Cerebrovasc Dis. 27(5):509-18.
Fiessinger et al., 2010, Thromboxane Antagonism with terutroban in Peripheral Arterial Disease: the TAIPAD; study, TAIPAD investigators. J Thromb Haemost. 8(11):2369-76.
Bousser et al., 2011, Terutroban versus aspirin in patients with cerebral ischaemic events (PERFORM): a; randomised, double-blind, parallel-group trial, PERFORM Study Investigators. Lancet. 11;377(9782):2013-22. Epub May 25, 2011. Erratum in: Lancet. Jul. 30, 2011;378(9789):402.

* cited by examiner

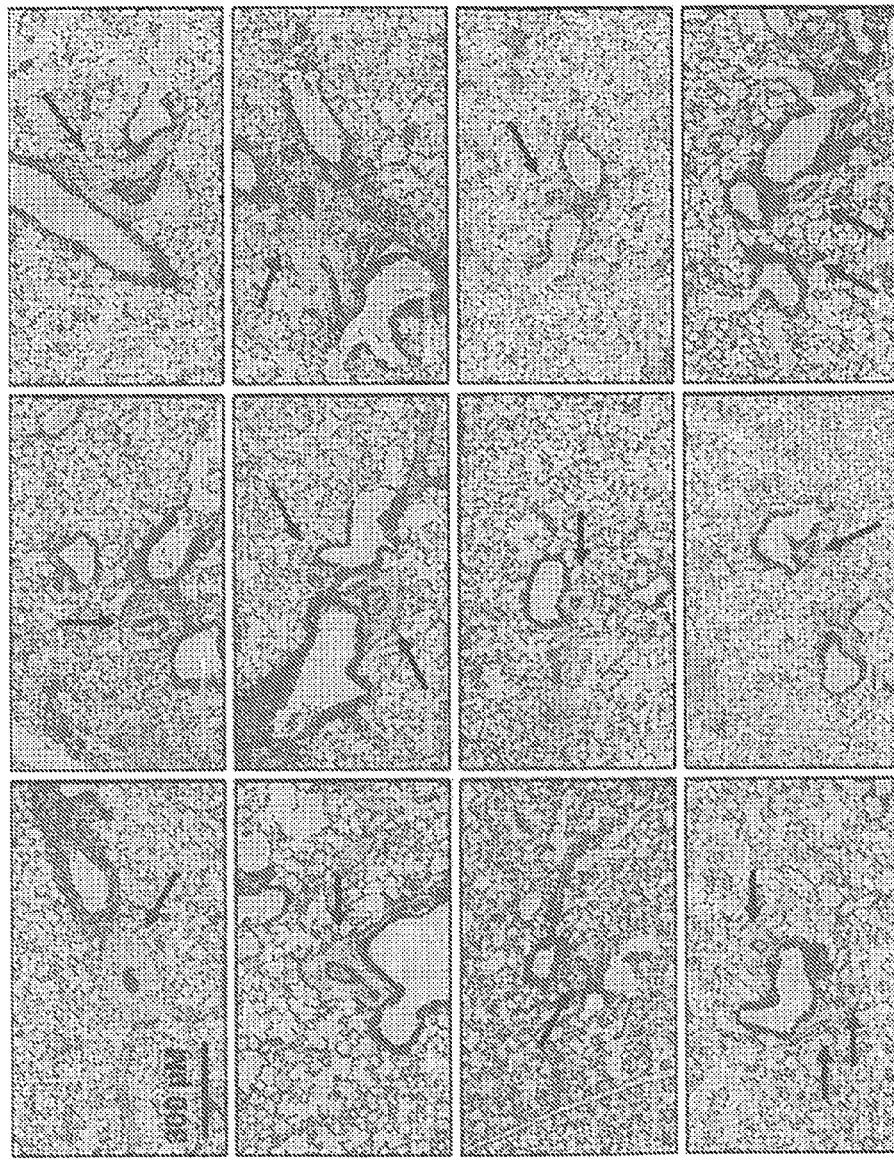

METHODS AND COMPOUNDS FOR TREATING PROLIFERATIVE DISORDERS AND VIRAL INFECTIONS

CROSS-REFERENCE TO RELATED APPLICATION

This application is a U.S. national stage entry of international patent application no. PCT/IB2013/001104, with international filing date Apr. 17, 2013, which application claims priority to, and the benefit of, U.S. Provisional Application No. 61/625,540, filed Apr. 17, 2012; U.S. Provisional Application No. 61/625,537, filed Apr. 17, 2012; and U.S. Provisional Application No. 61/625,516, filed Apr. 17, 2012, the contents of each of which are incorporated by reference herein in their entirety.

FIELD OF THE INVENTION

The invention generally relates to methods and compounds for treating proliferative disorders using TP antagonists.

BACKGROUND

Evidence suggests a role for the arachidonic acid-derived prostanoid thromboxane (TX) $A_2$ ($TXA_2$) in the cancer setting. For example, aspirin may play a role in the prevention of many common cancers, thought to be largely due to its ability to inhibit the increased generation of arachidonic acid-derived products (e.g., $TXA_2$) arising from the up-regulation of COX-1 and COX-2 in the cancer setting. Numerous clinical trials have been conducted to evaluate the benefits of aspirin or COX inhibitors in the treatment of a range of cancers.

While a number of COX-1/2 metabolites have been implicated in contributing to cancers, including prostaglandin (PG) D2 and PGE2, increased levels of $TXA_2$ and expression of $TXA_2$ synthase and of the $TXA_2$ receptor (the TP) may correlate with a range of cancers. $TXA_2$ has been implicated in several stages of tumor development and progression. This may be due to the ability of the TP to not only activate $G\alpha q$/phospholipase C, elevating intracellular calcium concentrations, but also due to its ability to activate the extracellular signal regulated kinase (ERK) cascades and to transactivate the epidermal growth factor receptor (EGFR), promoting cell proliferation and mitogenesis. Furthermore, the $TXA_2$ receptor is also known to robustly couple to $G\alpha 12$-mediated RhoA activation leading to changes in cell shape, motility and adhesion, processes implicated in cancer cell migration and metastasis.

Additionally, many viruses and other infectious agents, upon infecting a host including humans, cause an increase in prostanoids including thromboxane (TX) $A_2$ ($TXA_2$). This increase in prostanoids, including $TXA_2$, impairs the host's immune response and, thus, can help the infectious agent survive and propagate in the infected host. Such impairment of the host immune response can also facilitate infection by other infectious agents. Thus, initial infection by e.g., the influenza virus can, in turn, result in subsequent infection by and propagation of a second infectious agent (e.g., viral, bacterial, or fungal) thus expanding the underlying infectious disease status and lead to development of secondary diseases such as pneumonia.

Thus there is clinical interest in controlling levels of $TXA_2$.

Attempts to control levels of $TXA_2$ have involved targeting its synthesis. An enzyme called cyclooxygenase (COX) produces prostaglandin (PG) $H_2$ through its enzymatic conversion from the 20 carbon lipid arachidonic acid to generate a series of lipid mediators referred to as the prostanoids. In this synthetic pathway, the COX-derived $PGH_2$ endoperoxide product is converted by a host of specific PG synthases to make the prostaglandins $PGD_2$, $PGE_2$, $PGF_{2\alpha}$ and $PGI_2$ (Prostacyclin) and by TXA synthase to make $TXA_2$. The prostanoids are made in a cell- or tissue-specific manner and mediate a diverse range of physiologic roles in the body. By way of example, $TXA_2$ is predominantly made in platelets and in activated macrophages. Thus, inhibiting COX, such as within platelets or macrophage, should reduce or prevent the synthesis of $TXA_2$. COX inhibitors are associated with the irritation of gastric mucosa, peptic ulceration, and renal failure and may increase the risk of atherothrombosis and myocardial infarction, even with short-term use.

Given these problems with COX inhibitors, there is clinical interest in blocking the function of $TXA_2$ by blocking the $TXA_2$ receptor (the T prostanoid receptor, or in short the TP) at the platelet surface. A compound that binds to the TP antagonistically should inhibit $TXA_2$ binding and platelet aggregation and thus tumor development and progression. Furthermore, as the primary COX-1/COX-2 product $PGH_2$, an endoperoxide, also binds and activates the TP, antagonists of the TP should also impair its activation by $PGH_2$. Moreover, in addition to its enzymatic conversion into the prostanoids through the COX-1/COX-2 catalyzed reactions, arachidonic acid can also be converted non-enzymatically into the isoprostanes through free-radical mechanisms. Noteworthy, the isoprostane 8-iso-$PGF_{2\alpha}$ is the most abundant isoprostane generated during oxidative injury and actually mediates its actions/signals through the TP. Hence, selective TP antagonists will have the added advantage over COX-1/COX-2 inhibitors, such as aspirin or coxibs, in that they will also inhibit the adverse actions of the isoprostane 8-iso-$PGF_{2\alpha}$ generated during oxidative injury and of the endoperoxide $PGH_2$, in addition to inhibiting the action of $TXA_2$ itself. Unfortunately, existing TP antagonists have proven problematic. For example, they lack efficacy, TP specificity and target other receptors, such as the $PGD_2$, platelet activating factor 4, or Leukotriene $D_4$ receptors.

In humans and primates, but not in other species, $TXA_2$ actually signals through two distinct TP receptor isoforms referred to as $TP\alpha$ and $TP\beta$ which are encoded by the same gene and differ exclusively in their distal carboxy-terminal primary amino acid sequences. Furthermore, the current TP antagonists do not discriminate between the two $TP\alpha$ and $TP\beta$ receptor isoforms which play similar, but not identical, roles. $TP\alpha$, for example, is subject to desensitization in ways that $TP\beta$ is not and vice versa. Due to their distinct roles, in addition to developing general TP antagonists, there may also be clinical interest in compounds that can selectively interact with one or both isoforms of the TP.

SUMMARY

The invention generally provides compounds for use as anti-cancer drugs as well as antiviral agents and compounds. Compounds of the invention bind to thromboxane (TX) $A_2$ receptors (TP) and prevent $TXA_2$, and other incidental ligands including the endoperoxide $PGH_2$ and the isoprostane 8-iso-$PGF_{2\alpha}$ from binding to the TP and stimulating platelet activation and aggregation or binding and activating the $TP\alpha$ and/or $TP\beta$ isoforms. These compounds provide beneficial anticancer properties and other beneficial effects.

Compounds of the invention may also have applications as prophylaxis or as therapeutic treatment of various viral infections.

In certain embodiments, compounds of the invention prevent metastasis, for example, of human breast cancer cells, and prevents tumor burden development through novel mechanisms and by preventing some of the downstream signaling pathways activated by the TP isoforms through the use of compounds that selectively bind to either the TPα and/or TPβ form of the TXA$_2$ receptor (the TP). Compounds of the invention provide inhibitors or antagonists of TPα and/or TPβ isoforms and/or antagonists/inhibitors of select signaling pathways that are activated following TP activation and may have applications in a range of various cancers including prostate and breast cancers as demonstrated in a preclinical cancer disease model. In certain embodiments, activation of TPα/TPβ regulates various downstream signaling pathways and the TPs can activate and signal through RhoA and/or through PRK1 or AAMP. TP-regulation of such signaling may be important in the development, promotion and/or maintenance of various cell signaling pathways and events that promote and maintain cancer development, including endothelial cell migration, angiogenesis, or restenosis.

In some embodiments, compounds of the invention prevent breast cancer metastasis and breast cancer nodule formation and tumor formation in the lungs (and in all other organs). Only a very few administrations of a compound (e.g., 1, 2, 3, 5, etc.) of the invention may be necessary to prevent metastasis. TPα/TPβ also present novel biomarkers for use in personalized medicine in designing cancer-treatment regiments.

In some embodiments, compounds of the invention prevent dampening of the immune system which is mediated by elevated levels of TXA$_2$. Efficient immune activation is important in retarding cancer development and tumor cell eradication. Compounds of the invention will function synergistically with immune-modulating drugs and with oncolytic viruses in retarding and eradicating tumor cells.

In certain aspects, the invention provides an anticancer agent including a compound, or a pharmaceutically acceptable salt thereof, which includes a substituted nitro-phenoxy phenyl, a sulfonylurea, and an alkyl group. In some embodiments, the alkyl group is either an isopropyl group, a pentyl group, a tert-butyl group, or a cyclohexyl group.

In certain embodiments, the compound is represented by formula (I):

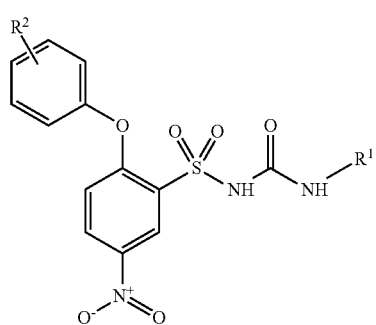

(I)

in which R$^1$ is an alkyl group and R$^2$ is either a halogen, an alkyl group, or an aryl group.

The invention further provides compounds of formula (I), in which R$^1$ is an isopropyl group, a pentyl group, a tert-butyl group, and a cyclohexyl group and R$^2$ is one of:

I,

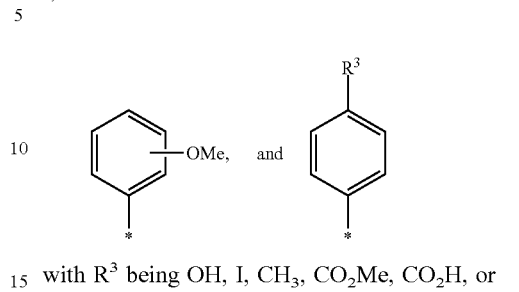

with R$^3$ being OH, I, CH$_3$, CO$_2$Me, CO$_2$H, or

[structure with CH$_3$]

As used herein, * represents the point of attachment.

In certain embodiments, the compound is represented by one of the formulas (II), (III), (IV), (V), (VI), (VII), (VIII), (IX), (X), and (XI):

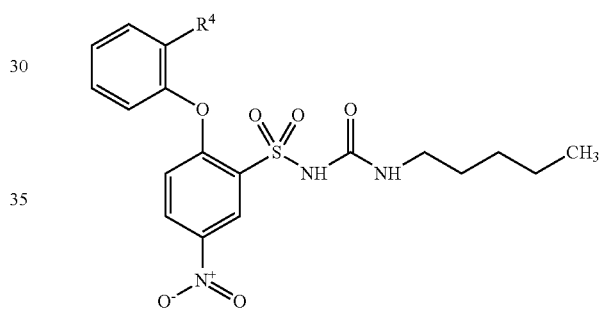

(II)

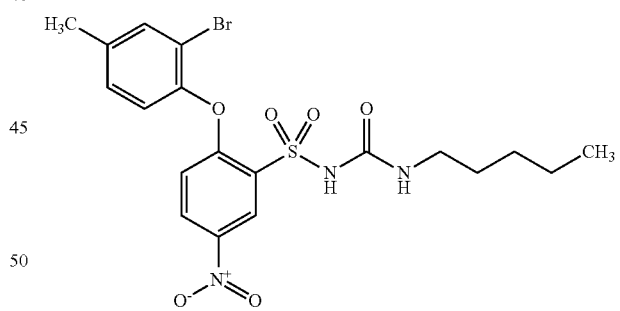

(III)

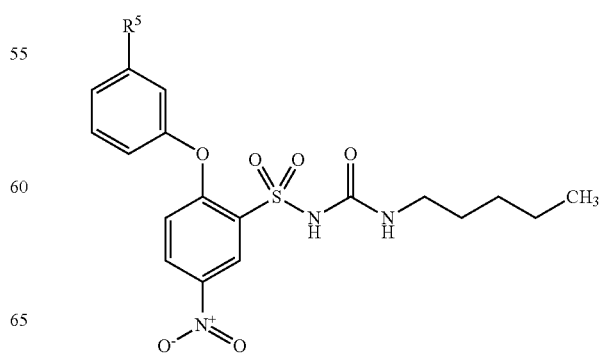

(IV)

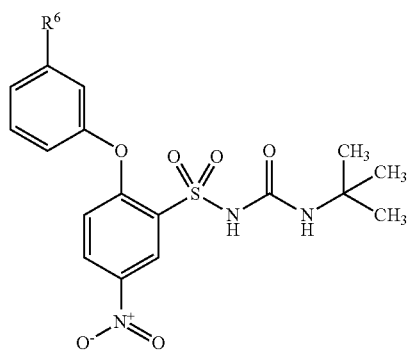
(V)
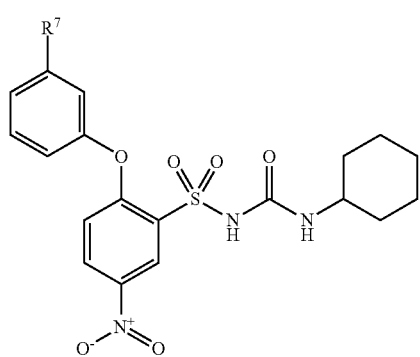
(VI)
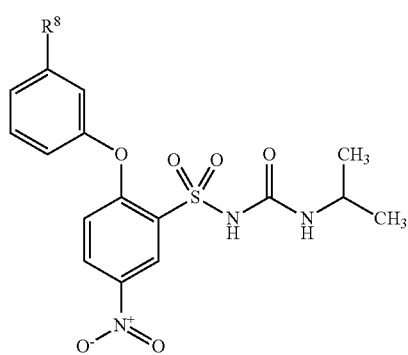
(VII)
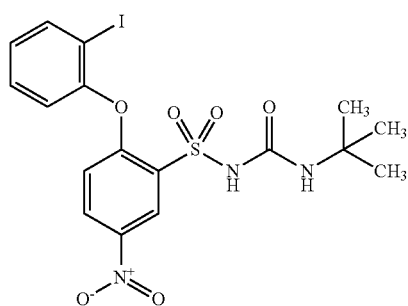
(VIII)
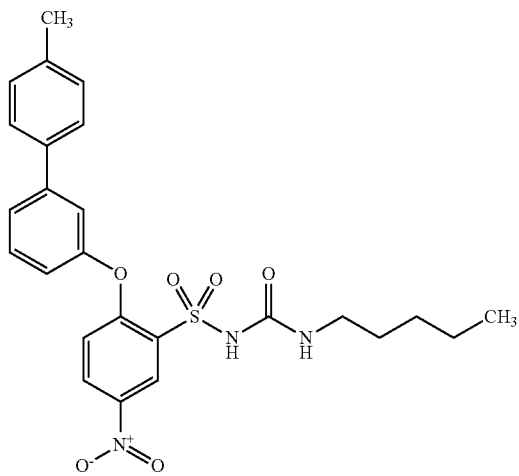
(IX)
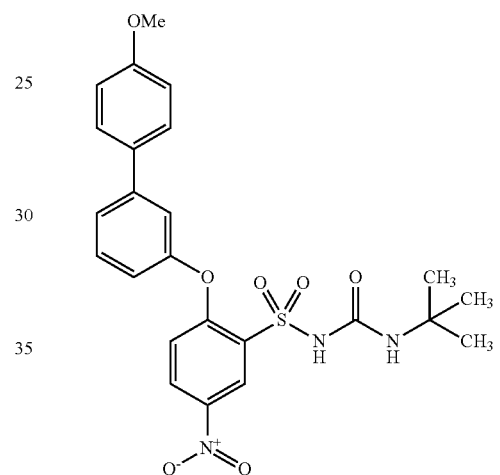
(X)
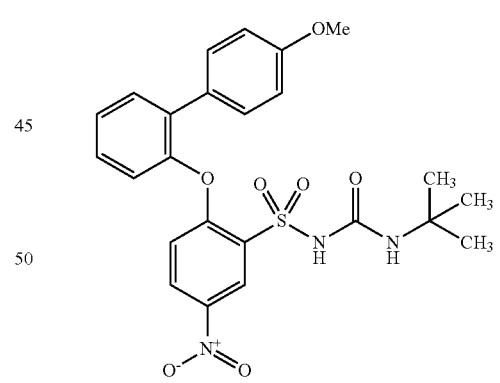
(XI)
In which R⁴ is
I,
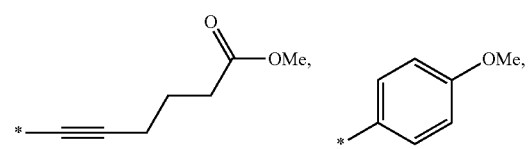

-continued
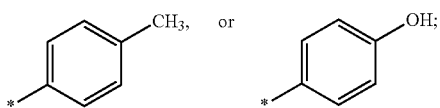
$R^5$ is one of
I and
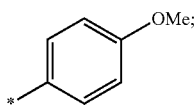 [SMILES: *c1ccc(OC)cc1]
$R^6$ is
I,
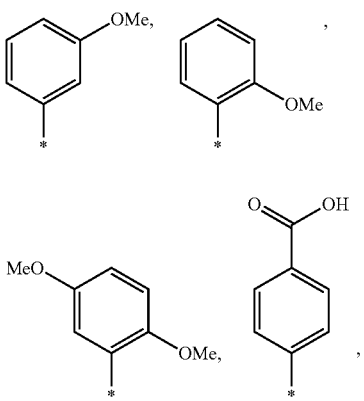
$R^7$ is
I,
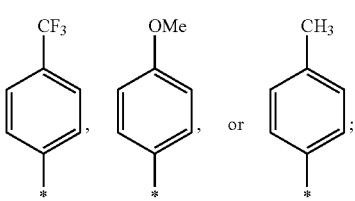
$R^8$ is
I,
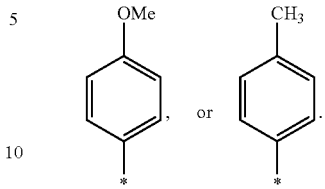
In certain embodiments the compound is represented by formula (XII):
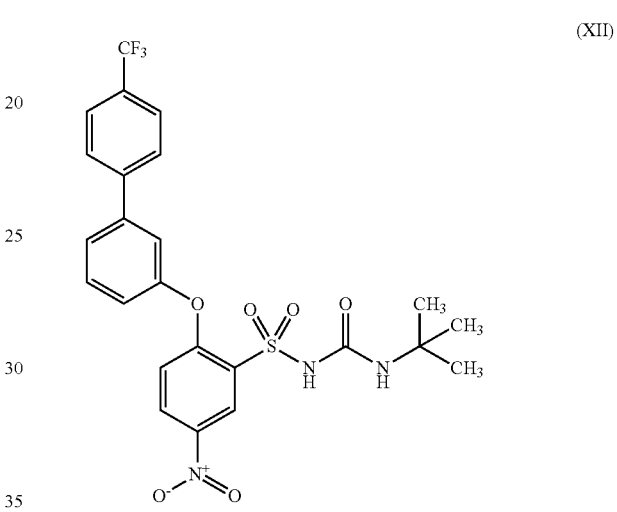
(XII)
In certain embodiments the compound is represented by formula (XIII):
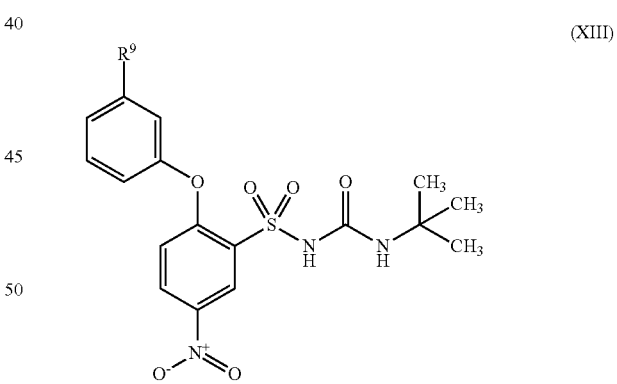
(XIII)
in which $R^9$ is
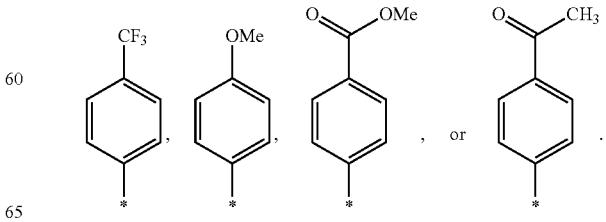
or a pharmaceutically acceptable salt thereof.

In certain embodiments, the anticancer compound is represented by one of the formulas (XIV), (XV), (XVI), (XVII), (XVIII), (XIX), (XX), and (XXI):
(XIV)
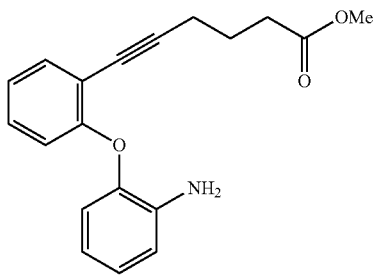
(XV)
(XVI)
(XVII)
(XVIII)
(XIX)
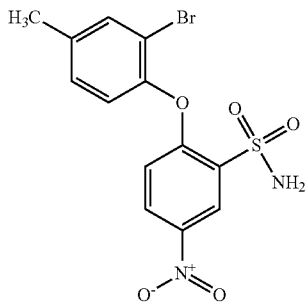
(XX)
(XXI)
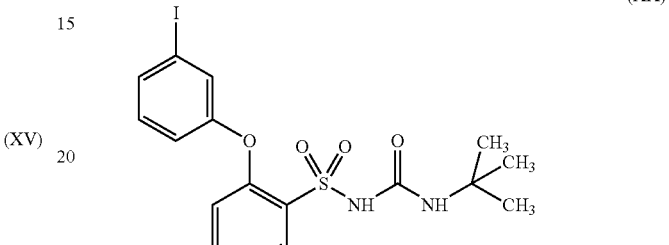
In certain embodiments, the compound is represented by formula (XXII):
(XXII)
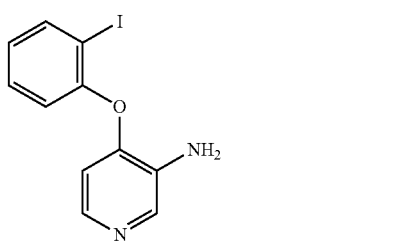
in which $R^{10}$ is
H, $NH_2$, I,
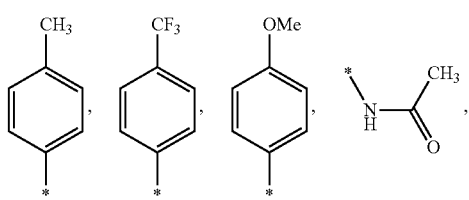
and $CO_2Me$.

In certain embodiments, the TP antagonist is represented by formula (XXII):
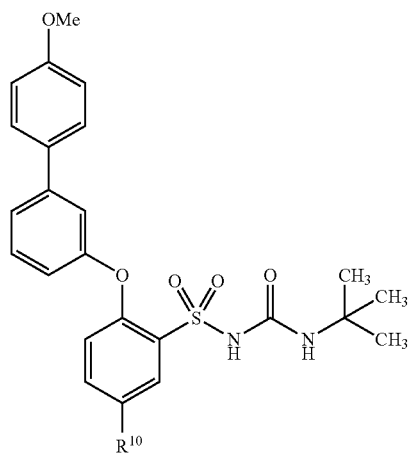
(XXII)
wherein $R^{10}$ is selected from the group consisting of,
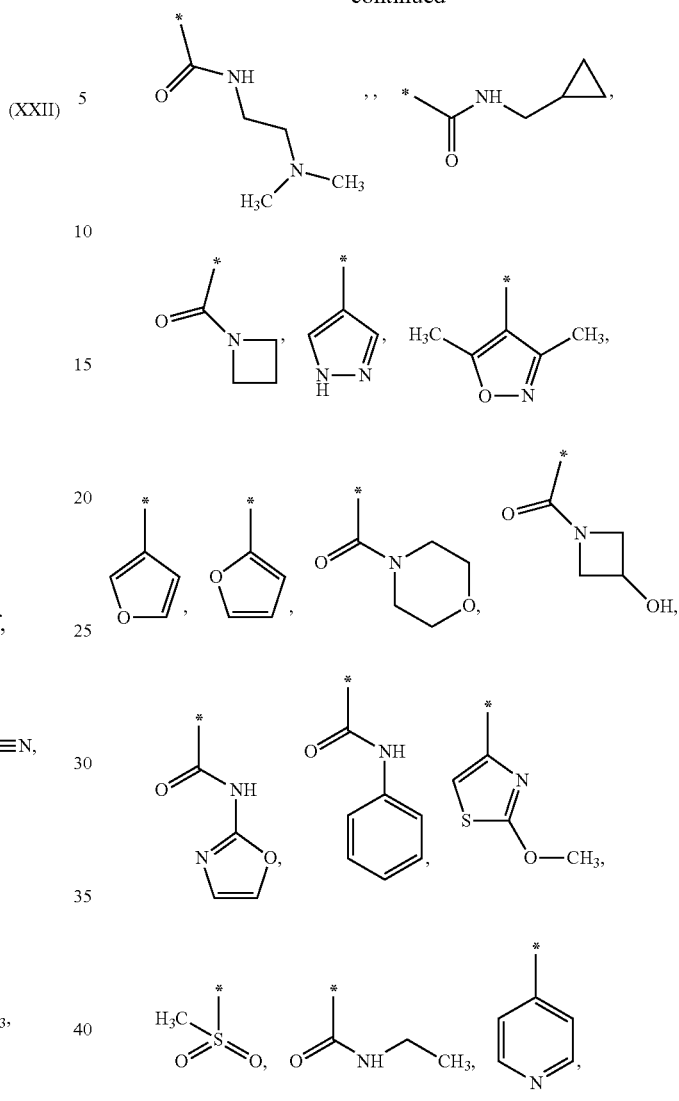
and Cl, or a pharmaceutically acceptable salt thereof.
In certain embodiments, the TP antagonist is represented by one of (LVII), (LVIII), (LIX), and (LX):
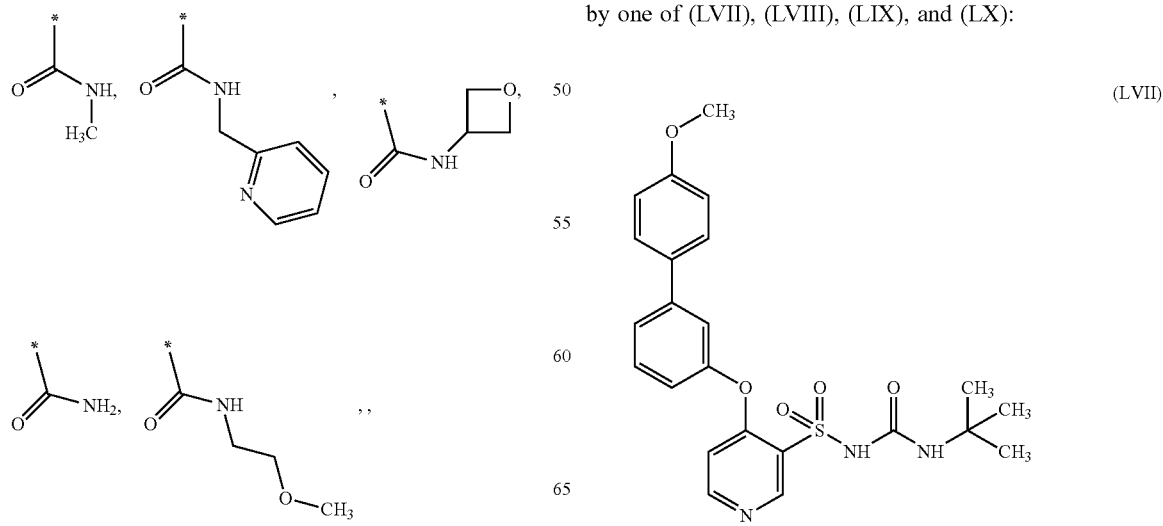
(LVII)

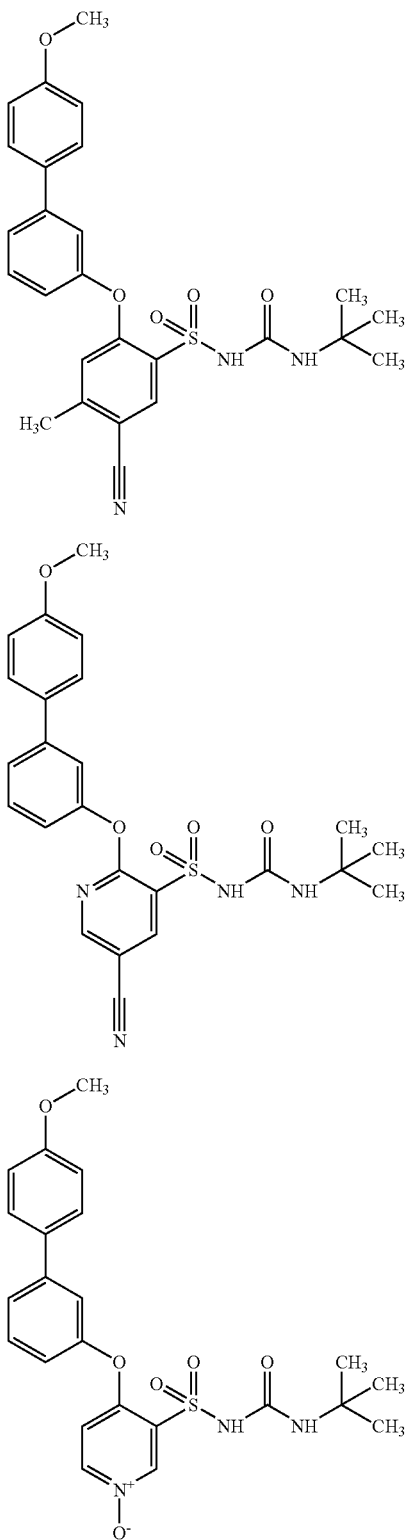

(LVIII)

(LIX)

(LX)

or a pharmaceutically acceptable salt thereof.

In certain aspects, the invention provides a method of treating cancer that involves administering an effective dose of an anticancer agent including a compound, or a pharmaceutically acceptable salt thereof, that specifically binds to a TP and preferably does not specifically bind to non-thromboxane receptors. In some embodiments, the compound exhibits preferential binding for either TPα and/or TPβ receptor subtype. Any oncology treatment use or application may be covered by methods and compounds of the invention.

Methods of the invention include treatment of a proliferative disorder such as cancer, including colorectal, non-Hodgkin's lymphoma, prostate, ovary, breast, pancreatic, bladder, lung (non-small cell lung), colon, and ovarian cancer. In certain embodiments, the invention provides methods for treating stomach, rectal, lung, cervix uteri, corpus uteri, testis, renal, brain/CNS, head and neck, throat, Hodgkin's disease, multiple myeloma, leukemia, melanoma, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney cancer or lymphoma cancer.

In certain aspects, the invention provides for the use of a compound to treat a proliferative disorder. The compound can be any of the compounds disclosed herein. In some embodiments, the proliferative disorder is a cancer, including colorectal, non-Hodgkin's lymphoma, prostate, ovary, breast, pancreatic, bladder, lung (non-small cell lung), colon, and ovarian cancer. In certain embodiments, the invention provides use of compounds to treat stomach, rectal, lung, cervix uteri, corpus uteri, testis, renal, brain/CNS, head and neck, throat, Hodgkin's disease, multiple myeloma, leukemia, melanoma, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney cancer or lymphoma cancer.

In certain aspects, the invention provides pro-drugs and their uses. Pro-drugs of the invention are activated to an active form at tumor sites. Methods of the invention include administering an anticancer compound of the invention as a pro-drug. In some embodiments, the anticancer compound will function synergistically with other drugs in treating cancer.

In certain embodiments, compounds of the invention antagonize the human TP and prevent various cell signaling pathways which are regulated by TP signaling. Thus, compounds of the invention prevents the dampening or impairment of the host human immune response which are driven by elevations in the circulatory levels of TXA2 and can thus function as an adjuvant therapy or co-administered therapy in the poly-pharmacy treatment of influenza infections, of general viral infection, and of general infectious agent infections. Antagonizing the human TP reduces clinical scores (e.g., in a similar manner to Tamiflu), reduces lung consolidation, reduces viral titres, reduces the general severity of infection, and reduces clinical disease scores.

In certain embodiments, compounds of the invention are selective for the TP and do not inhibit TXA2 synthase or other prostanoid receptors. In certain embodiments, the antitussive properties of the inventive compounds, as TP antagonists, reduce viral spread or transfer from host to host in the general population.

By antagonizing TP signaling, compounds of the invention prevent signaling by the elevated levels of TXA2 found in the infected hosts. This prevents or reduces the impairment of the host immune response which arise due to elevated levels of TXA2 and prostanoids, Further, this prevents or reduces the impairment of the host immune response which arise due to elevated levels of non-enzymatically derived prostanoids such as 8-epi-PGH2α following viral infections, By antagonizing TP signaling, the inventive compounds prevent or reduce nucleation of platelets with infecting viral particles which give rise to complexes which shield infecting viral particles from the host immune system, as well as destabilize pre-formed nucleated complexes of platelets with infecting viral particles which give rise to complexes which shield infecting viral particles from the host immune system.

Compounds of the invention do not give rise to viral resistance. Treatment with antiviral compounds disclosed herein can prevent other secondary infections and thus has prophylactic and therapeutic treatment properties in preventing or treating secondary infections and diseases such as pneumonia. The antitussive properties of these compounds further add to their antiviral and anti-influenza properties.

The invention generally provides broad spectrum antiviral agents with both prophylactic and therapeutic treatment properties. Antiviral compounds of the invention can be used for short-term treatment and well as for treatment of various cardiovascular (CV), renal and pulmonary diseases, various cancers, drug coating on bare metal stents, other stents and balloons and uses as an adjuvant therapy in the treatment of Alzheimer's disease.

In certain aspects, the invention provides an antiviral agent including a compound, or a pharmaceutically acceptable salt thereof, which includes a substituted nitro-phenoxy phenyl, a sulfonylurea, and an alkyl group. In some embodiments, the alkyl group is either an isopropyl group, a pentyl group, a tert-butyl group, or a cyclohexyl group.

BRIEF DESCRIPTION OF THE DRAWINGS

FIG. 18 shows the effect of TP20 on Perivascular Edema in Influenza A/Puerto Rico/8/1934 H1N1 Infected Mice.

DETAILED DESCRIPTION

Figure 1A:
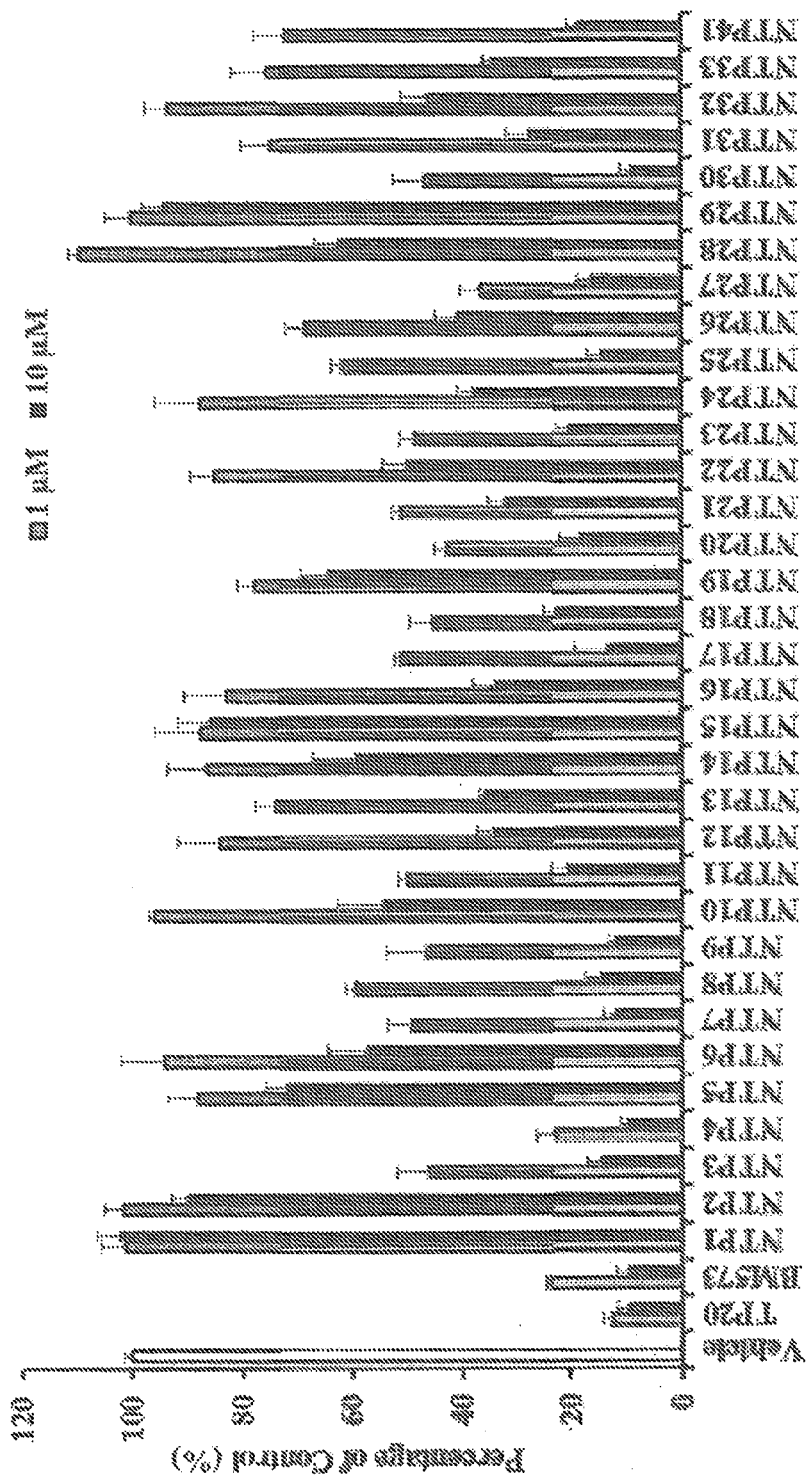
FIGS. 1A and 1B show the effect of the TP antagonist compounds of the invention on U46619-mediated calcium mobilization in HEK.TPα and HEK.TPβ cells

The invention generally relates to anticancer compounds that bind antagonistically with TP to prevent the binding of $TXA_2$, $PGH_2$ and/or isoprostanes including 8-iso-$PGF_{2\alpha}$. Compounds of the invention include those that exhibit preferential binding for either TPα and/or TPβ receptor subtype. As discussed herein, the invention provides small molecule anticancer compounds, which exhibit attractive ADME (absorption, distribution, metabolism, and excretion) properties and which may inhibit platelet aggregation. The invention further provides exemplary synthetic routes for anticancer compounds by way of example but not exhaustive of all routes of synthesis. Exemplary compounds of the invention are disclosed.

In some embodiments, compounds of the invention display significant TP selectivity and antagonistic activity ex vivo in human platelets and are effective in preventing in vivo thrombosis in rodents using the ferric chloride model, as discussed, for example, in U.S. Pub. 2005/0025705, herein incorporated by reference in its entirety.

Compounds of the invention preferably inhibit $TXA_2$-induced platelet aggregation at a half-maximal inhibitory concentration ($IC_{50}$) below 100 nM. Compounds of the invention preferably inhibit $TXA_2$-induced platelet aggregation at a half-maximal inhibitory concentration ($IC_{50}$) below 50 nM. Compounds of the invention preferably inhibit $TXA_2$-induced platelet aggregation at a half-maximal inhibitory concentration ($IC_{50}$) below 20 nM. Compounds of the invention preferably inhibit $TXA_2$-induced platelet aggregation at a half-maximal inhibitory concentration ($IC_{50}$) below 5 nM. In certain embodiments, compounds of the invention further inhibit $TXA_2$-induced platelet aggregation but not aggregation induced by other platelet agonists such as, for example, thrombin or adenosine diphosphate (ADP). Further, compounds of the invention preferably do not agonize or antagonize signaling by several other G-protein coupled receptors, kinases, phosphatases, or ion channels including human Ether-á-go-go related gene (hERG).

Compounds of the invention exhibit attractive ADME properties. In some embodiments, compounds have a half-life of 20 minutes and more than 200 minutes in rat hepatic microsomes and plasma, respectively. Inventive compounds have greater than 50% oral bioavailability and a 4.5 hour elimination half-life for oral delivery. In some embodiments, inventive compounds exhibit 1.4 ml/min/kg clearance rates following I.V. delivery and are neither cytotyoxic or genotoxic. Anticancer compounds of the invention exhibit the ability to inhibit agonist-induced intracellular calcium mobilization and inhibit platelet aggregation in ex vivo assays. In some embodiments, compounds of the invention show no effect on signaling through other prostanoid (prostaglandin (PG) $I_2$ receptor, IP; $PGE_2$ receptors $EP_3$ and $EP_1$; $PGF_{2\alpha}$ receptor, FP) and non-prostanoid receptors including the purinergic (ADP) and thrombin (PAR1) receptors, also involved in platelet activation similar to the TP isoforms. Further, compounds exhibit minimal toxicity and favorable cell permeability.

Shown below are exemplary methods of synthesis of compounds of the invention.

First, 2-Chloro-5-nitrobenzenesulfonamide is synthesized according to Pathway A.

PATHWAY A

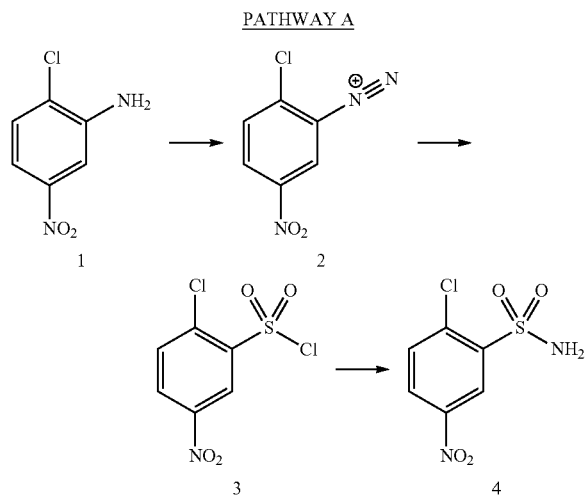

Sodium nitrite (4.96 g; 72 mmol) dissolved in water (11 mL) was added drop wise over 30 minutes to a cooled solution (−5° C.) of 2-chloro-5-nitroaniline (1; 10.00 g; 58 mmol) in 12M HCl (104 mL). While stirring at −5° C. for a further 30 minutes, a solution of copper(II) chloride dissolved in water (4 mL) was poured into acetic acid (110 mL) previously saturated with sulphur dioxide (gas). This was then added to the diazonium salt 2 solution and stirred until nitrogen gas ceased to evolve. The reaction mixture was quenched with ice-water and the subsequent precipitate formed was collected by filtration and washed with cold water. Aqueous ammonium hydroxide (35%) (120 mL) was added to the resulting sulfonyl chloride 3 and stirred for 18 hours. The solution was then filtered and the resulting filtrate was acidified using 12M HCl to precipitate the title compound 4 (7.55 g; 55% over 3 steps). M.p 186-187° C. (lit. 177-179° C.)

From this point, Pathway B was used for the synthesis of 2-(3-Iodophenoxy)-5-nitrobenzenesulfonamide 6.

PATHWAY B

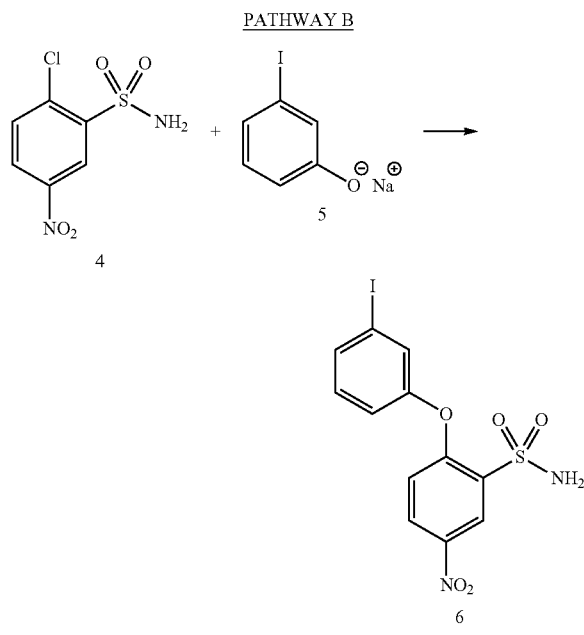

An aqueous solution of NaOH (3.66 g; 92 mmol; 10% w/v) was added to a solution of 3-iodophenol (18.30 g; 83 mmol) in acetone (130 mL). Evaporation under reduced pressure afforded the crystals of the sodium salt 5, which were added to a solution of sulfonamide 4 (3.94 g; 17 mmol) in acetonitrile (24 mL). The mixture was refluxed and potassium carbonate (1.62 g; 12 mmol) was added. After completion of the reaction (48 h, monitored by TLC), the solution was acidified using 12M HCl, diluted with water and extracted with ethyl acetate (×3). The combined organics were dried (MgSO$_4$), and concentrated in vacuo. The crude product was purified using column chromatography (SiO$_2$; pentane/ethyl acetate, 3:1), yielding the title compound 6 as a colorless solid (5.84 g; 84%). M.p. 153-155° C. (lit. 153-154° C.).

From this point, 2-(3-Iodophenoxy)-5-nitrobenzene(t-butyl)sulfonyl urea (Formula XXXVIII) was prepared according to Pathway C.

PATHWAY C

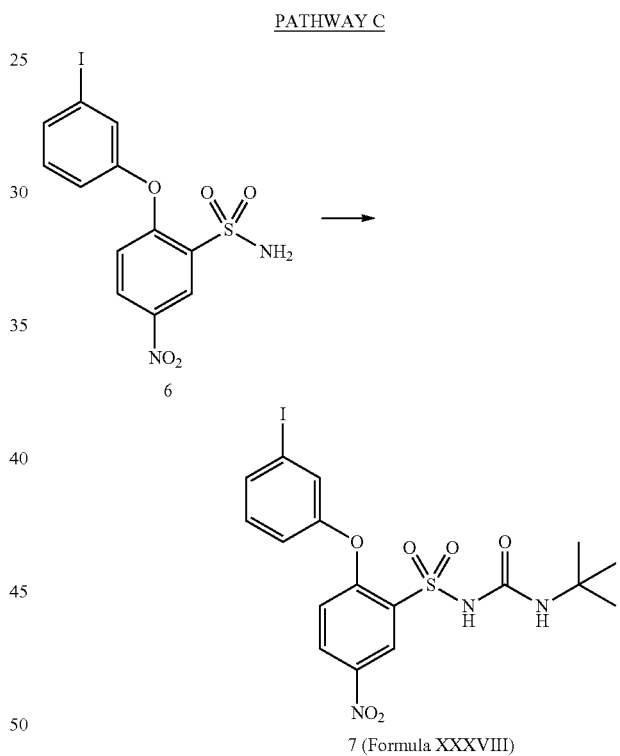

NaOH (122 mg; 3.04 mmol) dissolved in water (10% w/v) was added to a solution of sulfonamide 6 (1279 mg; 3.04 mmol) in acetone (10 mL). The mixture was stirred for 10 minutes, then the solvent was evaporated in vacuo. The resulting sodium salt was resuspended in acetone (10 mL) and gently put under reflux, then t-butyl isocyante was added to the mixture (603 mg; 700 μL; 6.08 mmol). After 40 minutes the reaction mixture was concentrated under reduced pressure and the resulting solid was washed with ethyl acetate, isolated by filtration and dissolved in an aqueous solution of 0.5M NaOH. The subsequent solution that formed was acidified to pH 1 with 12 M HCl, and the precipitate that formed was collected by filtration. This delivered the title compound 7 (Formula XXXVIII) with no further purification necessary (1484 mg; 94%). M.p. 233-236° C. (lit. 154-157° C.).

Compound 8 (Formula XLI) and/or compound 9 (Formula X) are obtained via pathway D.

PATHWAY D

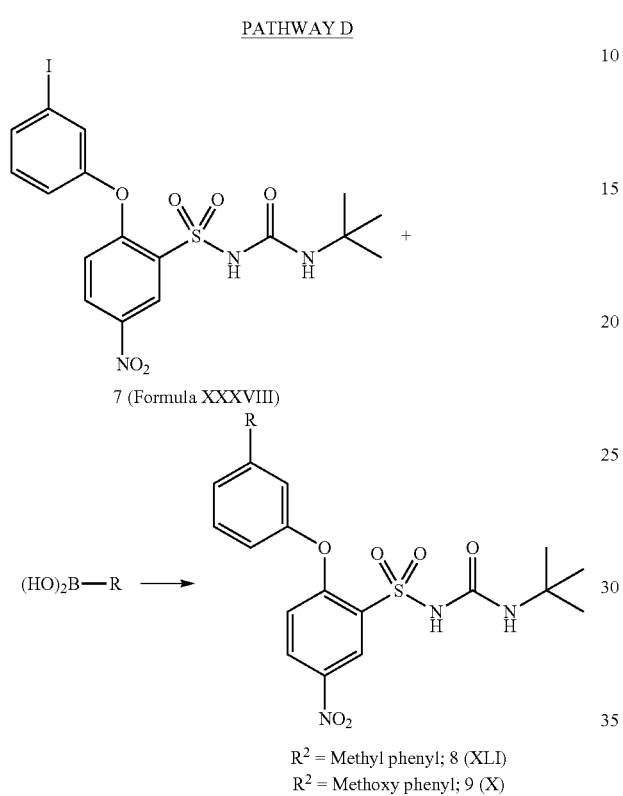

7 (Formula XXXVIII)

R² = Methyl phenyl; 8 (XLI)
R² = Methoxy phenyl; 9 (X)

An aqueous degassed solution of potassium carbonate (4 mmol in 3.1 mL H₂O) was added to a schlenk tube containing aryl iodide 7 (1 mmol; Formula XXXVIII), the appropriate boronic acid (1.1 mmol), palladium(II) acetate (0.08 mmol) in DMF (3.1 mL) under nitrogen. The reaction mixture was degassed and refilled with nitrogen 3 times, and then stirred at room temperature for 24 hours. Upon completion of the reaction, the mixture was diluted with water and extracted with ethyl acetate (×3), dried over MgSO₄ and concentrated in vacuo. The crude product was purified using flash chromatography (8; SiO₂; pentane/diethyl ether, 1:1) (9; SiO₂; pentane/diethyl ether, 1:2), isolating the title compounds (8; 63% (Formula XLI); 9; 58% (Formula X)). M.p. (8 210-212° C.; 9 194-197° C.).

Further description of preparation of sulfonylurea derivatives is given in U.S. Pat. No. 5,434,124, incorporated by reference in its entirety. The preparation of p-nitrobenzenesulfonylurea from p-nitrobenzenesulfonamide, through a p-nitrobenzenesulfonylisourea intermediate, is described in U.S. Pat. Nos. 3,556,764 and 3,714,209, incorporated by reference herein in their entirety.

Through suitable variations of the pathways discussed herein, a variety of substituted nitrobenzenesulfonylureas of formula (I) can be prepared:

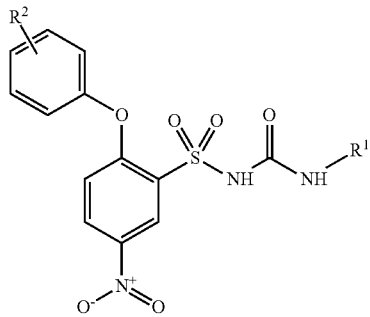

In certain embodiments, N-(tert-butylcarbamoyl)-2-(3-methoxyphenoxy)-5-nitrobenzenesulfonamide (also known as CAY10535) is obtained. CAY10535 has formula (XXIII):

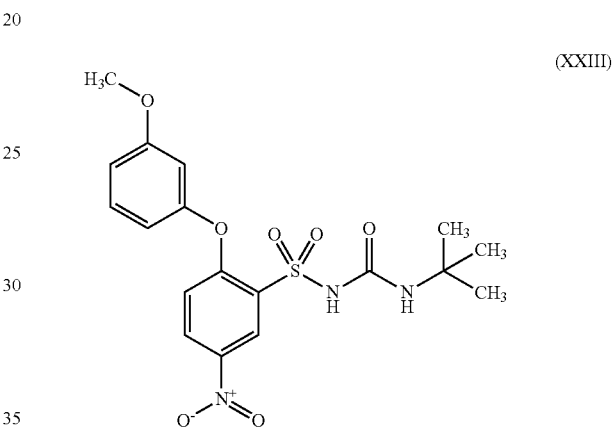

CAY10535 is available from Cayman Chemical (Ann Arbor, Mich.), and has a molecular formula of $C_{18}H_{21}N_3O_7S$ and formula weight 423.4. CAY10535 can be obtained as a crystalline solid. A stock solution is made by dissolving the compound in DMSO or ethanol with an inert gas. For solution in a aqueous buffer, CAY10535 is first dissolved in DMF and then diluted in a desired aqueous buffer.

In certain embodiments, the palladium-catalyzed Suzuki reaction is further used to add one or more aryl groups, optionally containing one or more substituents, to the above-described compounds. For example, where $R^2$ represents a para methyl group of a 4-methylphenol substituent on the oxygen bridge, that $R^2$ group can be replaced with an aryl group, including, for example, 4-methylphenyl or any other. Use of the palladium-catalyzed Suzuki reaction is described in U.S. Pat. No. 6,583,307 and U.S. Pat. No. 6,136,157, both of which are herein incorporated by reference in their entirety.

In certain embodiments, compounds of the invention, for example as synthesized according to combinations of the above-described pathways, are described by formulas (XXIV), (XXV), (XXVI), (XXVII), (III), (XXVIII), (VIII), (XXIX), (XXX), (XXXI), (XXXII), (XXXIII), (XXXIV), (XXXV), (XXXVI), (XXXVII), (XXXVIII), (XXXIX), (IX), (XL), (XLI), (XLII), (XLIII), (XLIV), (X), (XLV), (XLVI), (XII), (XLVII), and (XI).

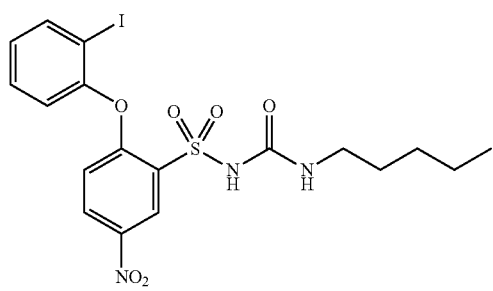
(XXIV)
Mw - 533.34
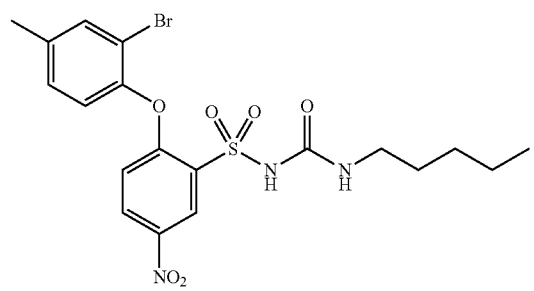
(III)
Mw - 500.36
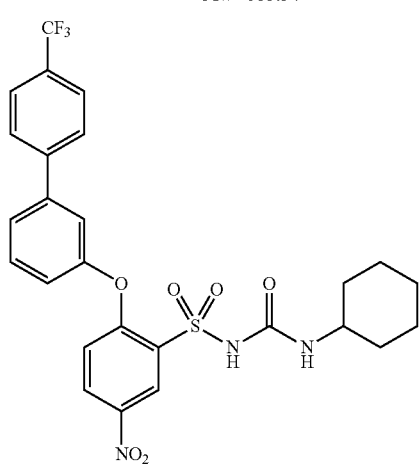
(XXV)
Mw - 563.55
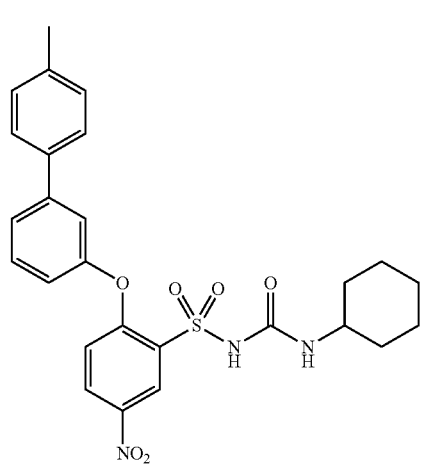
(XXVIII)
Mw - 509.57
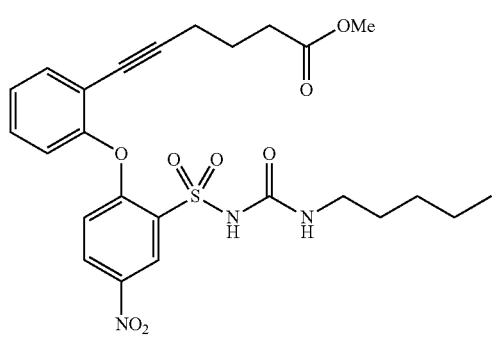
(XXVI)
Mw - 531.17
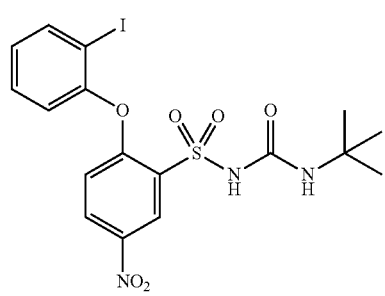
(VIII)
Mw - 519.31
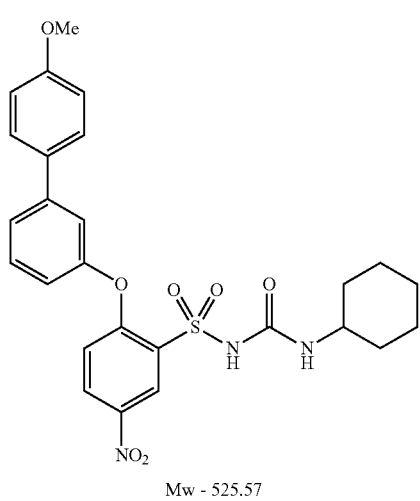
(XXVII)
Mw - 525.57
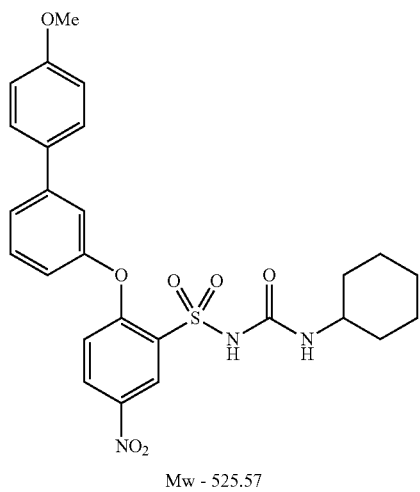
(XXIX)
Mw - 529.56

(XXX)
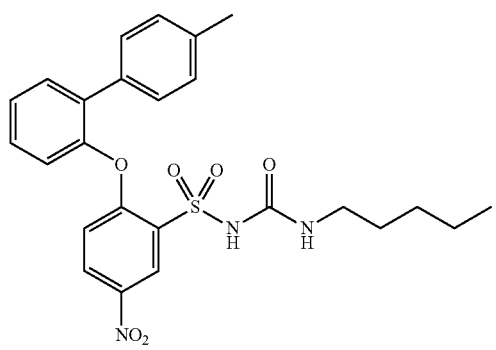
Mw - 497.56
(XXXI)
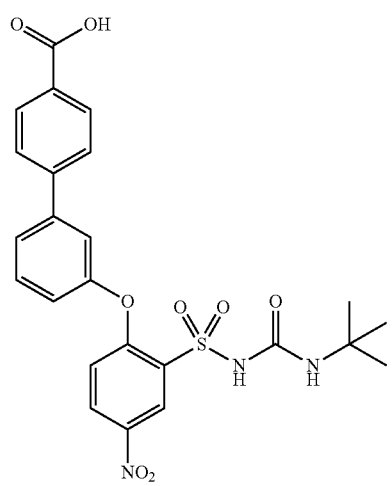
Mw - 513.5
(XXXII)
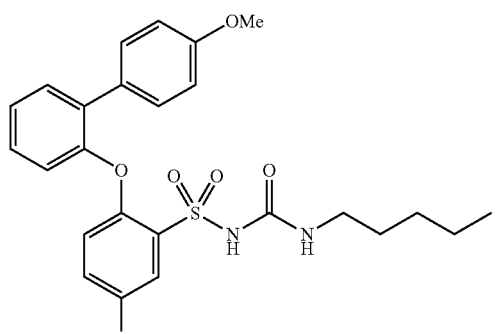
Mw - 513.56
(XXXIII)
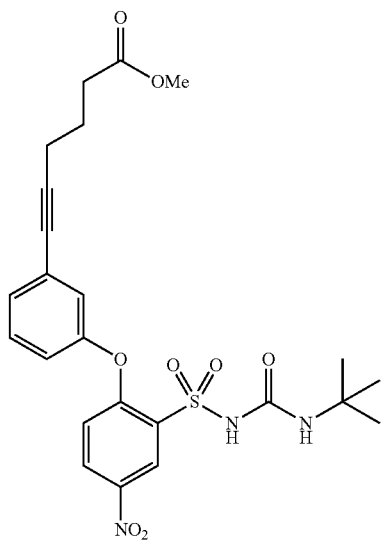
Mw - 517.55
(XXXIV)
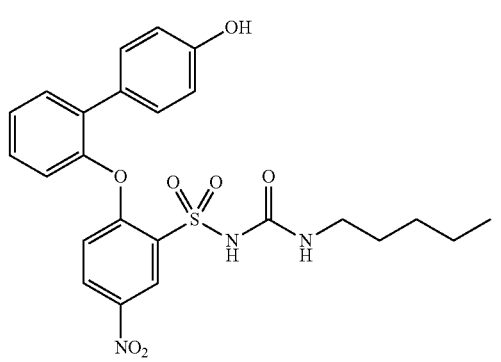
Mw - 499.54
(XXXV)
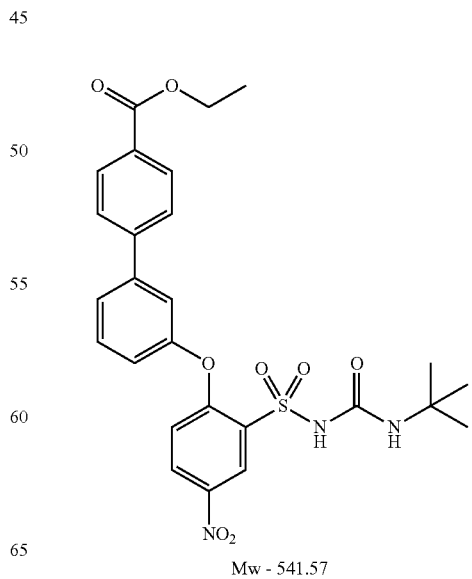
Mw - 541.57

(XXXVI)
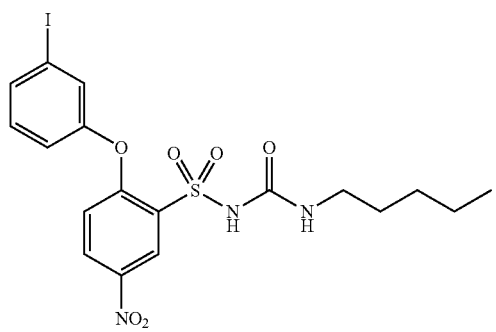
Mw - 533.34
(XXXVII)
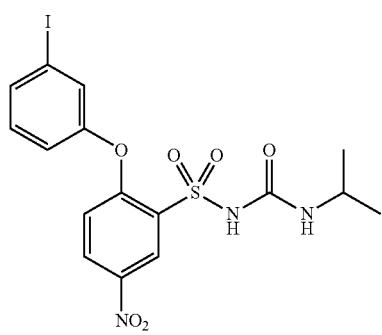
Mw - 505.28
(XXXVIII)
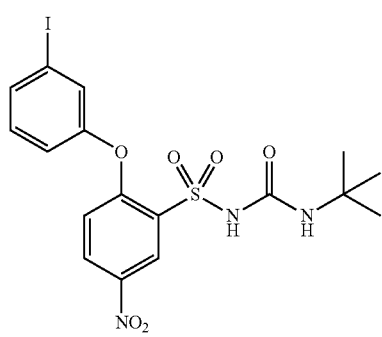
Mw - 519.31
(XXXIX)
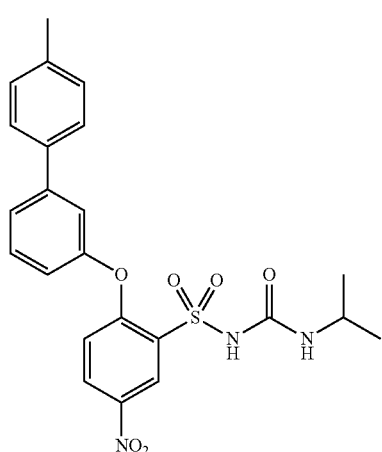
Mw - 469.51
(IX)
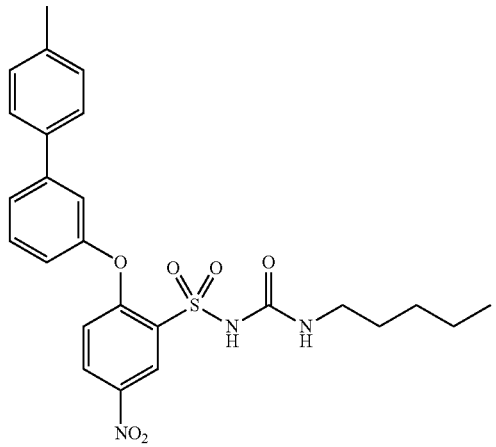
Mw - 497.56
(XL)
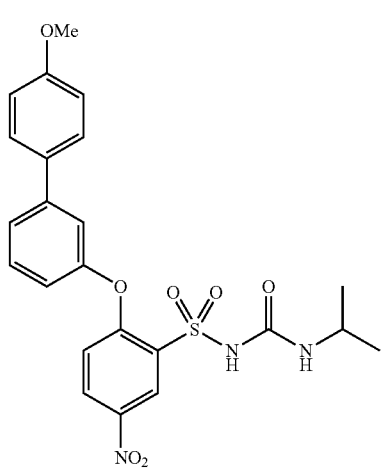
Mw - 485.51
(XLI)
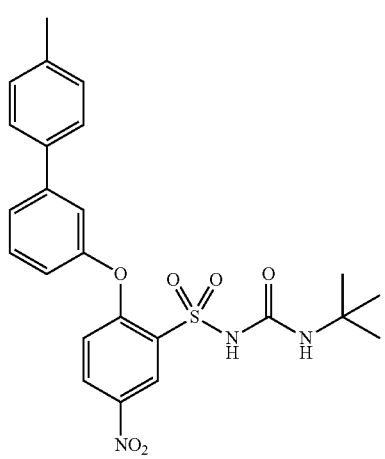
Mw - 483.54

-continued
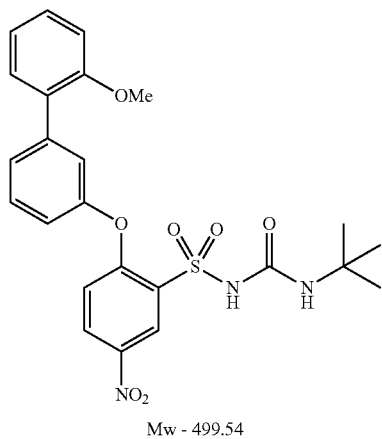
(XLII)
Mw - 499.54
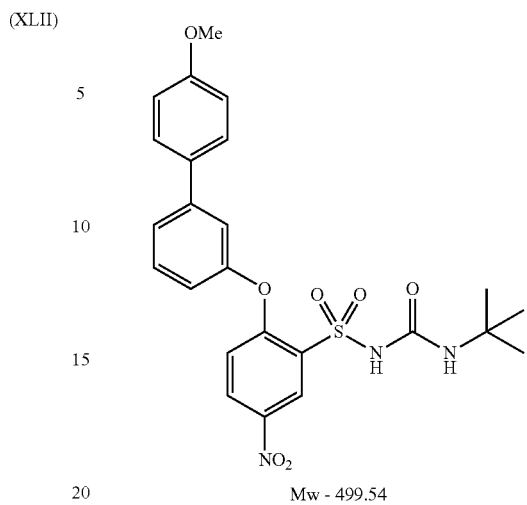
(X)
Mw - 499.54
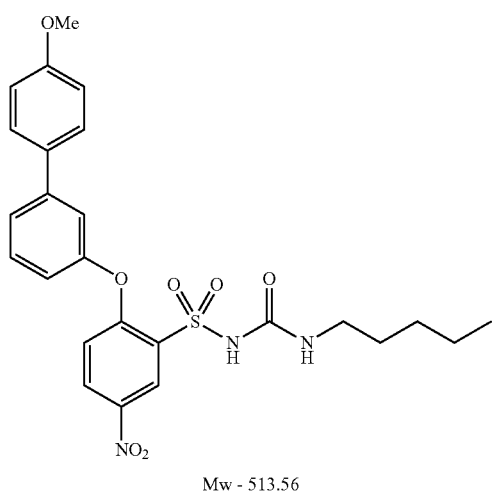
(XLIII)
Mw - 513.56
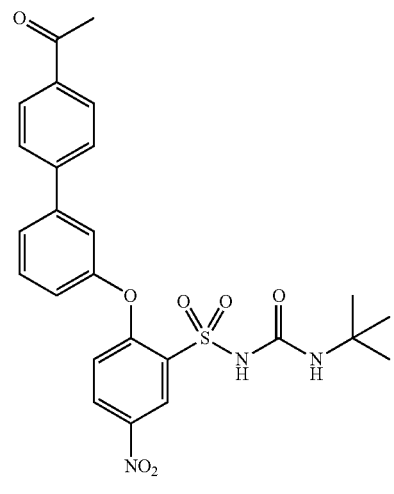
(XLV)
Mw - 511.55
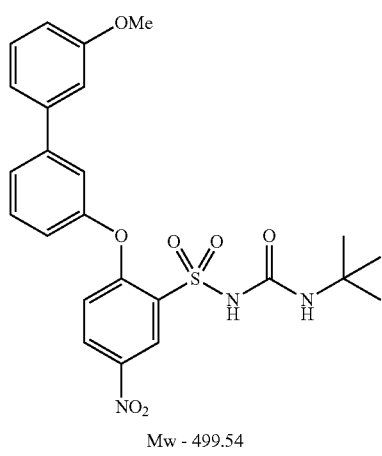
(XLIV)
Mw - 499.54
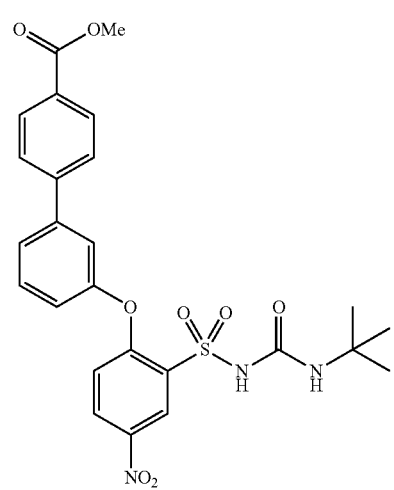
(XLVI)
Mw - 527.55

(XII)

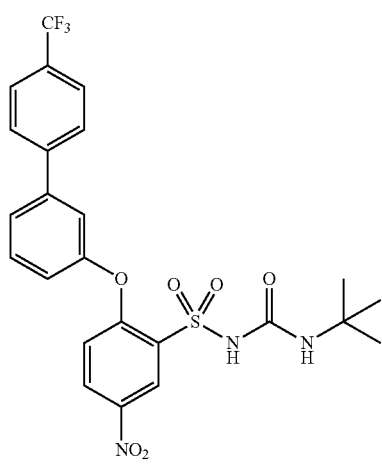

Mw - 537.51

(XLVII)

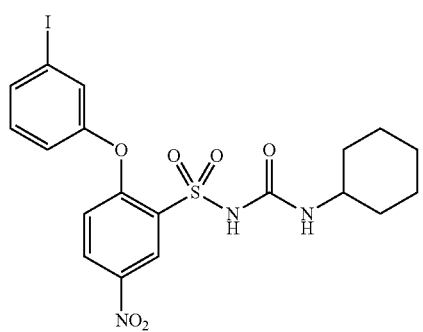

Mw - 545.35

(XI)

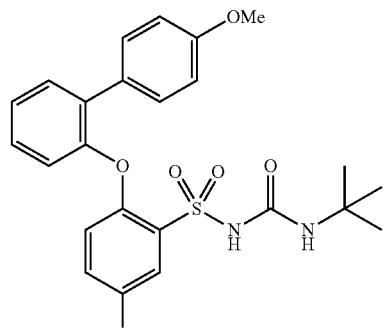

Mw - 499.54

Further compounds of the invention are synthesized according to Pathway E. Synthesis according to Pathway E begins with a compound of formula (LII). Compounds synthesized according to Pathway E can include any moiety known in the art at $R^{13}$. Exemplary moieties for $R^{13}$ include: I, $CF_3$, H, various organic groups, methoxy phenyl, methyl phenyl, trifluoromethyl phenyl, methyl ester, and H.

PATHWAY E

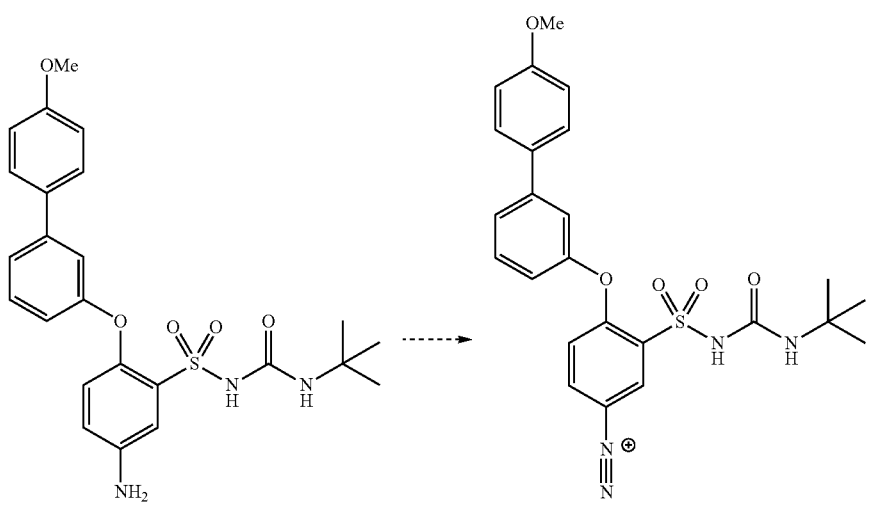

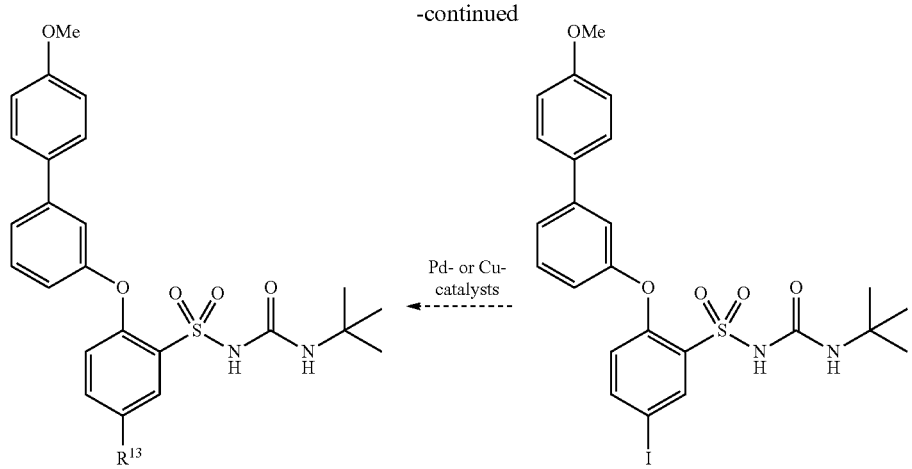
Compounds of the invention, for example, synthesized in-part according to Pathway E include compounds described by formulas (XVI), (XLVIII), (XVIII), (XLIX), (L), (LI), (LII), (LIII), (LIV), (LV), and (LVI):
(XVI)
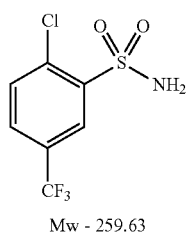
Mw - 259.63
(XVIII)
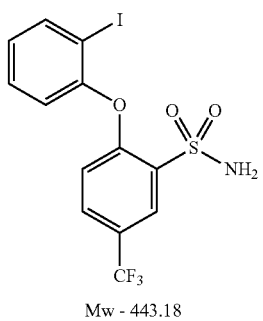
Mw - 443.18
(XLVIII)
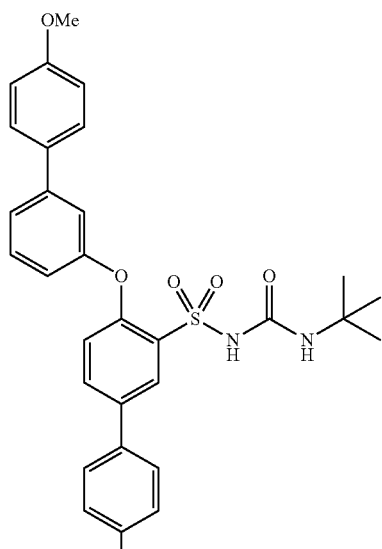
Mw - 544.66
(XLIX)
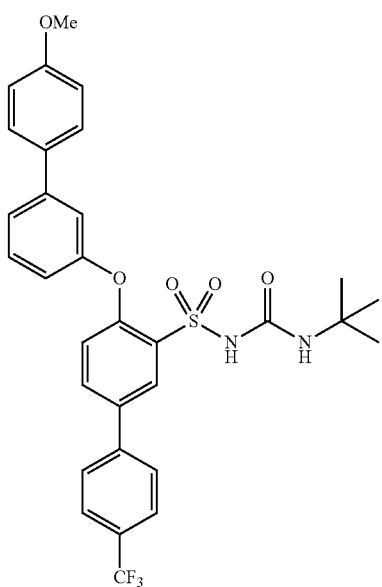
Mw - 598.63

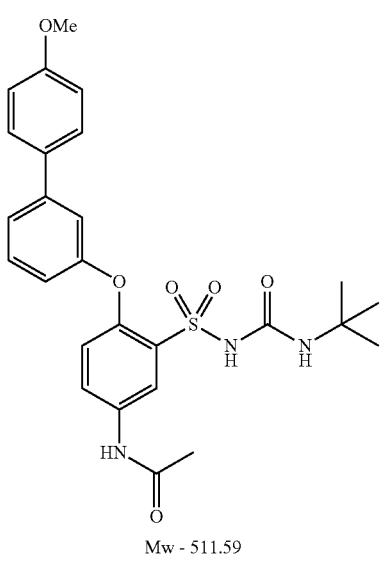
(L)
Mw - 511.59
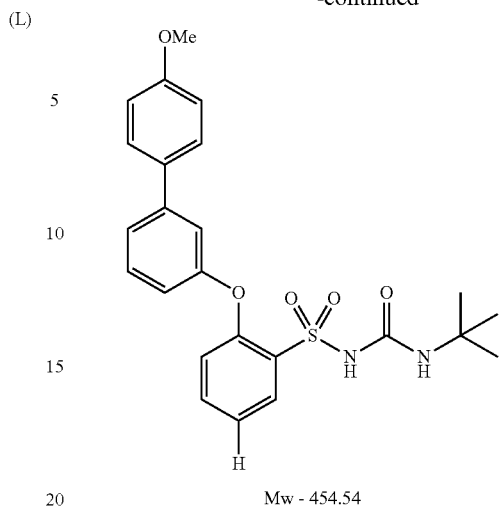
(LIII)
Mw - 454.54
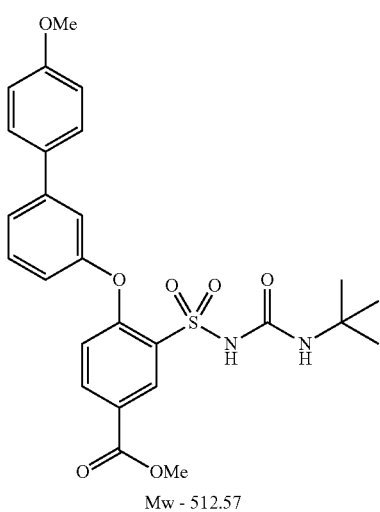
(LI)
Mw - 512.57
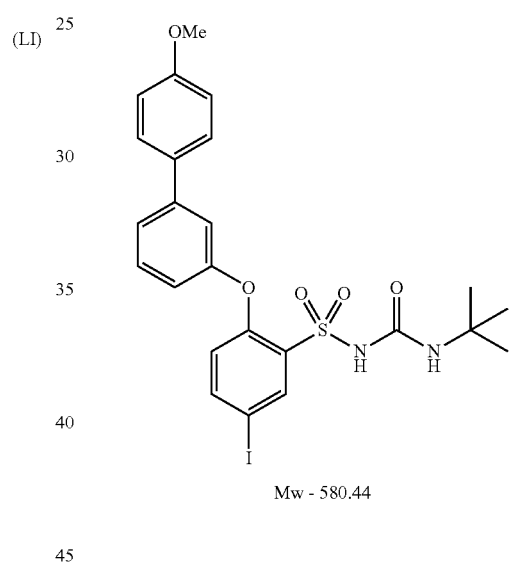
(LIV)
Mw - 580.44
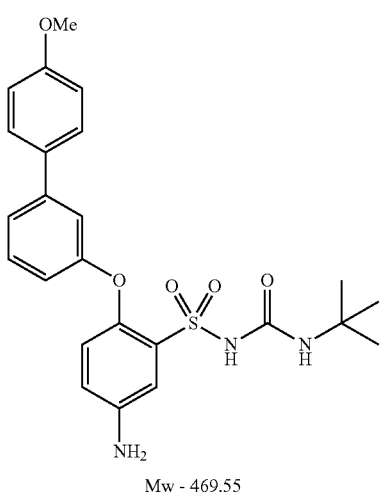
(LII)
Mw - 469.55
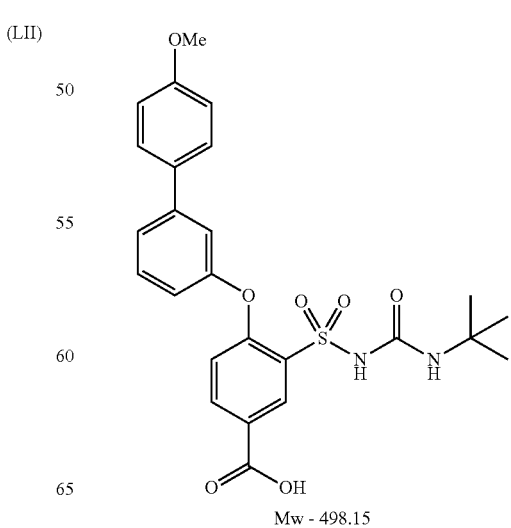
(LV)
Mw - 498.15

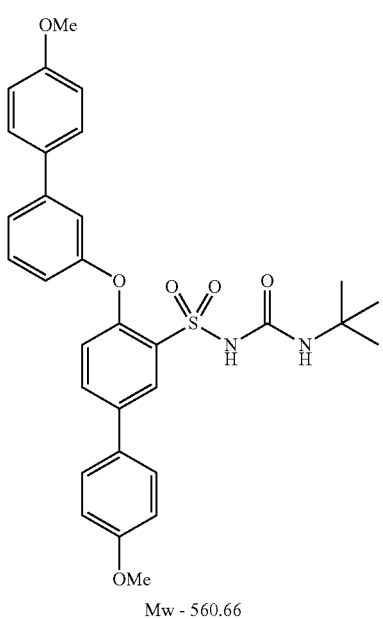

Mw - 560.66

Further compounds of the invention synthesized according to methods known in the art include compounds described by formulas QOM, (XVII), (XIV), (XIX), (XV), and (XX):

(XXI)

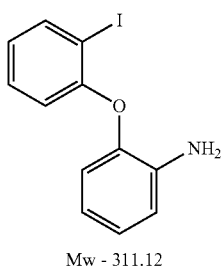

Mw - 311.12

(XVII)

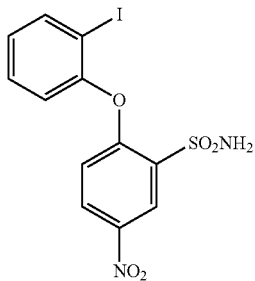

Mw - 420.18

(XIV)

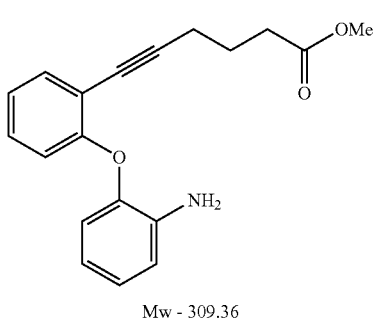

Mw - 309.36

(LVI)

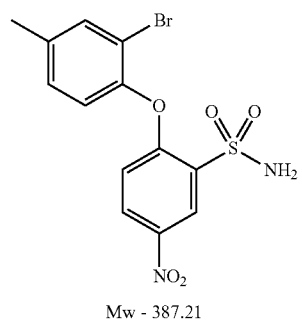

Mw - 387.21

(XV)

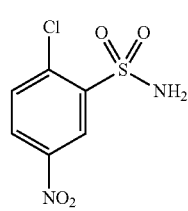

Mw - 236.63

(XX)

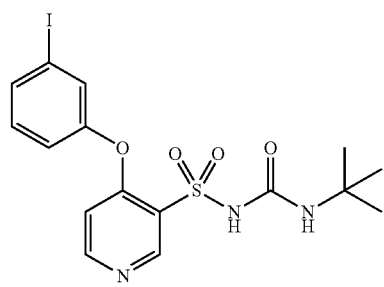

Mw - 475.30

In certain embodiments, the invention provides anticancer compounds that include a substituted nitro-phenoxy phenyl, a sulfonylurea, and an alkyl group. In some embodiments, the alkyl group is either an isopropyl group, a pentyl group, a tert-butyl group, or a cyclohexyl group. In some exemplary embodiments according to combinations of or modifications to the above-described synthetic pathways, the invention provides a TP antagonist including a compound represented by formula (I):

(I)

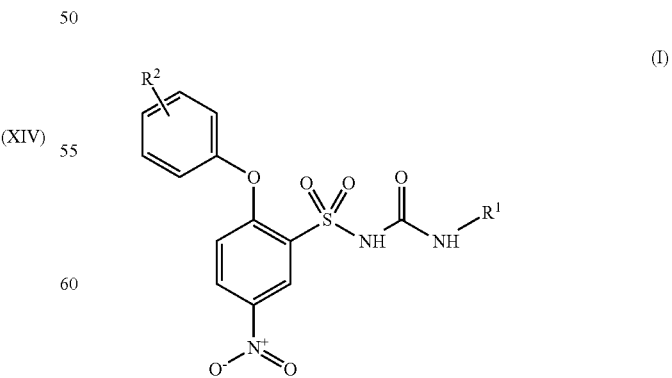

in which $R^1$ is a tert-butyl group or a pentyl group and $R^2$ is I,

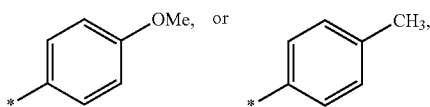 [SMILES: *c1ccc(OC)cc1 ; "or" ; *c1ccc(C)cc1]
optionally in the para position.
In certain embodiments the anticancer is represented by formula (XIII):
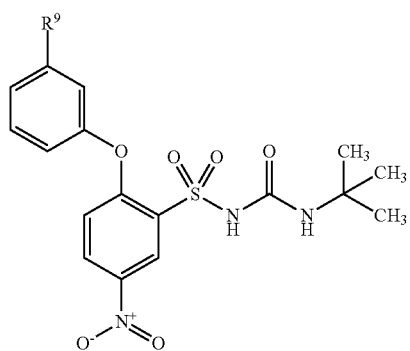
(XIII)
in which $R^9$ is
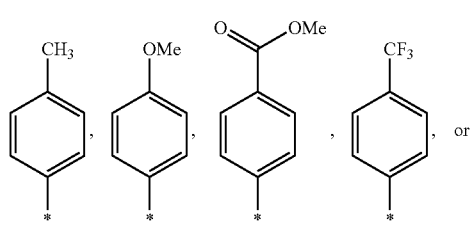
, or
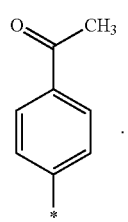
.
Exemplary compounds of the invention include compounds represented by any of formula LVII, LVIII, LIX, LX, LXI, LXII, and LXIII in which $R^1$, $R^2$, and X can have any form as disclosed herein throughout.
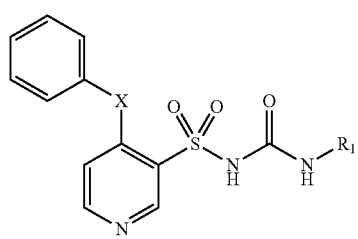
(LVII)
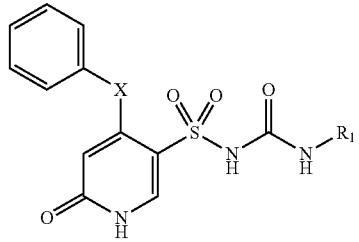
(LVIII)
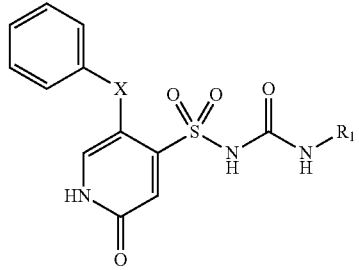
(LIX)
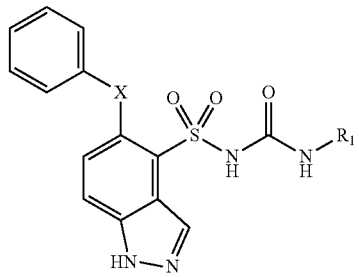
(LX)
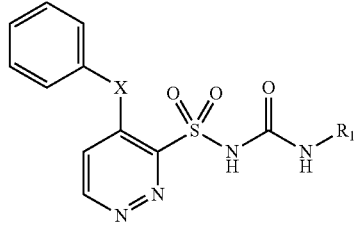
(LXI)
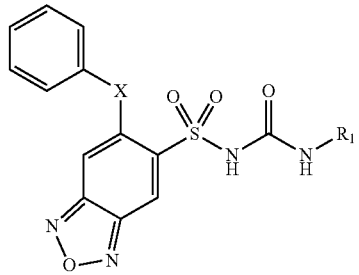
(LXII)
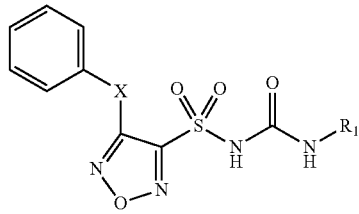
(LXIII)

In some embodiments, it may be beneficial to replace the nitro group of any of the foregoing compounds (e.g., the nitro group shown in formula (XIII) with a nitrile group (—CN) or other substituent.

The following synthetic pathways may be used to arrive at compounds of the present invention. Pathway F can be used to synthesize 2-Chloro-5-nitrobenzenesulfonamide for use as an intermediate.

PATHWAY F

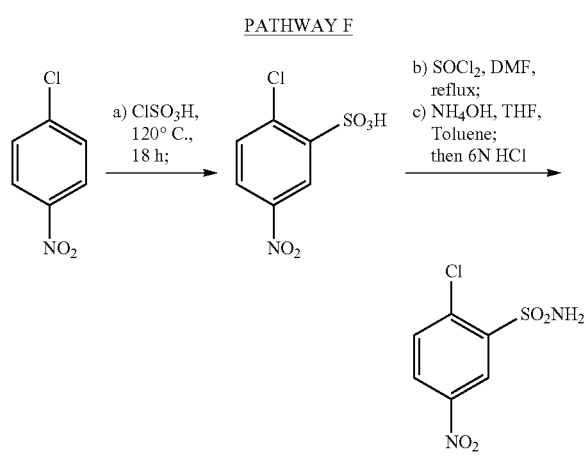

1-Chloro-4 nitrobenzene (6.93 g, 44 mmol) was added to chlorosulphonic acid (20 mL) and heated to 120° C. for 18 hours. After cooling to room temperature, the reaction was poured onto ice. The 2-chloro-5-nitrobenzene sulfonic acid was extracted with dichloromethane (DCM) and the organic phase was washed with brine, dried over MgSO₄ and then concentrated to dryness under vacuum. The reaction yielded 8.71 g of crude sulfonic acid and was used directly without further purification.

2-chloro-5-nitrobenzenesulfonic acid (44 mmol) was heated at reflux for 3.5 hours in a mixture of thionyl chloride (22 mL) and dimethylformamide (2 mL). After cooling the reaction mixture to room temperature, the solvents were removed under high vacuum. The crude solid was azeotroped with toluene (3×100 mL) to dryness under vacuum. The final residue was taken up in a mixture of toluene (20 mL) and tetrahydrofuran (50 mL) then cooled to 0° C. Ammonia (50 mL) was added to the stirred reaction mixture, then allowed to warns to room temperature overnight. The solution was acidified using 6 M HCl (pH ~4) and extracted with ethyl acetate (3×100 mL). The combined organics were dried over MgSO₄, filtered and then concentrated to dryness under vacuum to yield 2-Chloro-5-nitrobenzenesulfonamide as a light brown solid (3.91 g, 38% over 2 steps).

Pathway G yields 4'-methoxy-[1,1'-biphenyl]-3-ol.

PATHWAY G

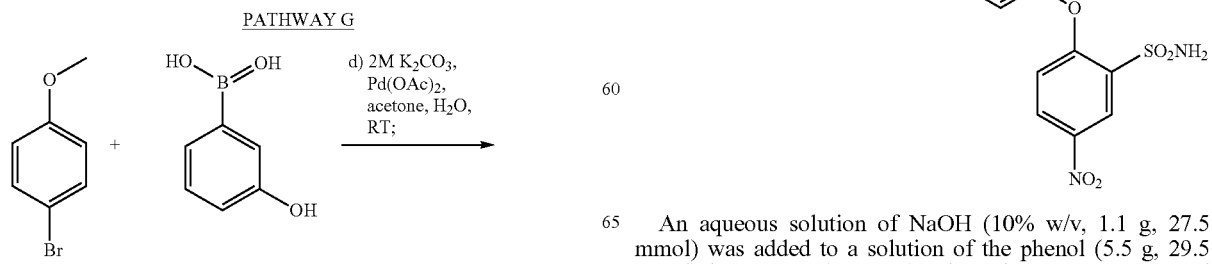

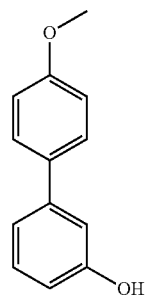

Nitrogen was bubbled through a mixture of 1-bromo-4-methoxybenzene (5.0 g, 26.8 mmol), 3-hydroxyphenylboronic acid (6.8 g, 49.6 mmol), aqueous potassium carbonate (2 M, 20 mL, 40 mmol), acetone (170 mL) and H₂O (300 mL) for 5 minutes. Pd(OAc)₂ (800 mg, 3.55 mmol) was added and the mixture was stirred under a nitrogen atmosphere at room temperature for 20 minutes, after which time LC-MS analysis showed the reaction to be complete. The reaction mixture was concentrated under vacuum then diluted with ethyl acetate (200 mL). The resulting suspension was filtered through a pad of celite, and the aqueous phase was then separated and extracted with EtOAc (2×100 mL). The combined organics were dried over MgSO₄, filtered and concentrated to dryness under vacuum. The crude product was loaded onto a 340 g Biotage silica cartridge and purified by Biotage chromatography (eluting with iso-hexane/EtOAc, gradient 0 to 50%). The target compound 4'-methoxy-[1,1'-biphenyl]-3-ol was isolated as a white solid (5.66 g, 78% yield).

Pathway H produced 2-((4'-methoxy-[1,1'-biphenyl]-3-yl)oxy)-5-nitrobenzenesulfonamide.

PATHWAY H

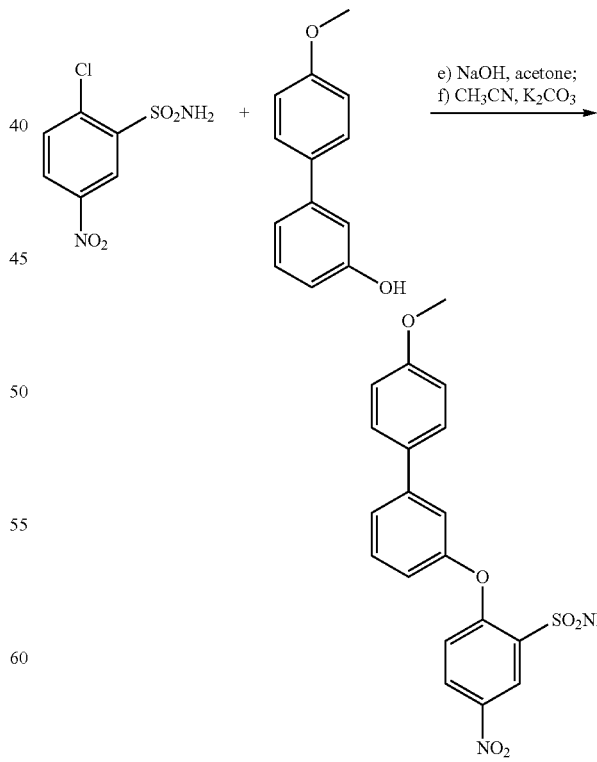

An aqueous solution of NaOH (10% w/v, 1.1 g, 27.5 mmol) was added to a solution of the phenol (5.5 g, 29.5 mmol) in acetone (100 mL). The solvents were removed under vacuum to afford the sodium salt, which was added to a solution of sulfonamide (5 g, 21.13 mmol) in acetonitrile (100 mL). The mixture was heated to reflux, potassium carbonate (2.0 g) was added and the mixture was heated at reflux for a further 18 hours. The reaction mixture was concentrated under vacuum, diluted with water (25 mL) and acidified with concentrated HCl (pH ~1). The aqueous phase was extracted with EtOAc (3×50 mL) and the combined organic phases were washed with brine, dried over MgSO$_4$, filtered and concentrated to dryness. The crude product was loaded onto a Biotage silica cartridge (100 g) and purified by Biotage chromatography (eluting with iso-hexane/EtOAc gradient 0 to 50%). The target compound nitrobenzene sulfonamide was isolated as an off white solid (7, 1.0 g, 50%).

Pathway I can be used to produce N-(tert-butylcarbamoyl)-2-((4'-methoxy-[1,1'-biphenyl]-3-yl)oxy)-5-nitrobenzene-sulfonamide represented by formula (X).

Biotage chromatography (eluting with 1-100% gradient iso-hexane/EtOAc). The crude product was re-dissolved in DMF (15 mL), NaH (60% in oil, 35 mg, 0.87 mmol) was added, followed by tert-butylisocyanate (110 µl, 0.95 mmol). The mixture was stirred at room temperature for 4 hours and then evaporated under high vacuum before loading onto a 50 g silica cartridge. The crude product was purified by Biotage chromatography (eluting 1-100% gradient iso-hexane/EtOAc), obtaining the title compound as an off white solid (Formula (X), 2.6 g, 99%).

5-amino-N-(tert-butylcarbamoyl)-2-((4'-methoxy-[1,1'-biphenyl]-3-yl)oxy)benzene-sulfonamide, or Formula (LII) is made from Formula (X) according to Pathway J.

PATHWAY I

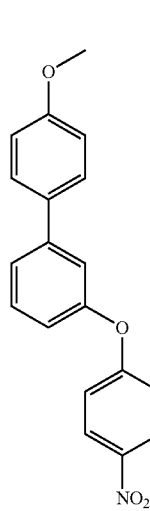

g) Acetone, KOH, H$_2$O, RT;
h) t-BuNCO, DMF;

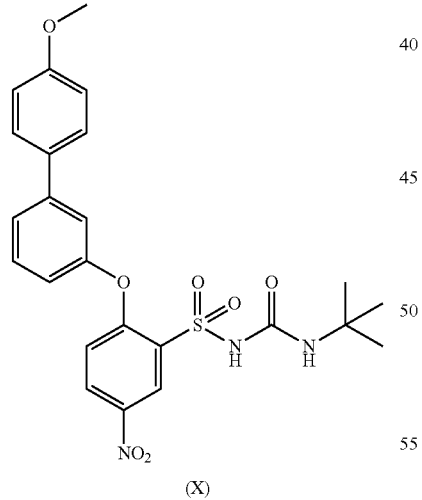

(X)

PATHWAY J

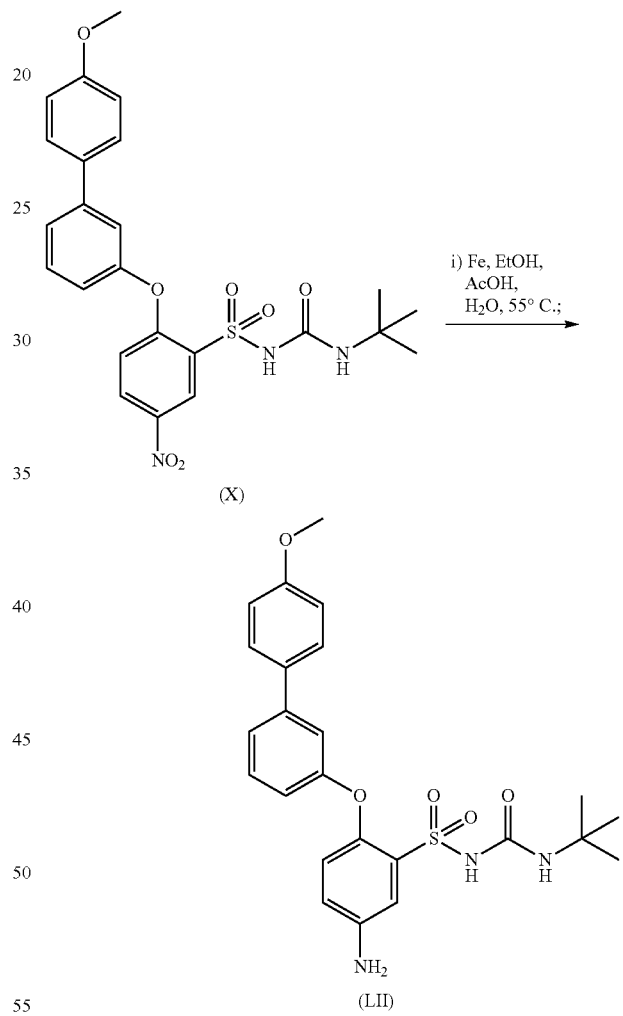

A solution of the sulfonamide (2.1 g, 5.24 mmol) in acetone (30 mL) was treated with a solution of potassium hydroxide (295 mg, 5.24 mmol) in water (1.8 mL). After stirring the reaction at room temperature for 15 minutes, the solvents were removed under vacuum. The residue was dissolved in DMF (30 mL), tert-butylisocyanate (1.2 mL, 10.4 mmol) was added and the reaction mixture was stirred at room temperature for 18 hours. The solvents were removed under high vacuum and the crude product was loaded onto a 50 g Biotage silica cartridge and purified by The nitrobenzene sulphonylurea (Formula (X), 2.6 g, 5.2 mmol) was heated with iron powder (1.74 g, 31 mmol), ethanol (15 mL), acetic acid (15 ml) and H$_2$O (7.5 mL) at 55° C. for 3 hours. After cooling to room temperature the reaction was diluted with EtOAc, the resulting suspension was then filtered through a small pad of celite. The filtrate was washed with 2 M KOH and the aqueous layer was extracted with EtOAc. The combined organics were washed with brine, dried over MgSO$_4$, filtered and concentrated under vacuum to yield the desired product as an off white solid (Formula (LII), 2.4 g, 98% yield).

Pathway K yields N-(tert-butylcarbamoyl)-5-chloro-2-((4'-methoxy-[1,1'-biphenyl]-3-yl)oxy)benzenesulfonamide (Formula (CX)).

PATHWAY K

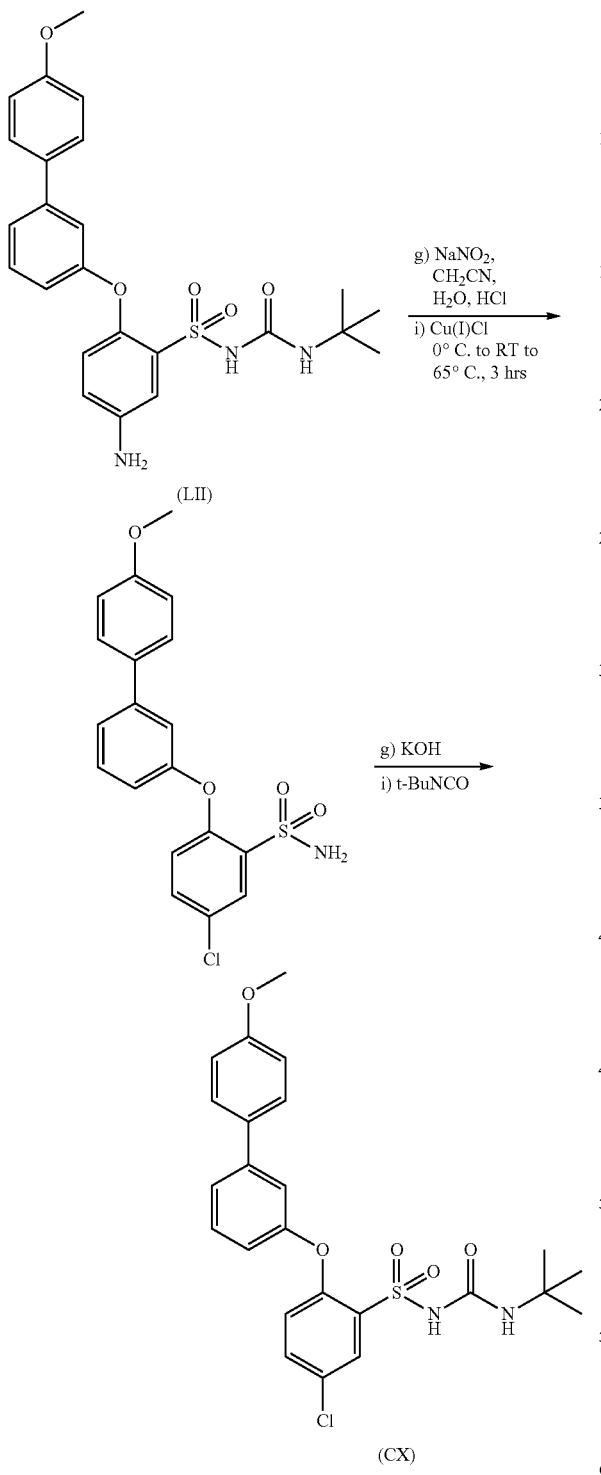

(CX)

The amino benzene sulfonamide (Formula (LII), 150 mg, 0.3198 mmol) was dissolved in acetonitrile (3 mL) and cooled to 0° C. Concentrated HCl (400 μL) was then added, followed by NaNO₂ (26.5 mg, 0.3838 mmol) and the mixture was then stirred for 20 minutes. A solution of Cu(I)Cl (63.3 mg, 0.6396 mmol) in H₂O (1 mL) was added and the mixture was stirred for a further 18 hours, allowing to warm to room temperature, after which time LC-MS analysis showed 5-10% conversion. Further Cu(I)Cl (60 mg) was added to the reaction and after heating to 65° C. for a further 3 hours, full conversion was confirmed by LC-MS. The reaction mixture was concentrated under vacuum and then diluted with water. The aqueous phase was extracted with EtOAc (3×50 mL). The combined organic phases were washed with brine, dried over MgSO₄, filtered and concentrated to dryness under vacuum. The crude solid was dissolved in acetone (2 mL) and added to a solution of KOH (1.8 mg) in H₂O (300 μL). The reaction mixture was stirred for 20 minutes before concentrating to dryness under vacuum. The solid was dissolved in DMF (2 mL) and tert-butylisocyanate (23 μL) was added and the reaction was stirred for 18 hours. The crude product was filtered through a syringe filter before purifying by preparative HPLC to give the desired product as an off-white solid (Formula (CX), 50 mg, 32% yield).

Pathway L makes 5-bromo-N-(tert-butylcarbamoyl)-2-((4'-methoxy-[1,1'-biphenyl]-3-yl)oxy)benzenesulfonamide represented by formula (LXI).

PATHWAY L

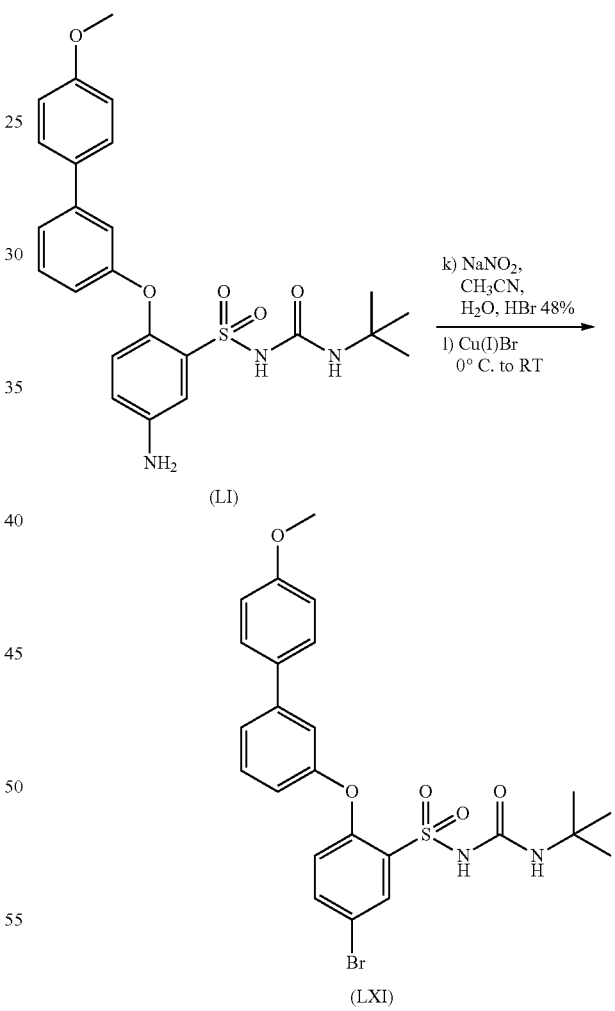

Hydrobromic acid (48%, 3.6 mL) was added to a stirred solution of NaNO₂ (318 mg, 4.606 mmol) and amino benzene sulfonamide (Formula (LI), 1.8 mg, 3.838 mmol) in CH₃CN (40 mL) and water (9 mL) at 0° C. The reaction mixture was maintained at 0° C. for 15 minutes and Cu(I)Br (1.21 g, 8.4436 mmol) was added. The mixture was allowed to warm to room temperature over 18 hours. The reaction mixture was diluted with water (50 mL) and extracted with EtOAc (3×100 mL). The combined organics were dried over MgSO₄, filtered and concentrated to dryness under vacuum. The crude product was loaded onto a 100 g silica cartridge and purified by Biotage chromatography (eluting with isohexane/EtOAc, gradient 0 to 100%), to yield the target compound 5-bromo-N-(tert-butylcarbamoyl)-2-((4'-methoxy-[1,1'-biphenyl]-3-yl)oxy)benzenesulfonamide as a white solid (Formula LXI, 0.92 g, 96.4%).

Pathway M provides for the synthesis of an intermediate N-(tert-butylcarbamoyl)-5-cyano-2-((4'-methoxy-[1,1'-biphenyl]-3-yl)oxy)benzenesulfonamide, formula (LXII), from the compound represented by formula (LI).

PATHWAY M

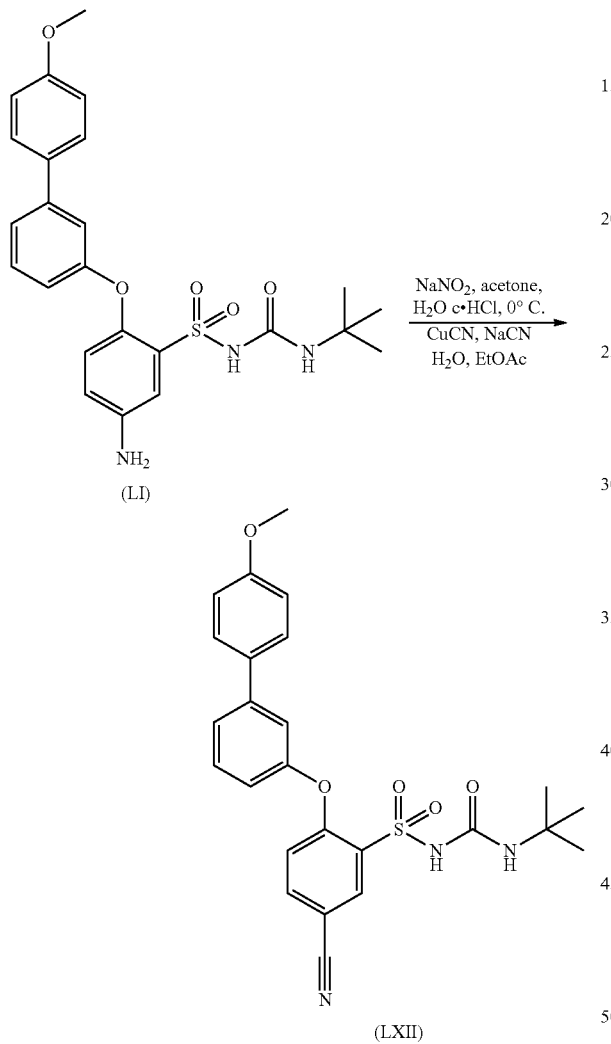

(LXII)

To a solution of the amino benzene sulfonamide (Formula (LI), 100 mg, 0.213 mmol) in acetone (10 mL) and water (1 mL) at 0° C., hydrochloric acid (37%, 500 µl) was added, followed by a solution of NaNO₂ (18 mg, 0.26 mmol) in H₂O (1 mL). The reaction mixture was stirred at 0° C. for 20 minutes after which time it was poured onto a solution of NaCN (45 mg, 0.92 mmol) and CuCN (30 mg, 0.33 mmol) in H₂O (10 mL) and EtOAc (5 mL), stirring at room temperature for 4 hours. The reaction mixture was diluted and extracted with EtOAc (3×100 mL). The combined organics were washed with brine, dried over MgSO₄, filtered and then concentrated to dryness under vacuum. The crude product was diluted with DMSO (1.5 mL) and then purified by preparative HPLC to yield the target compound N-(tert-butylcarbamoyl)-5-cyano-2-((4'-methoxy-[1,1'-biphenyl]-3-yl)oxy)benzenesulfonamide as a white solid (Formula (LXII), 7.51 mg, 7.3%).

Synthesis of various compounds from compound represented by formula (LXI) is described.

In some embodiments, a test Suzuki provides N-(tert-butylcarbamoyl)-5-(1-ethyl-1H-pyrazol-4-yl)-2-((4'-methoxy-[1,1'-biphenyl]-3-yl)oxy)benzenesulfonamide, formula (LXIII), from compound represented by formula (LXI) provided by Pathway L, as described below in Pathway N.

PATHWAY N

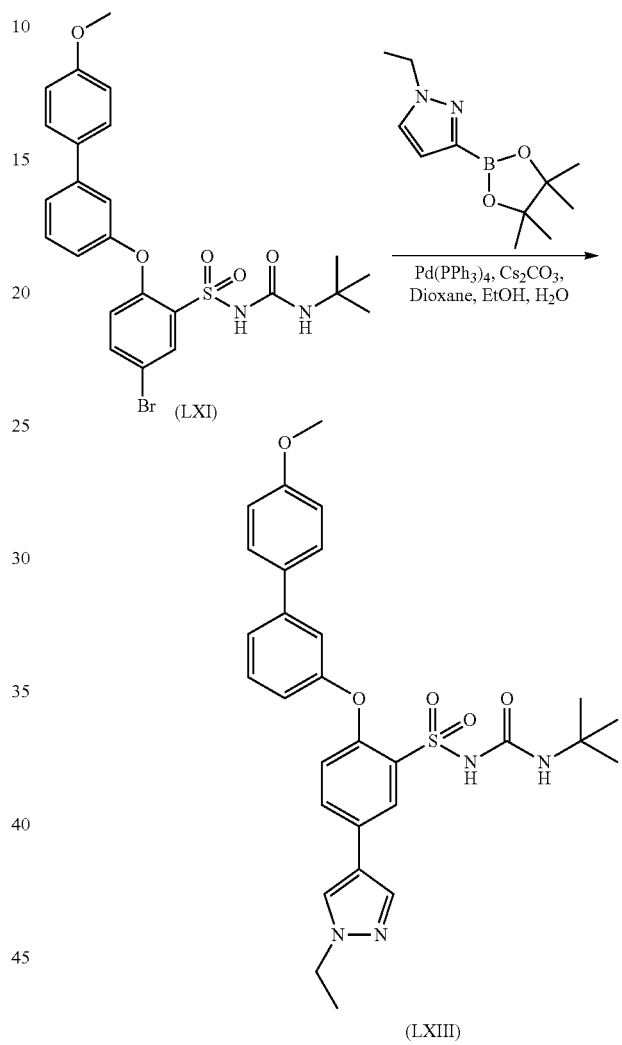

(LXIII)

The bromo benzene sulfonamide (Formula (LXI), 50 mg, 0.09375 mmol), Pd(PPh₃)₄ (10.8 mg, 0.009375 mmol), Cs₂CO₃ (73.11 mg, 0.2249 mmol), dioxane (1 mL), EtOH (0.5 mL), H₂O (0.15 mL) and the boronate (61 mg, 0.1875 mmol) were added to a ste, tube under N₂. The reaction tube was degassed for 5 minutes, sealed and then heated to 80° C. for 18 hours, after which time LC-MS analysis showed ~60% conversion. The solvents were removed under vacuum and the residue was diluted with water and extracted with DCM. The organic phase was removed and concentrated to dryness under vacuum. The crude product was dissolved in DMSO (1.5 mL) and then purified by preparative HPLC to yield the target compound as an off-white solid (Formula (LXIII), 14.4 mg, 28%).

Using C-Linked palladium array chemistry, as shown in Pathway 0 below, arrives at a number of compounds based on the compound represented by formula (XXII) and starting with the compound represented by formula (LXI). This is shown in Pathway 0, below, where Table 1.1 shows which boronate compound reactant and in what amount to use to yield which product.

PATHWAY O
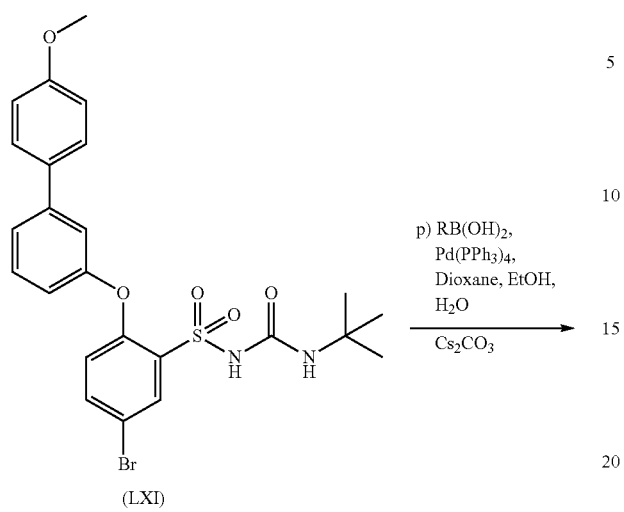
(LXI)
p) RB(OH)$_2$,
Pd(PPh$_3$)$_4$,
Dioxane, EtOH,
H$_2$O
Cs$_2$CO$_3$
-continued
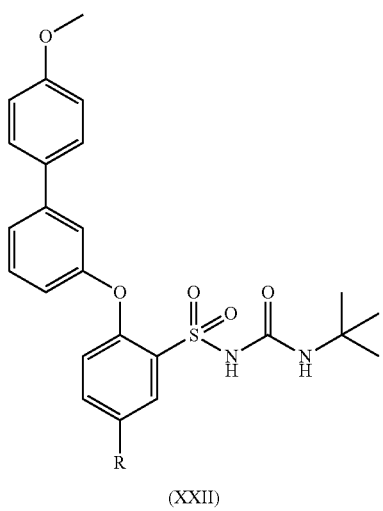
(XXII)
TABLE 1.1
| | C-Linked Palladium Array Chemistry | |
|---|---|---|
| Boronate reactant | Amount (mg); Amount(mmol); Yield (mg, %) | Target Compound/product |
| (pyrazole-Boc pinacol boronate structure) | 49.63; 0.1687; 20 mg, 17% | (LXIV) |

TABLE 1.1-continued

C-Linked Palladium Array Chemistry

| Boronate reactant | Amount (mg); Amount(mmol); Yield (mg, %) | Target Compound/product |
|---|---|---|
| [3,5-dimethylisoxazol-4-yl boronic acid pinacol ester] | 37.64; 0.1687; 6 mg, 9% | (LXV) |
| [furan-3-yl boronic acid] | 18.88; 0.1687 g; 33 mg, 56% | (LXVI) |

TABLE 1.1-continued

C-Linked Palladium Array Chemistry

| Boronate reactant | Amount (mg); Amount(mmol); Yield (mg, %) | Target Compound/product |
|---|---|---|
| furan-2-ylboronic acid | 18.88; 0.1687; 33 mg, 56% | (LXVII) |
| pyridin-4-ylboronic acid | 20.74; 0.1687; 7.8 mg, 13% | (LXVIII) |

For each of the target reactions, bromo benzene sulfonamide (Formula (LXI), 60 mg, 0.1125 mmol), Pd(PPh$_3$)$_4$ (13 mg, 0.01125 mmol), Cs$_2$CO$_3$ (73.11 mg, 0.2249 mmol), dioxane (1 mL), EtOH (0.5 mL), H$_2$O (0.15 mL) and the corresponding boronates, as indicated in Table 1.1, were added to a stem tube under N$_2$. The reaction tubes were degassed for 5 minutes, sealed and then heated to 80° C. for 18 hours. The solvents were removed under vacuum and diluted with water, then extracted with DCM. The organic phase was removed and concentrated to dryness under vacuum. The crude products were dissolved in DMSO (1.5 mL) and then purified by preparative HPLC to yield the desired target compounds represented by formulas (LXIV), (LXV), (LXVI), (LXVII), and (LXVIII) with yields as indicated in Table 1.1.

The Stille reaction shown in Pathway P can produce N-(tert-butylcarbamoyl)-2-((4'-methoxy-[1,1'-biphenyl]-3-yl)oxy)-5-(2-methoxythiazol-4-yl)benzenesulfonamide, formula (LXIX), from (LXI).

PATHWAY P

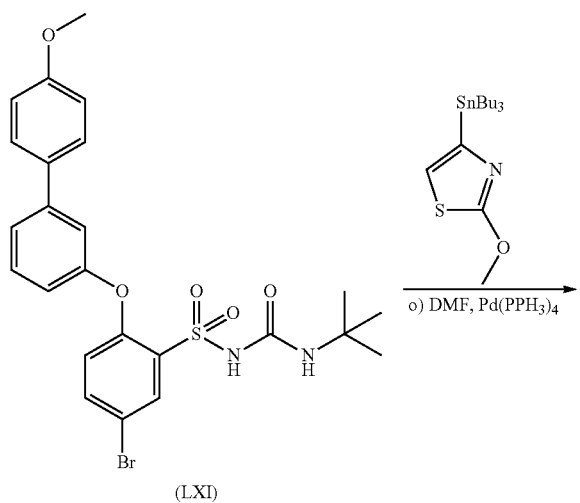

(LXI)

(LXIX)

Pd(PPh$_3$)$_4$ (13 mg, 0.01125 mmol) was added to a N$_2$ flushed reaction tube containing the sulphonamide (Formula (LXI), 60 mg, 0.1125 mmol), DMF (1.5 mL) and the tributyl stannyl thiazole (68 mg, 0.1688 mmol). The reaction tube was flushed with N$_2$ before sealing the tube and heating to 80° C. for 18 hours, after which time, LC-MS analysis confirmed complete conversion. The crude product was filtered and then purified by preparative HPLC to yield the product as a white solid (Formula (LXIX), 29 mg; 45%).

Pathway Q, shown below, produces 5-acetyl-N-(tert-butylcarbamoyl)-2-((4'-methoxy-[1,1'-biphenyl]-3-yl)oxy)benzenesulfonamide, formula (LXX), from (LXI).

PATHWAY Q

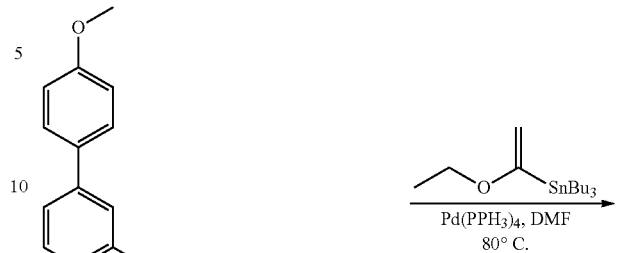

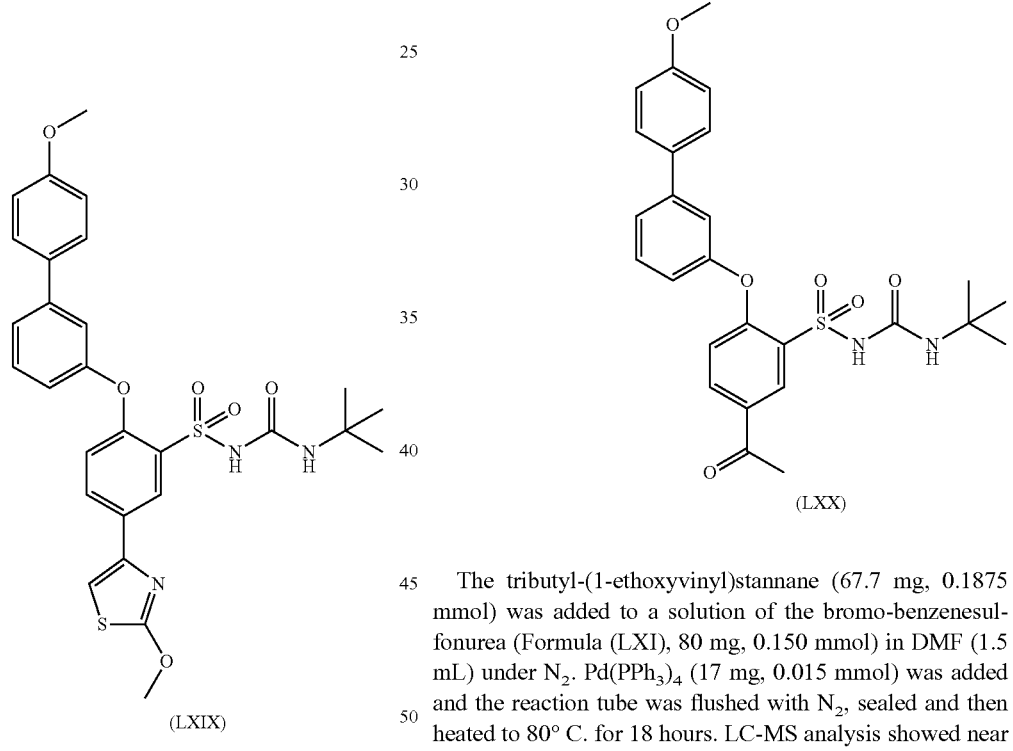

(LXI)

(LXX)

The tributyl-(1-ethoxyvinyl)stannane (67.7 mg, 0.1875 mmol) was added to a solution of the bromo-benzenesulfonurea (Formula (LXI), 80 mg, 0.150 mmol) in DMF (1.5 mL) under N$_2$. Pd(PPh$_3$)$_4$ (17 mg, 0.015 mmol) was added and the reaction tube was flushed with N$_2$, sealed and then heated to 80° C. for 18 hours. LC-MS analysis showed near complete reaction to the vinyl ether intermediate. The DMF was removed under high vacuum and HCl (2M, 1 mL) was added followed by THF (1 mL). The reaction was stirred for 1 hour after which time LC-MS analysis confirmed complete conversion to the desired product. The solvents were removed under vacuum and the residue was diluted with water, extracting with DCM. The organic phase was removed and concentrated to dryness under vacuum. The crude products were dissolved in DMSO (1.5 mL) and purified by preparative HPLC to yield the target compound as a white solid (Formula (LXX), 15.2 mg, 20%).

Methyl 4-fluoro-3-sulfamoylbenzoate, formula (LXXI) is a product of pathway R and an intermediate in synthetic pathways disclosed herein.

PATHWAY R

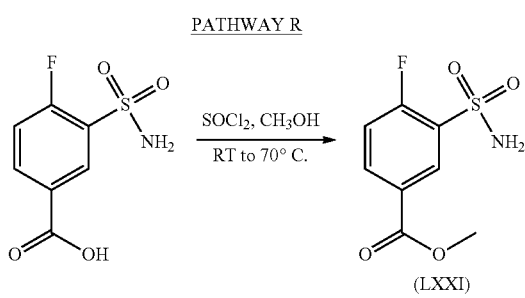

Thionyl chloride (3 mL) was added to a solution of 4-fluoro-3-sulfamoylbenzoic acid (1.8 g, 8.91 mmol) in methanol (100 mL). The resulting mixture was heated at 70° C. for 3 hours and then evaporated to dryness under vacuum. The resulting crude solid was re-dissolved in DCM and washed with water. The organic phase was dried over MgSO$_4$, filtered and evaporated to dryness to provide desired product as a beige solid (Formula (LXXI), 1.5 g, 78% yield).

In Pathway S, Methyl 4-((4'-methoxy-[1,1'-biphenyl]-3-yl)oxy)-3-sulfamoylbenzoate, Formula (LXXII), is produced.

PATHWAY S

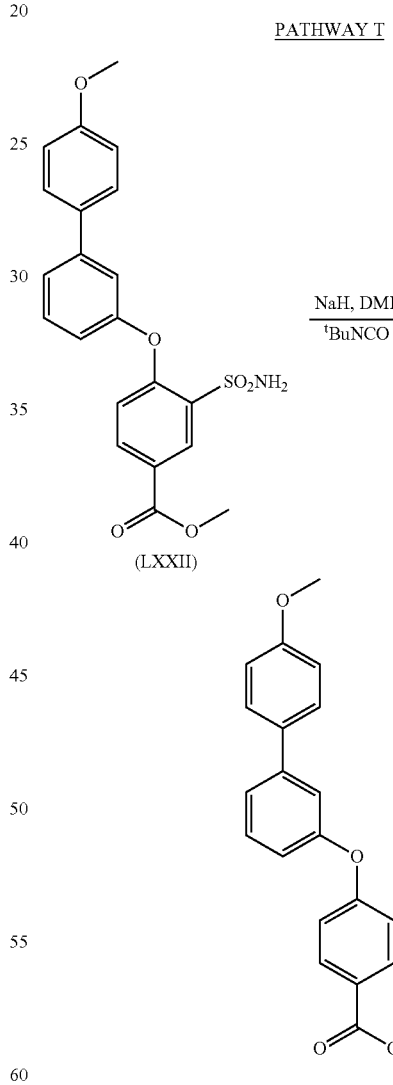

An aqueous solution of NaOH (40% w/v, 380 mg, 27.5 mmol) was added to a solution of the phenol (1.9 g, 9.5 mmol) in acetone (50 mL). The reaction mixture was stirred for 10 minutes then evaporated to dryness under high vacuum. The residue was dissolved in acetonitrile (60 mL) and then the sulfonamide (Formula (LXXI), 2.0 g, 8.6 mmol) and potassium carbonate (840 mg) were added. The resulting mixture was heated to 90° C. for 18 hours. The solvents were removed under vacuum and the crude solid obtained was partitioned between water and EtOAc (100 mL), acidifying to pH ~1 with concentrated HCl. The aqueous phase was removed and re-extracted with EtOAc (2×100 mL) and the combined organic phases were washed with brine, dried over MgSO$_4$, filtered and evaporated to dryness. The crude product was loaded with DCM, onto a silica cartridge (25 g) and then purified by Biotage chromatography (eluting with iso-hexane/EtOAc gradient 20 to 100% EtOAc). The target compound nitrobenzene sulfonamide was isolated as a white solid (Formula (LXXII), 2.64 g, 75%).

Pathway T produces Methyl 3-(N-(tert-butylcarbamoyl)sulfamoyl)-4-((4'-methoxy-[1,1'-biphenyl]-3-yl)oxy)benzoate, represented by formula (LXXIII), from compound formula (LXXII).

PATHWAY T

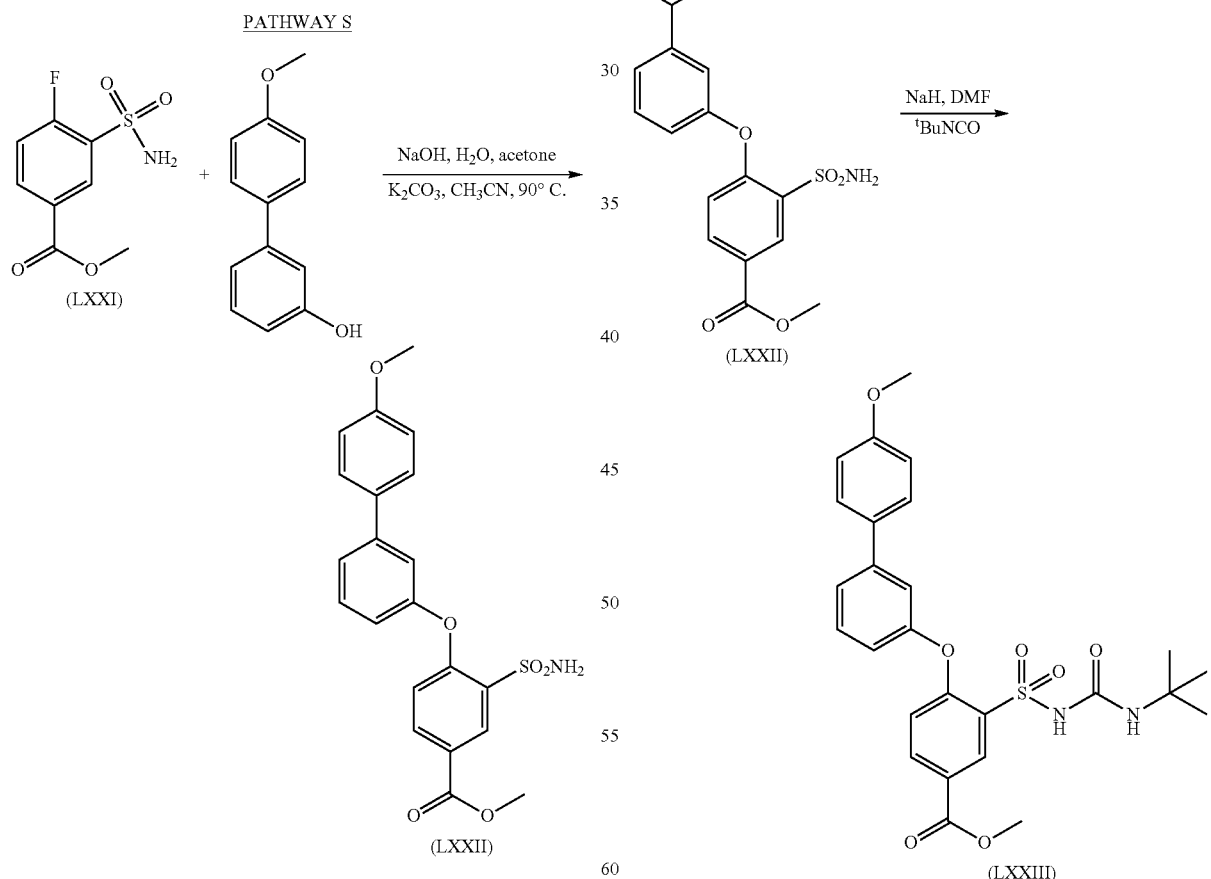

Sodium hydride (60% in oil, 281 mg, 7.0 mmol) was added to a solution of the nitrobenzene sulfonamide (Formula (LXXII), 2.64 g, 6.4 mmol) in DMF (50 mL). The mixture was stirred for 10 minutes at ambient temperature before the addition of tert-butylisocyanate (1 mL, 8.7 mmol). The resulting mixture was stirred overnight at room temperature. The solvents were removed under high vacuum and then the crude solid obtained was partitioned between water and EtOAc (50 mL), before acidifying the aqueous with 1 M HCl (pH ~1). The aqueous phase was removed and re-extracted with EtOAc (2×50 mL) and the combined organic phases were dried over MgSO4, filtered and evaporated to dryness under vacuum to yield the desired product (Formula (LXXIII), 2.8 g, 86%).

Below, 3-(N-(tert-butylcarbamoyl)sulfamoyl)-4-((4'-methoxy-[1,1'-biphenyl]-3-yl)oxy)benzoic acid, formula (LXXIV) is produced from (LXXIII) by pathway U.

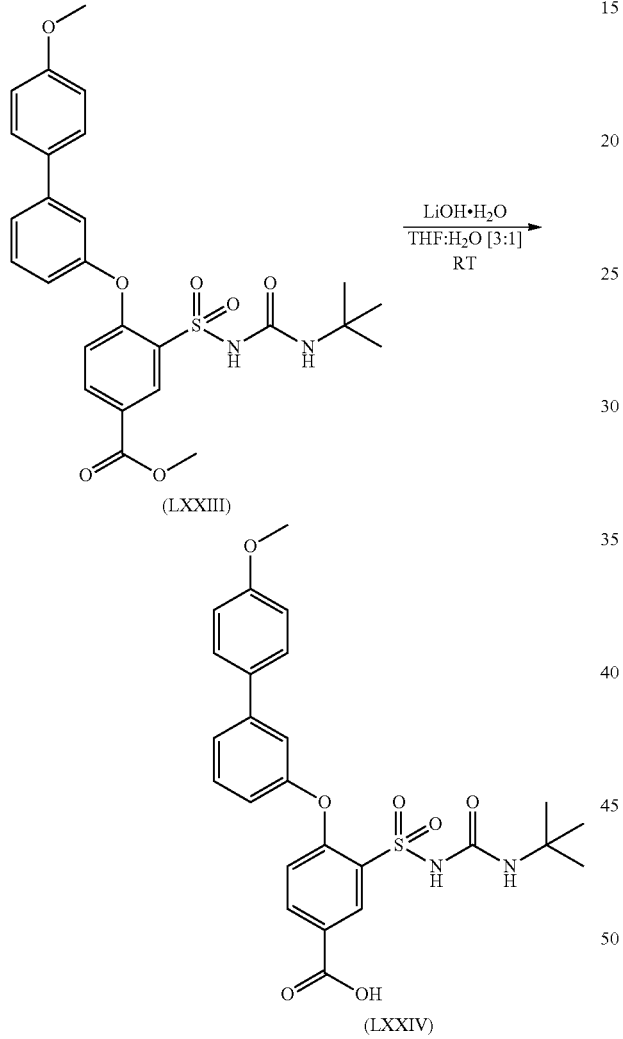

Lithium hydroxide monohydrate (262 mg, 6.243 mmol) was added to a solution of the methyl ester (Formula (LXXIII), 2.0 g, 3.902 mmol) in THF (100 mL) and H₂O (33 mL). The mixture was stirred at room temperature for 18 hours and then evaporated to dryness under vacuum. The residue was dissolved in H₂O and acidified using concentrated HCl (pH ~1). The resulting white solid was removed by filtration, re-dissolved in EtOAc (50 mL), and dried by passing through a hydrophobic filter before evaporating to dryness under vacuum to give the desired product as a white solid (Formula (LXXIV), 1.7 g, 87% yield).

Synthesis of various compounds from the compound represented by formula (LXXIV) is described.

Pathway V shows synthesis of 3-(N-(tert-butylcarbamoyl)sulfamoyl)-4-((4'-methoxy-[1,1'-biphenyl]-3-yl)oxy)-N,N-dimethylbenzamide, formula (LXXV), from compound formula (LXXIV).

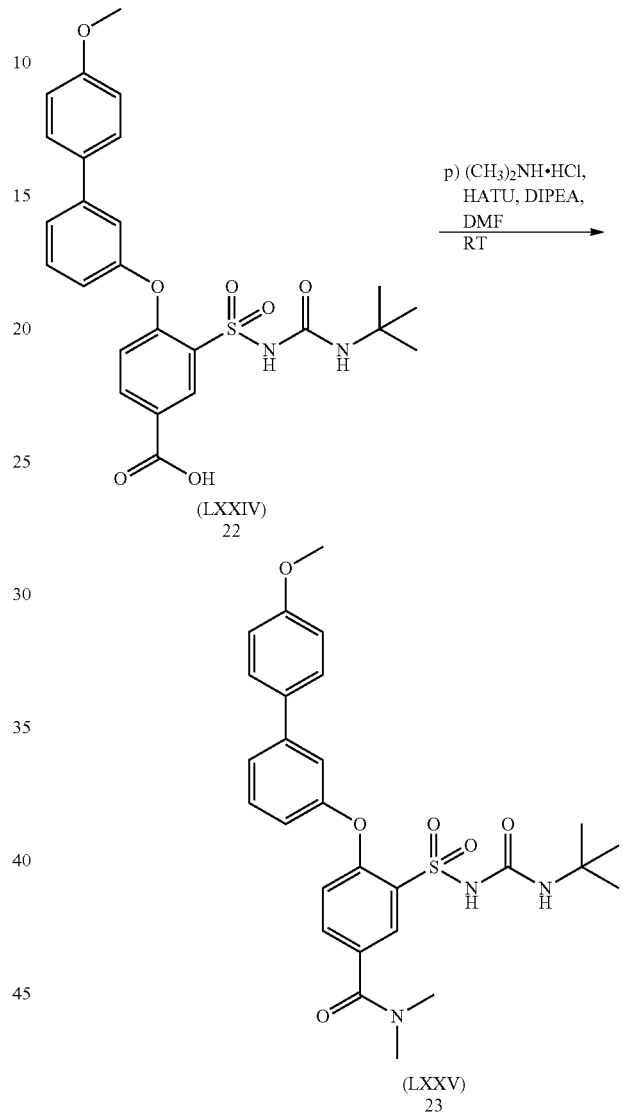

The amine (16 mg, 0.196 mmol), HATU (71 mg, 0.1868 mmol) and DIPEA (120 µL) were successively added to a solution of the acid (Formula LXXIV), 85 mg, 0.170 mmol) in DMF (4 mL). The resulting mixture was stirred at room temperature for 18 hours, after which time LC-MS analysis confirmed ~80% conversion to the target compound. The DMF was removed under high vacuum and the residue taken up in in EtOAc (20 mL) and H₂O (10 mL). The aqueous phase was acidified using concentrated HCl (pH ~2) and then extracted with EtOAc (2×20 mL). The combined organics were dried over MgSO₄, filtered and evaporated to dryness. The crude product was dissolved in DMSO (1.5 mL), filtered and then purified by preparative HPLC to yield a white solid (Formula (LXXV), 41 mg, 98.3%).

Pathway W shows an amide array synthesis of various amides as listed in Table 1.2 from compound Formula (LXXV).

PATHWAY W
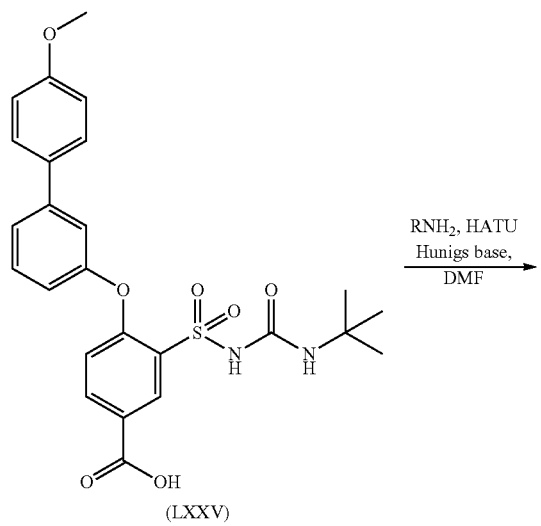
TABLE 1.2
Amide Array: Synthesis of various amides from (LXXV)
| Amine | Amount (mg); Amount (mmol); Yield (mg; %) | Target Compound |
|---|---|---|
| ⟍NH₂Cl | 16.25; 0.2407; 54 mg; 65% | (LXXVI) |

TABLE 1.2-continued
Amide Array: Synthesis of various amides from (LXXV)
| Amine | Amount (mg);<br>Amount (mmol);<br>Yield (mg; %) | Target Compound |
|---|---|---|
| H₂N⌒ | 10.85;<br>0.2407; 28<br>mg; 33% | 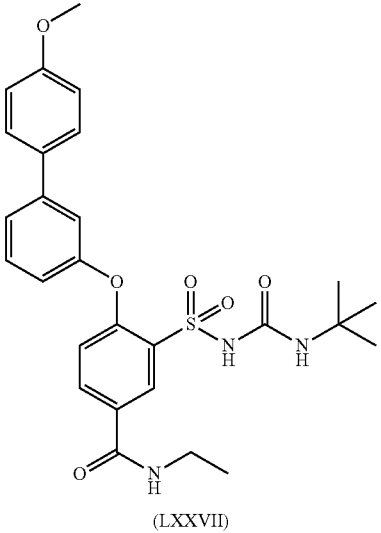 [SMILES: CCNC(=O)c1ccc(Oc2cccc(-c3ccc(OC)cc3)c2)c(S(=O)(=O)NC(=O)NC(C)(C)C)c1]<br>(LXXVII) |
| NH₄Cl | 12.88;<br>0.2407; 49<br>mg; 61% | 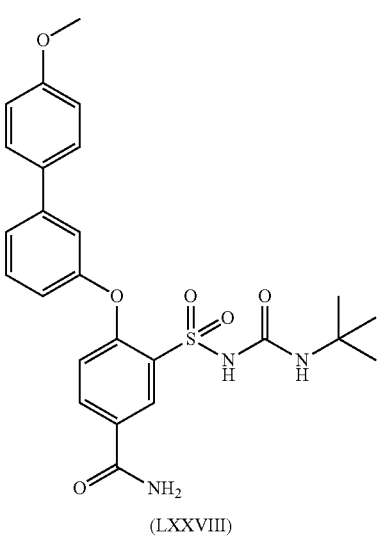 [SMILES: COc1ccc(-c2cccc(Oc3ccc(C(N)=O)cc3S(=O)(=O)NC(=O)NC(C)(C)C)c2)cc1]<br>(LXXVIII) |

TABLE 1.2-continued

Amide Array: Synthesis of various amides from (LXXV)

| Amine | Amount (mg); Amount (mmol); Yield (mg; %) | Target Compound |
|---|---|---|
| morpholine (HN-morpholine) | 20.97; 0.2407; 31 mg; 34% | (LXXIX) |
| H$_2$N-CH$_2$CH$_2$-OCH$_3$ | 18.08; 0.2407; 63 mg; 71% | (LXXX) |

TABLE 1.2-continued

Amide Array: Synthesis of various amides from (LXXV)

| Amine | Amount (mg); Amount (mmol); Yield (mg; %) | Target Compound |
|---|---|---|
| H$_2$N-CH$_2$CH$_2$-N(CH$_3$)$_2$ | 21.22; 0.2407; 33 mg; 36% | (LXXXI) |
| H$_2$N-CH$_2$-cyclopropyl | 17.12; 0.2407; 59 mg; 66% | (LXXXII) |

TABLE 1.2-continued

Amide Array: Synthesis of various amides from (LXXV)

| Amine | Amount (mg); Amount (mmol); Yield (mg; %) | Target Compound |
|---|---|---|
| HN⟨azetidine⟩ | 13.74; 0.2407; 12.8 mg; 15% & 23 mg; 27% | (LXXXIII) |
| H₂N–phenyl | 22.42; 0.2407; 28 mg; 30% | (LXXXIV) |

TABLE 1.2-continued
Amide Array: Synthesis of various amides from (LXXV)
| Amine | Amount (mg); Amount (mmol); Yield (mg; %) | Target Compound |
|---|---|---|
| 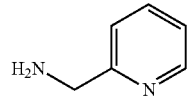 | 26.03; 0.2407; 53 mg; 56% | 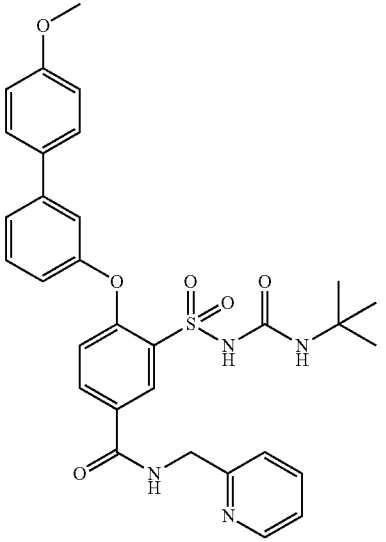<br>(LXXXV) |
| 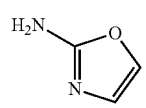 | 20.24; 0.2407; 16.5 mg; 19% | 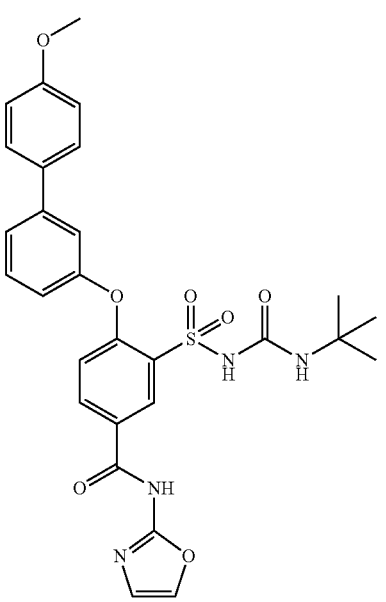<br>(LXXXVI) |

TABLE 1.2-continued

Amide Array: Synthesis of various amides from (LXXV)

| Amine | Amount (mg);<br>Amount (mmol);<br>Yield (mg; %) | Target Compound |
|---|---|---|
| ![azetidine amine] H₂N-azetidine-O | 17.59;<br>0.2407; 49<br>mg; 55% | (LXXXVII) |

Generic methods of amide coupling are described.

For each of the target reactions (e.g., Pathway W and Table 2.1), the amine (0.2407 mmol), HATU (114.3 mg, 0.301 mmol) and Hunigs base (167.4 µL) were successively added to a solution of the acid 20 (80 mg, 0.16046 mmol) in DMF (1.5 mL). The resulting mixture was stirred at room temperature for 18 hours. The DMF was removed under high vacuum and the residue was partitioned between EtOAc (20 mL) and H₂O (10 mL). The aqueous phase was acidified using concentrated HCl (to pH ~2) and extracted with EtOAc (2×20 mL). The combined organics were dried over MgSO₄, filtered and evaporated to dryness under vacuum. The crude products were re-dissolved in DMSO (1.5 mL), filtered and then purified by preparative HPLC to yield the desired products with formulas (LXXVI), (LXXXII), (LXXVIII), (LXXIX), (LXXX), (LXXXI), (LXXXII), (LXXXIII), (LXXXIV), (LXXXV), (LXXXVI), and (LXXXVII), as shown in Table 2.1.

Pathway X, below, shows the synthesis of N-(tert-butyl-carbamoyl)-5-(3-hydroxyazetidine-1-carbonyl)-2-((4'-methoxy-[1,1'-biphenyl]-3-yl)oxy)benzenesulfonamide, formula (LXXXVIII) from compound formula (LXXV).

PATHWAY X

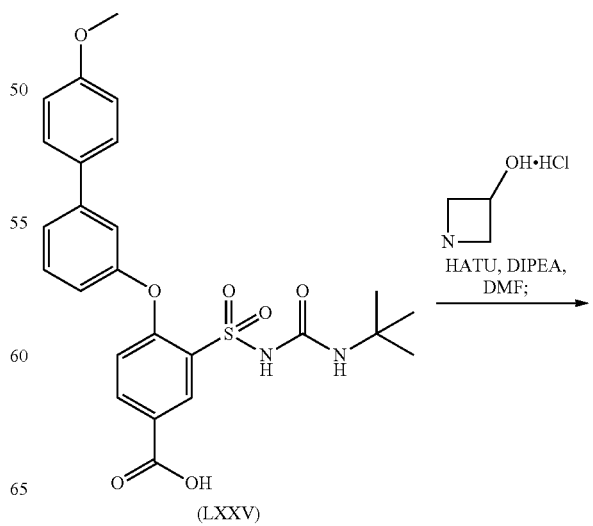

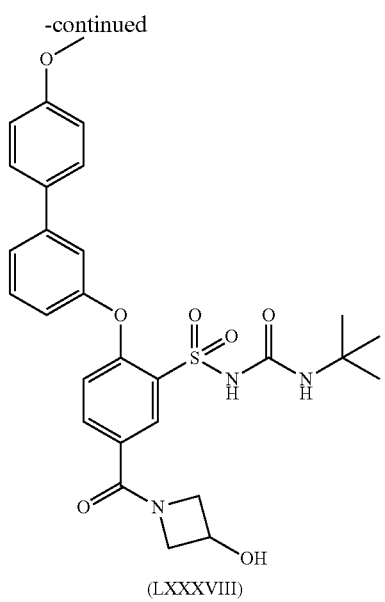

(LXXXVIII)

Azetidin-3-ol hydrochloride (26.4 mg, 0.240 mmol), HATU (67 mg, 0.1767 mmol) and DIPEA (112 μL, 0.642 mmol) were successively added to a solution of acid (Formula (LXXV), 80 mg, 0.161 mmol) in DMF (2 mL). The resulting mixture was stirred at room temperature for 4 hours. The DMF was removed under high vacuum and the residue taken up in EtOAc and H2O. The aqueous phase was acidified using concentrated HCl (to pH ~2) and extracted with EtOAc (2×20 mL). The combined organics were dried over MgSO4, filtered and evaporated to dryness under vacuum. The crude product was dissolved in DMSO (~1.5 mL), filtered and then purified by preparative HPLC to yield the title compound as a white solid (Formula (LXXXVIII), 19.2 mg, 21.5%).

Synthesis of various compounds is now shown.

Synthesis of N-(tert-butylcarbamoyl)-2-chloro-5-(trifluoromethyl)benzene-sulfonamide, formula (XC), from (LXXXIX) is shown in Pathway Y.

PATHWAY Y

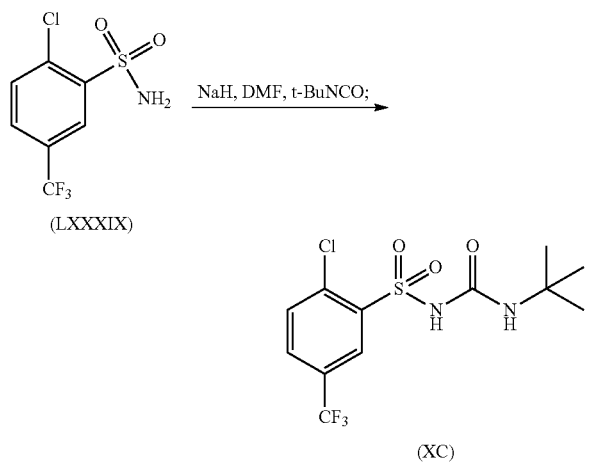

Sodium hydride (60% oil dispersion, 105 mg, 2.6 mmol) was added to a solution of 2-chloro-5-(trifluoromethyl) benzenesulfonamide (Formula (LXXXIX), 612 mg, 2.36 mmol) in DMF (30 mL). The mixture was stirred at room temperature for 10 minutes prior to the addition of tert-butylisocyanate (380 μL, 3.30 mmol). The resulting reaction mixture was stirred overnight at room temperature. The DMF was removed under high vacuum and the crude solid was re-dissolved in EtOAc and H2O, then acidified using 1 N HCl (pH=1). The aqueous phase was extracted with EtOAc and the combined organic phases were dried over MgSO4, filtered and evaporated to dryness under vacuum to yield the desired product (formula (XC)), which was taken to the next step without further purification.

Pathway Z provides N-(tert-butylcarbamoyl)-2-((4'-methoxy-[1,1'-biphenyl]-3-yl)oxy)-5-(trifluoromethyl)benzenesulfonamide, formula (XCI).

PATHWAY Z

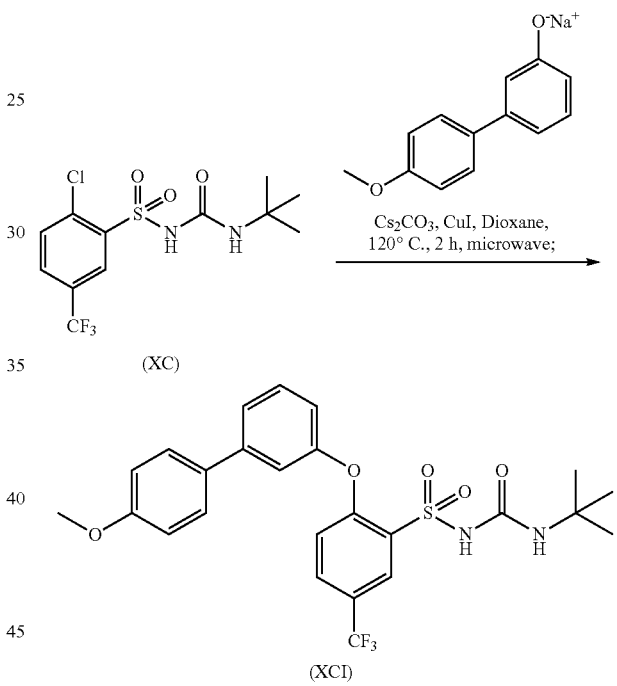

A microwave tube was charged with the sulfonylurea (Formula (XC), 250 mg, 0.7 mmol), the methoxy biphenyl (182 mg, 0.8 mmol), Cs2CO3 (456 mg, 1.39 mmol), CuI (7 mg, 0.036 mmol) and dioxane (1.5 mL). The mixture was heated at 120° C. for 2 hours under microwave irradiation. After cooling to room temperature, the reaction mixture was diluted with EtOAc then water. The reaction was acidified using 1 N HCl to pH 1. The aqueous phase was extracted with EtOAc (×2) and the combined organic phases were dried over MgSO4, filtered and evaporated to dryness. The crude product was dissolved in DMSO (1.5 mL) and then purified by preparative HPLC to yield the desired product as an off white solid (Formula (XCI), 39.1 mg, 11%).

N-(tert-butylcarbamoyl)-2-chloro-5-fluorobenzenesulfonamide, formula (XCIII), is made from (XCII) in Pathway AA.

PATHWAY AA

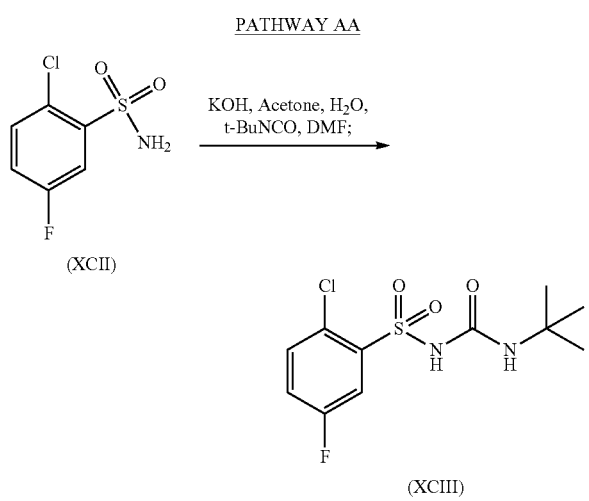

A solution of 2-chloro-5-fluorobenzenesulfonamide (Formula (XCII), 350 mg, 1.69 mmol) in acetone (4 mL) was treated with a solution of potassium hydroxide (95 mg, 1.69 mmol) in H$_2$O (600 µL). The reaction was stirred at room temperature for 15 minutes after which time the solvent was removed under vacuum. The residue was taken up in DMF (4 mL), treated with tert-butylisocyanate (390 µL, 3.39 mmol) and stirred overnight at room temperature. The DMF was removed under high vacuum and the residue was suspended in H$_2$O (5 mL) before addition of 6 N NaOH (5 mL). The reaction was stirred and sonicated, then acidified using 12 N HCl to pH 1. The resulting white solid was collected by filtration, washed with 2 N HCl and dried under suction on a sinter. The solid was dissolved in EtOAc (50 mL) and the combined organic phases were dried over MgSO$_4$, filtered and evaporated to dryness to yield the desired product (Formula (XCIII), 520 mg, 100% yield).

N-(tert-butylcarbamoyl)-5-fluoro-2-((4'-methoxy-[1,1'-biphenyl]-3-yl)oxy)benzene-sulfonamide, formula (XCIV), is prepared from (XCIII) in Pathway AB.

PATHWAY AB

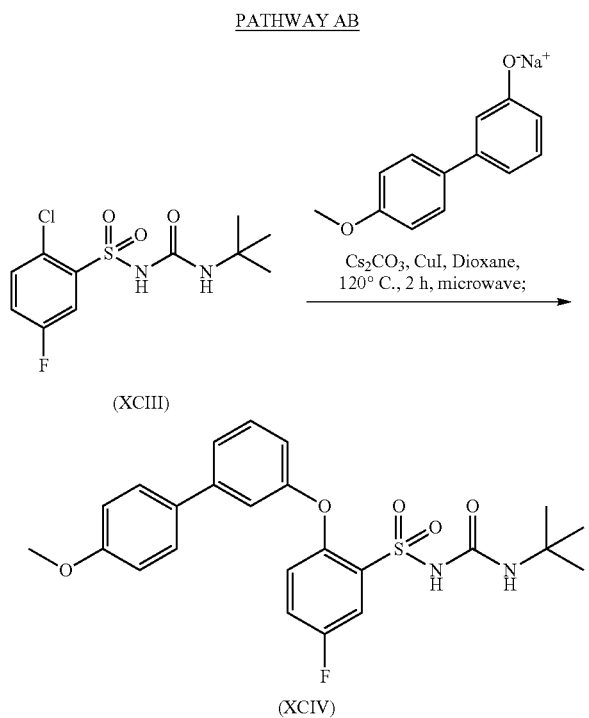

A microwave tube was charged with the sulfonylurea represented by formula (XCIII), 171 mg, 0.55 mmol), the methoxy biphenyl (6, 145 mg, 0.72 mmol), Cs$_2$CO$_3$ (360 mg, 1.1 mmol), CuI (6 mg, 0.031 mmol) and dioxane (1.5 mL). The mixture was heated at 120° C. for 2 hours under microwave irradiation. After returning to room temperature, the reaction mixture was diluted with EtOAc and water. The aqueous phase was acidified using 1 N HCl to pH 1 and then separated, re-extracting with EtOAc (×2). The combined organic phases were dried over MgSO$_4$, filtered and evaporated to dryness under vacuum. The crude product was dissolved in DMSO (1.5 mL) and then purified by preparative HPLC to yield the desired product (Formula (XCIV), 3 mg, 9%).

Pathway AC shows preparation of 2-chloro-5-(methylsulfonyl)benzenesulfonamide, Formula (XCVI) from (XCV).

PATHWAY AC

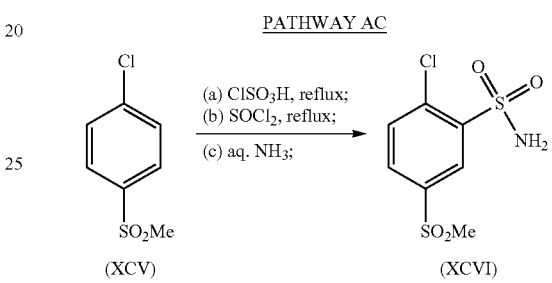

To chlorosulphonic acid (25 mL) cooled on an ice-salt bath, 4-chloro-1-methylsulphonylbenzene (Formula (XCV), 5 g, 26.2 mmol) was carefully added and the mixture was heated to reflux (160° C.) for 1 hour. The reaction was cooled to room temperature and then SOCl$_2$ (1.5 mL) was added. The mixture was heated to reflux for a further 2 hours and then allowed to cool to room temperature before pouring onto ice under stirring. A precipitate was collected by filtration and washed with cold water. The solid was then added to a solution of NH$_4$OH (150 mL, 10% w/v) and stirred overnight at room temperature. The reaction was acidified to pH 4-5 using concentrated HCl and the resulting solid was collected and dried. The crude product was dissolved with the aid of sonication in EtOAc (100 mL) and then dried over magnesium sulfate and filtered before concentrating to dryness under vacuum to yield the desired product as an off white solid (Formula (XCVI), 360 mg, 5.1%). The 2-chloro-5-(methylsulfonyl)benzenesulfonamide (XCVI) was taken on to the next step without further purification.

In Pathway AD, N-(tert-butylcarbamoyl)-2-chloro-5-(methylsulfonyl)benzene-sulfonamide, Formula (XCVIII) is made from (XCVII).

PATHWAY AD

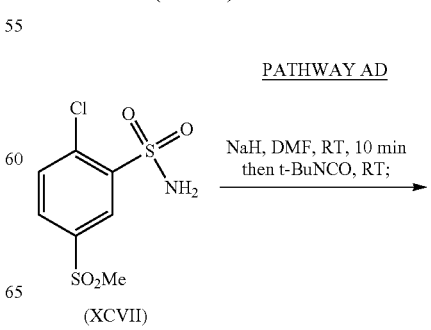

-continued

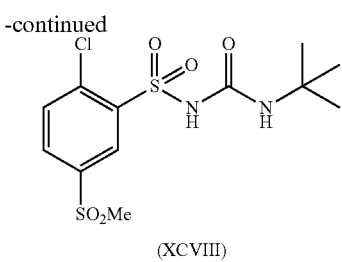

(XCVIII)

Sodium hydride (60% in oil dispersion, 60 mg, 1.46 mmol) was added to a solution of 2-chloro-5-(methylsulfonyl)benzenesulfonamide (33, 360 mg, 1.33 mmol) in DMF (10 mL) at room temperature. The mixture was stirred at room temperature for 15 minutes before tert-butylisocyanate (212 µL, 1.862 mmol) was added. The resulting mixture was stirred overnight at room temperature. The reaction was quenched with water and then the DMF was removed under high vacuum. The residue was diluted with EtOAc and H$_2$O, then acidified using 1 N HCl to pH 1. The product was extracted with EtOAc and the combined organic phases were washed with brine, dried over MgSO$_4$, filtered and evaporated to dryness. The crude product was sonicated for 10 minutes with DCM/MeOH (1:1, 40 mL), then filtered to yield as a white solid (Formula (XCVIII), 0.3 g, 56%) which was used in, e.g., Pathway AE, without further purification.

Pathway AE synthesizes N-(tert-butylcarbamoyl)-2-((4'-methoxy-[1,1'-biphenyl]-3-yl)oxy)-5-(methylsulfonyl)benzenesulfonamide, Formula (XCIX) from (XCVIII).

PATHWAY AE

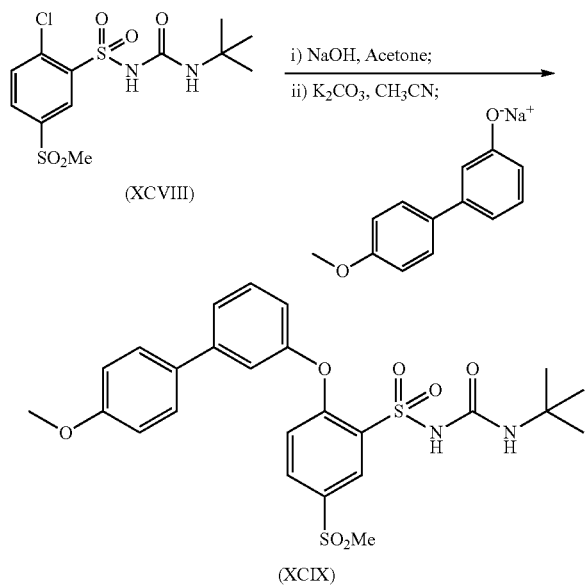

(XCIX)

An aqueous solution of NaOH (10% w/v, 80 mg; 2.0 mmol) was added to a solution of the phenol (6, 366 mg; 1.82 mmol) in acetone (10 mL). The solvents were removed under vacuum to afford the sodium salt, which was added to a solution of sulfonamide (34, 135 mg g; 0.367 mmol) in acetonitrile (20 mL). The mixture was heated to reflux and then potassium carbonate (35 mg, 0.257 mmol) was added, maintaining this temperature for 18 hours. The solvents were removed under vacuum and the residue was re-dissolved in DMSO (1.5 mL) and then purified by preparative HPLC to yield an off-white solid (Formula (XCIX), 57 mg, 29%).

The synthesis of modified nitriles is shown.

In Pathway AF, 5-bromo-2-((4'-methoxy-[1,1'-biphenyl]-3-yl)oxy)-4-methyl-benzene-sulfonamide, formula (CI), is synthesized from Formula (C).

PATHWAY AF

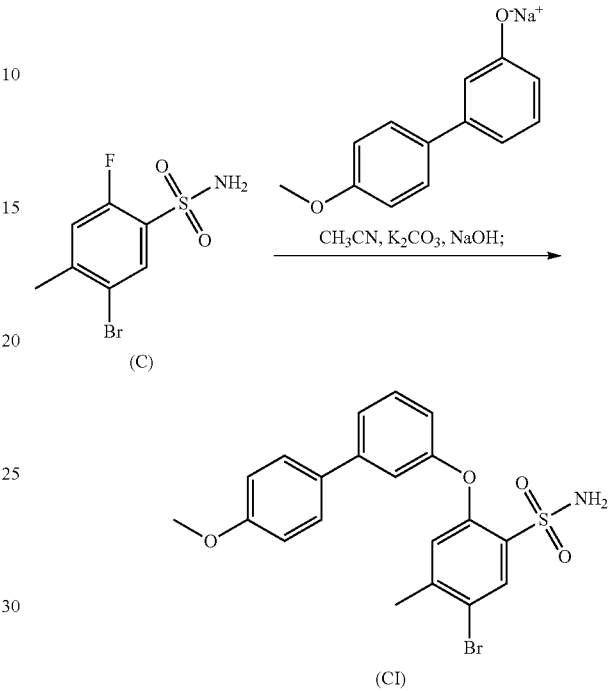

(CI)

A 10% w/v aqueous solution of NaOH (10.23 mmol) was added to a solution of phenol (1.12 g, 5.58 mmol) in acetone (50 mL). The reaction was evaporated under reduced pressure to afford the sodium salt. The 5-bromo-2 fluoro-4-methylbenzene sulfonamide (Formula (C), 0.5 g, 1.86 mmol) was dissolved in acetonitrile (20 mL) and added to the sodium salt, dissolved in acetonitrile (30 mL). The resulting reaction mixture was heated to reflux. Potassium carbonate (180 mg, 1.302 mmol) was added after 30 minutes and the reaction left to reflux for 18 hours, after which time LC-MS analysis showed starting material only. The reaction mixture was then heated in the microwave for 4 hours at 140° C., after which time LC-MS analysis showed approximately 25% conversion. The acetonitrile was removed under reduced pressure and the residue was taken up in ethyl acetate/H$_2$O. The aqueous layer was acidified using concentrated HCl (pH=1) and the organics were separated and the aqueous re-extracted with ethyl acetate (×2). The combined organics were dried and evaporated to give a brown oil (~2 g). The oil was re-dissolved in DCM and loaded onto 100 g Biotage silica cartridge and purified by Biotage chromatography (eluting with iso-hexane/ethyl acetate, gradient 20-80%). The fractions containing product were combined and evaporated to give an orange oil (~0.6 g). LC-MS analysis showed 77.4% purity, and therefore, the oil was re-purified by loading onto 50 g Biotage silica cartridge and purified by Biotage chromatography (eluting with iso-hexane/ethyl acetate, gradient 0-50%) and dried to give the final product (Formula (CI), 361 mg).

In Pathway AG, 5-cyano-2-((4'-methoxy-[1,1'-biphenyl]-3-yl)oxy)-4-methylbenzenesulfonamide, Formula (CII), is prepared.

PATHWAY AG

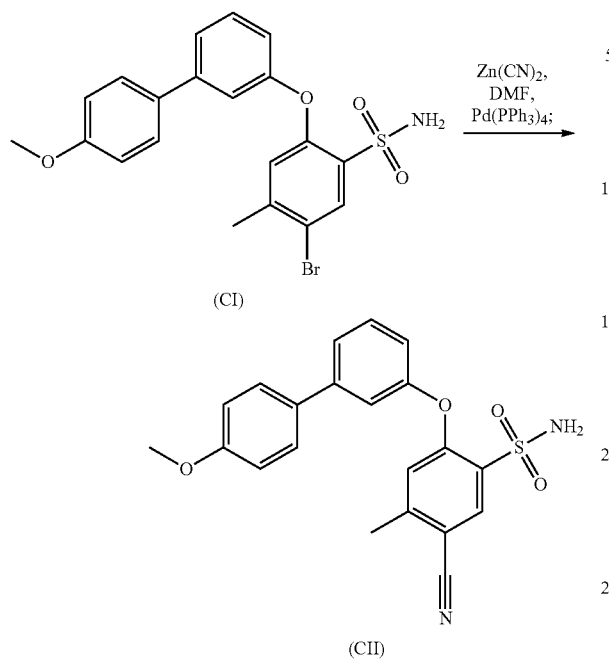

The sulfonamide (Formula (CI), 480 mg, 1.071 mmol) was dissolved in DMF (4 mL) and Zn(CN)$_2$ (189 mg, 1.606 mmol) was added. The reaction mixture was flushed with nitrogen before the addition of Pd(PPh$_3$)$_4$ (124 mg, 0.107 mmol). The vial was sealed and heated to 80° C. for 72 hours. The solid was filtered off and the DMF removed under high vacuum. The resulting crude solid was taken up in DCM and H$_2$O and the organics separated, dried and evaporated to give a pale yellow oil (~550 mg). The oil was dissolved in DCM and loaded onto 50 g Biotage silica cartridge and purified using Biotage chromatography (eluting with iso-hexane/ethyl acetate, gradient 20-75%) and the product containing fractions were concentrated to dryness under vacuum to give an off white solid (Formula (CII), 175 mg, 41.4%).

Pathway AH produces N-(tert-butylcarbamoyl)-5-cyano-2-((4'-methoxy-[1,1'-biphenyl]-3-yl)oxy)-4-methyl benzenesulfonamide, Formula (LVIII), from (CII).

PATHWAY AH

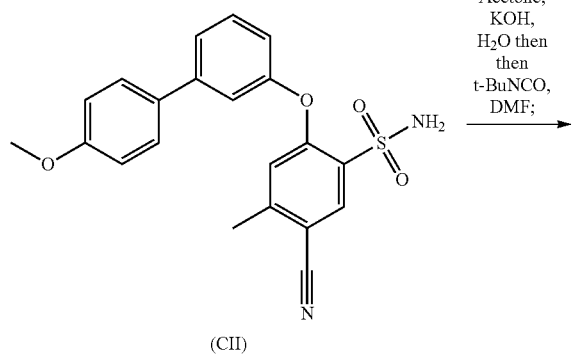

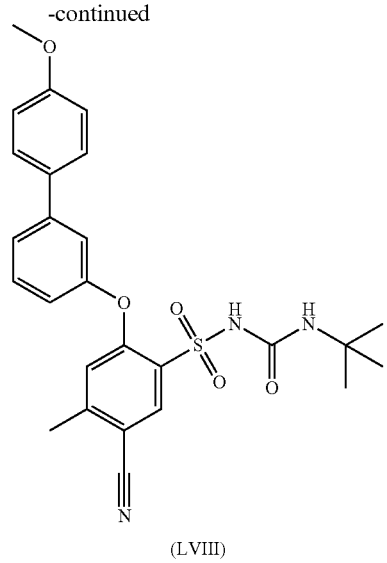

A solution of the sulfonamide (Formula (CII), 175 mg, 0.444 mmol) in acetone (2 mL) was treated with a solution of KOH (24.9 mg, 0.444 mmol) in H$_2$O (100 µL). The reaction was stirred at room temperature for 30 minutes. The solvent was removed under high vacuum and the resulting residue was dissolved in DMF (2 mL). tert-Butylisocyanate (101 µL, 0.888 mmol) was added and the reaction was stirred for 18 hours at room temperature. The reaction mixture was evaporated to dryness under high vacuum and the residue re-dissolved in mixture of MeOH and DCM and loaded on to silica. The crude product was purified by Biotage chromatography on a 50 g Biotage Silica cartridge (elution with iso-hexane/ethyl acetate, gradient 0-75%), then triturated with diethyl ether/iso-hexane and dried under vacuum to give as a white solid (Formula (LVIII), 131 mg, 60%).

In Pathway AI, 5-bromo-2-((4'-methoxy-[1,1'-biphenyl]-3-yl)oxy)pyridine-3-sulfonamide, Formula (CIV), is made.

PAHTWAY AI

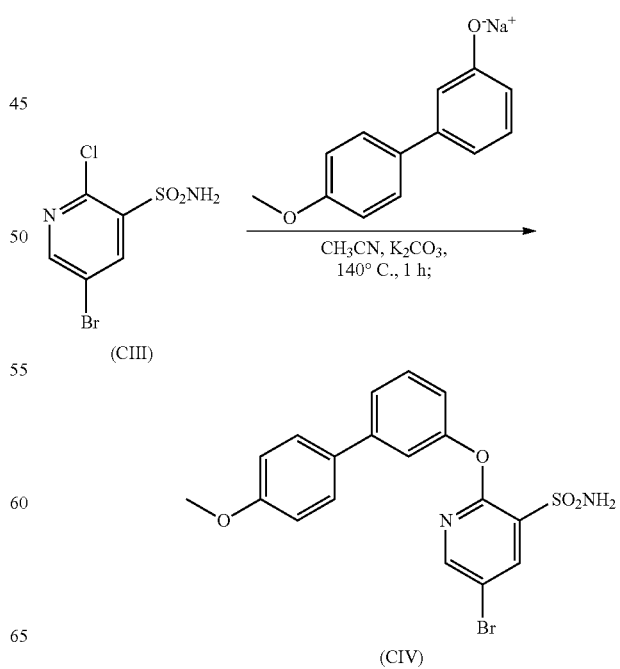

A solution of 5-bromo-2-chloropyridine-3-sulfonamide (Formula (CIII), 1 g, 3.63 mmol) and the methoxy biphenol (1.45 g, 7.26 mmol) in acetonitrile (40 mL) was heated at reflux overnight in the presence of $K_2CO_3$ (1.03 g, 7.260 mmol). LC-MS showed ~40% conversion. The reaction mixture was then heated to 140° C. for 1 hour, after which time LC-MS showed complete conversion. The solvents were removed under vacuum and the residue was diluted with water, and then extracted with DCM (50 mL). The organic phases were combined, dried over $MgSO_4$ and then concentrated to dryness directly onto silica. The crude product was purified by Biotage chromatography using a 100 g Biotage silica cartridge (eluting with iso-hexane/ EtOAc, gradient 0 to 50%) and the product containing fractions were concentrated to dryness under vacuum to give as a white solid (Formula (CIV), 0.92 g, 58%) which was used directly in the next step without further purification.

Using Pathway AJ, (CV) as a reactant yields 5-cyano-2-((4'-methoxy-[1,1'-biphenyl]-3-yl)oxy)pyridine-3-sulfonamide, Formula (CVI).

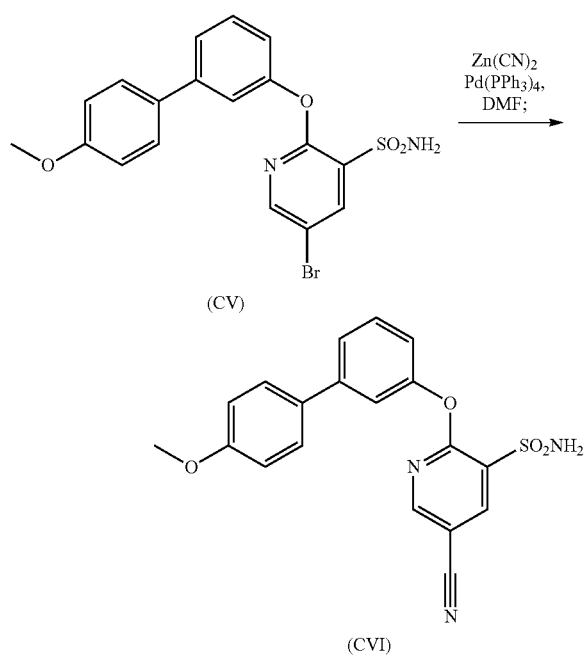

The pyridine sulfonamide (Formula (CV), 250 mg, 0.575 mmol), $Zn(CN)_2$ (101 mg, 0.862 mmol), $Pd(PPh_3)_4$ (66 mg, 0.0575 mmol) and DMF (3 mL) were charged to a stem tube. The mixture was de-oxygenated by purging with nitrogen and then sealed under nitrogen. The reaction was heated to 80° C. for 72 hours. The solvents were removed under vacuum, loading directly onto silica before purification by Biotage chromatography (50 g cartridge, eluting with DCM/ MeOH gradient 0-5%). The product containing fractions were concentrated to dryness under vacuum to give a solid that was triturated with diethyl ether (4 mL), filtered and then dried to provide as a white powder (Formula (CVI), 160 mg, 73%).

To prepare N-(tert-butylcarbamoyl)-5-cyano-2-((4'-methoxy-[1,1'-biphenyl]-3-yl)oxy)benzene-sulfonamide, Formula (LIX), from (CVI), Pathway AK is used.

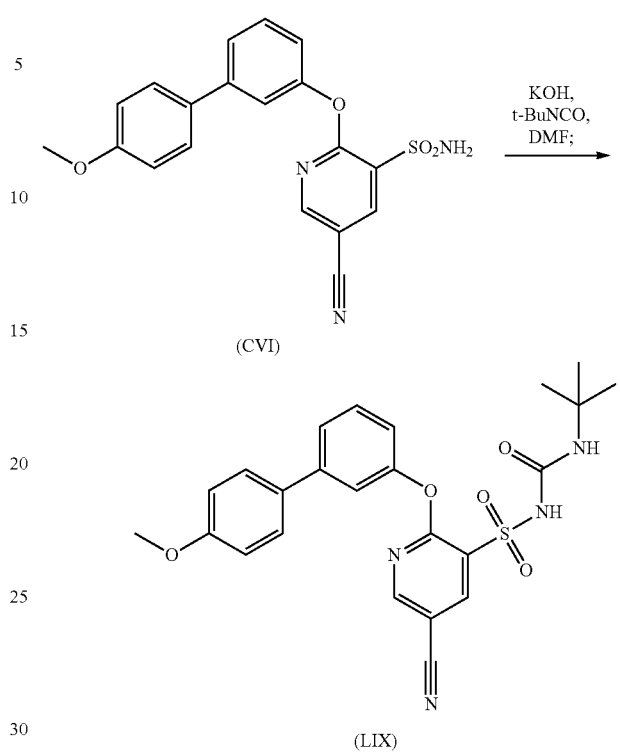

KOH (33 mg, 0.5879 mmol) in water (0.4 mL) was added to a solution of the pyridine sulphonamide (Formula (CVI), 160 mg, 0.412 mmol) in acetone (8 mL). The mixture was stirred for 2 minutes and then concentrated to dryness under vacuum. The residue was dissolved in DMF (1 mL) before the addition of tert-butylisocyanate (96 μL, 0.840 mmol) and stirred for 3 hours. The reaction was concentrated to dryness. The crude product was re-dissolved in a mixture of DCM/ MeOH and then loaded onto silica. The crude product was purified by Biotage chromatography (50 g cartridge, eluting with DCM/MeOH, gradient 0-5%). The product fractions were combined and concentrated to dryness to give as an off-white solid (Formula (LIX), 149 mg, 74%).

Synthesis of a pyridyl compound is described.

In Pathway AL, 4-((4'-methoxy-[1,1'-biphenyl]-3-yl)oxy) pyridine-3-sulfonamide, formula (CVIII) is made.

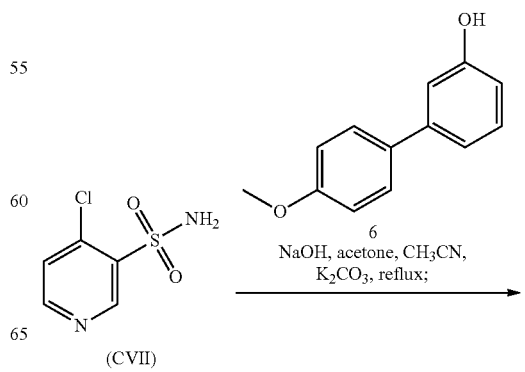

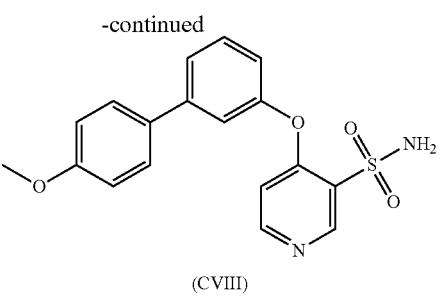

(CVIII)

For pathway AL, an aqueous solution of NaOH (330 mg, 8.25 mmol, 10% w/v,) was added to a solution of the 4'-methoxy-[1,1'-biphenyl]-3-ol (1.5 g, 7.5 mmol) in acetone (45 mL). The solvents were removed by evaporation to afford the sodium salt which was added to a solution of the 4-chloropyridine-3-sulfonamide (Formula (CVII), 723 mg, 1.5 mmol) in MeCN (45 mL). The reaction mixture was heated under reflux for 1 hour. The reaction was cooled, $K_2CO_3$ (364 mg, 2.63 mmol) was added and the reaction heated to reflux for 72 hours. A solid product was obtained when DCM (50 mL) and $H_2O$ (30 mL) were added. The crude product was collected by filtration, washed with aqueous 10% $K_2CO_3$ (4×10 mL) to yield the target compound (Formula (CVIII)) which may be taken through to Pathway AM without further purification.

Pathway AM shows the preparation of N-(tert-butylcarbamoyl)-4-((4'-methoxy-[1,1'-biphenyl]-3-yl)oxy)pyridine-3-sulfonamide, represented by formula (LVII).

PATHWAY AM

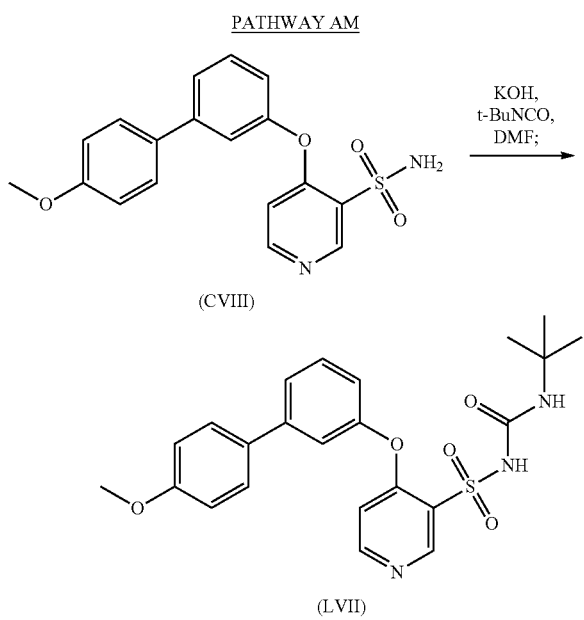

The pyridine sulfonamide (Formula (CVIII), 150 mg, 0.42 mmol) was dissolved in acetone (2 mL) before adding a solution of KOH (33.3 mg, 0.59 mmol) in $H_2O$ (0.6 mL) and was then stirred for 20 minutes. The solvent was removed under vacuum and the residue was re-dissolved in DMF (2 mL). tert-Butylisocyanate (135 μL, 0.84 mmol) was added and the reaction mixture was stirred overnight at room temperature. The reaction mixture was evaporated to dryness under reduced pressure. The residue was dissolved in DMSO (~1.5 mL) and purified by preparative HPLC to yield the title compound as a white solid (Formula (LVII), 37 mg, 40%).

The N-oxide of Formula (LVII) can be synthesized according to Pathway AN, i.e., producing 3-(N-(tert-butylcarbamoyl)sulfamoyl)-4-((4'-methoxy-[1,1'-biphenyl]-3-yl)oxy)pyridine 1-oxide, Formula (LX).

PATHWAY AN

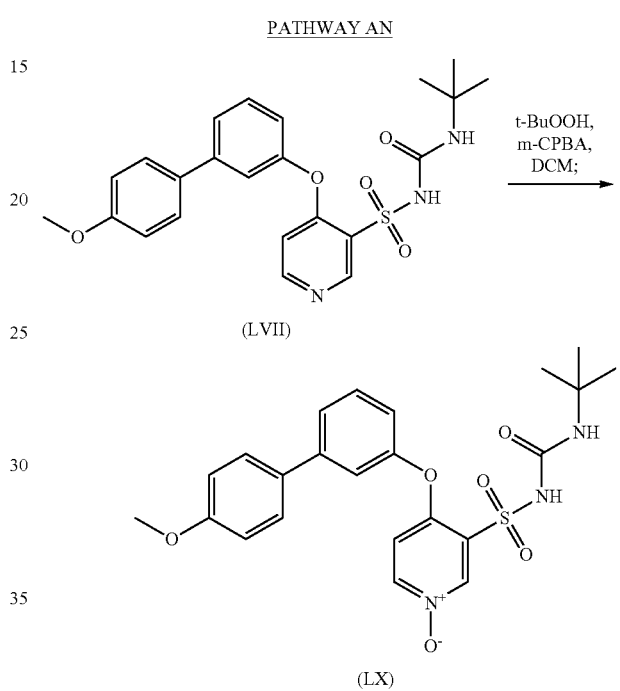

In Pathway AN, tert-butylperoxide (12 μL, 0.0594 mmol) was added to a solution of pyridyl (Formula (LVII), 16 mg, 0.0396 mmol) in DCM (1 mL) and the reaction was stirred for 18 hours. LC-MS analysis showed no conversion. A further aliquot of tert-butylperoxide (24 μL, 0.119 mmol) was added and after a further 4 hours of stirring there was still no reaction, as confirmed by LC-MS. m-CPBA (15 mg, 0.0869 mmol) was added and the reaction was stirred for 18 hours. LC-MS analysis confirmed complete conversion to the desired product. The solvents were removed under vacuum and the crude product was re-dissolved in DMF (1.5 mL) and then purified by preparative HPLC to give the desired product (Formula LX, 6.8 mg, 36%).

The foregoing pathways are illustrative of possible ways to prepare compounds of the invention and are not limiting. Using pathways such as those described above, compounds of the invention can be synthesized, such as those described by the formulas (LII), (LXXV), (XCI), (LXII), (LXXIV), (LXIII), (LXI), (XCIV), (LXX), (LXXVI), (LXXXV), (LXXXVII), (LXXVIII), (LXXX), (LXXXI), (LXXXII), (LXXXIII), (LXIV), (LXV), (LXVI), (LXVII), (LXXIX), (LXXXVIII), (LXXXVI), (LXXXIV), (CIX), (XCIX), (LXXVII), (LXVIII), (CX), (LVH), (LVIII), (LIX), and (LX).

85
(LII)
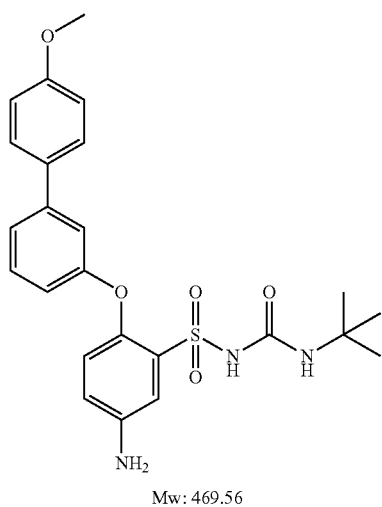
Mw: 469.56
(LXXV)
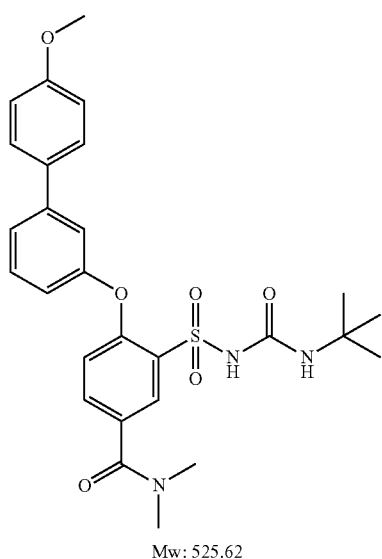
Mw: 525.62
(XCI)
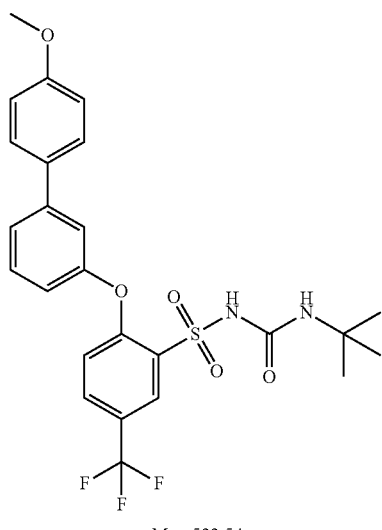
Mw: 522.54
86
-continued
(LXII)
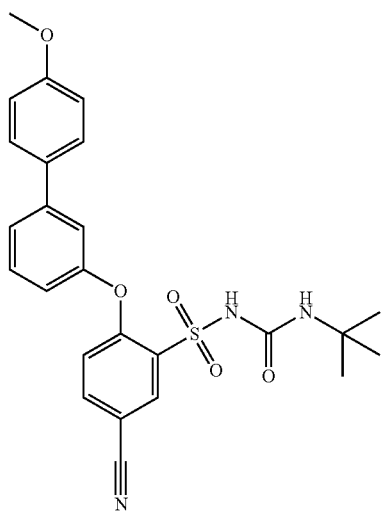
Mw: 479.55
(LXXIV)
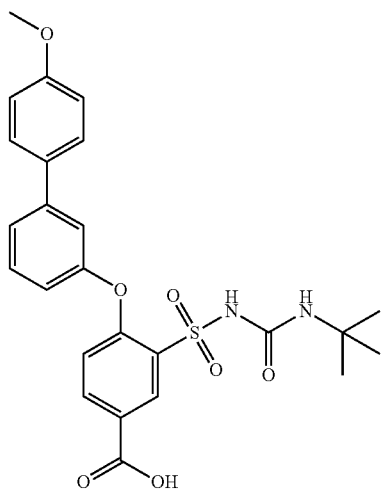
Mw: 498.55
(LXIII)
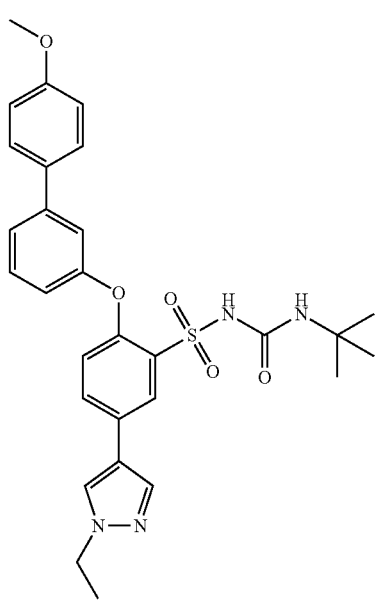
Mw: 548.66

87
-continued
(LXI)
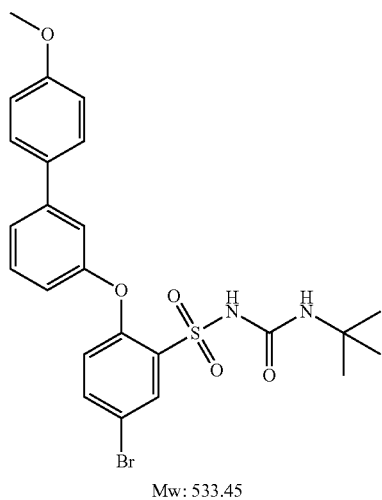
Mw: 533.45
(XCIV)
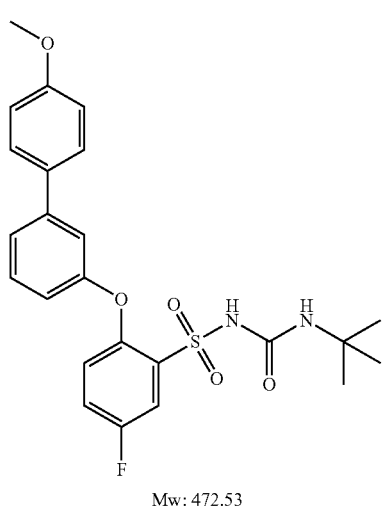
Mw: 472.53
(LXX)
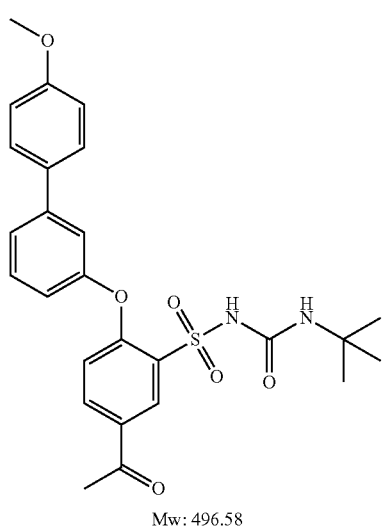
Mw: 496.58
88
-continued
(LXXVI)
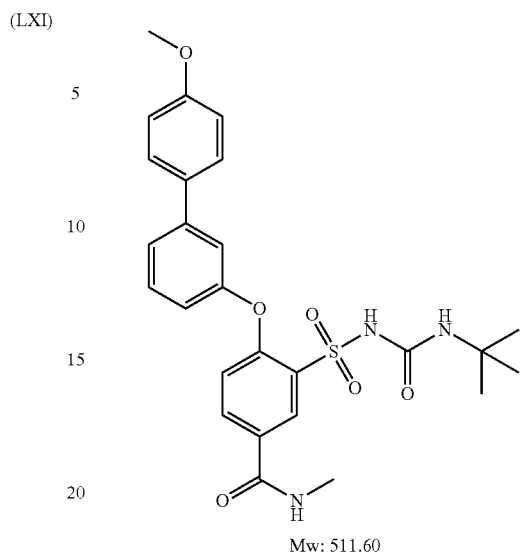
Mw: 511.60
(LXXXV)
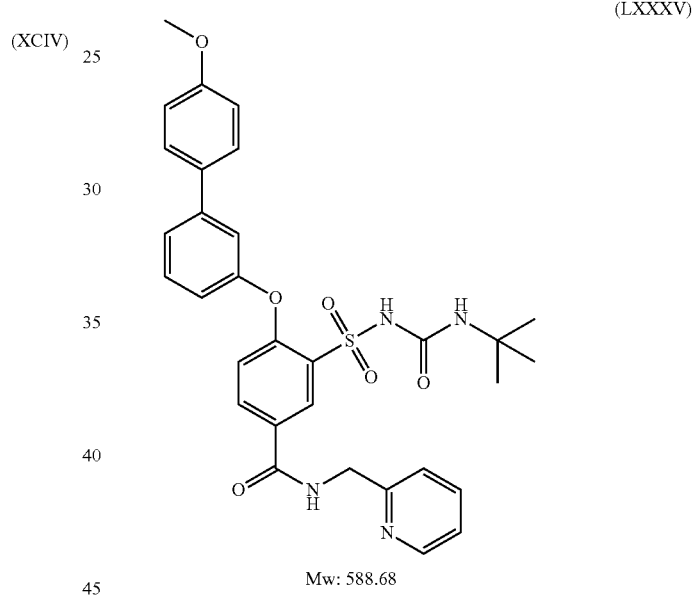
Mw: 588.68
(LXXXVII)
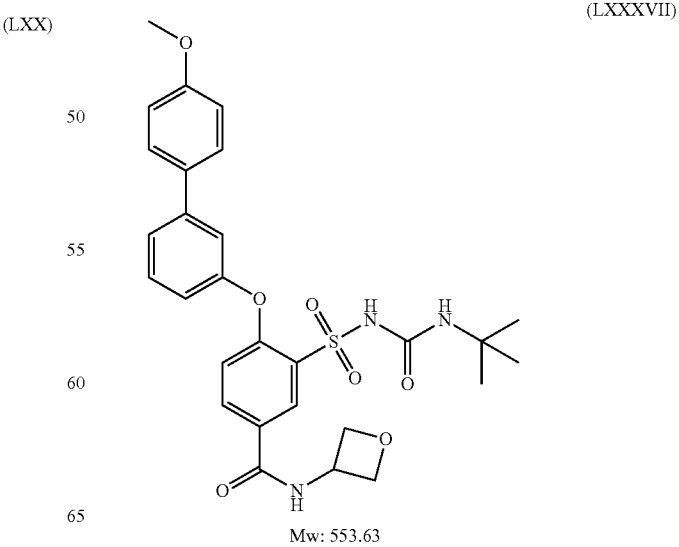
Mw: 553.63

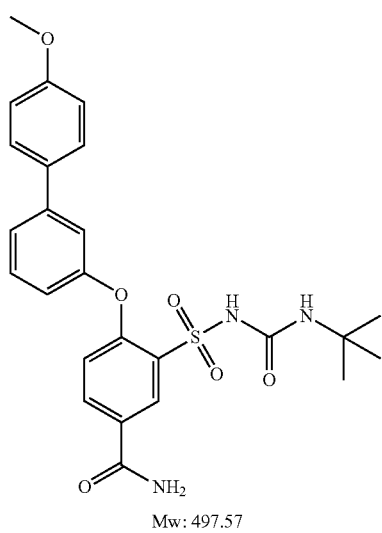
(LXXVIII)
Mw: 497.57
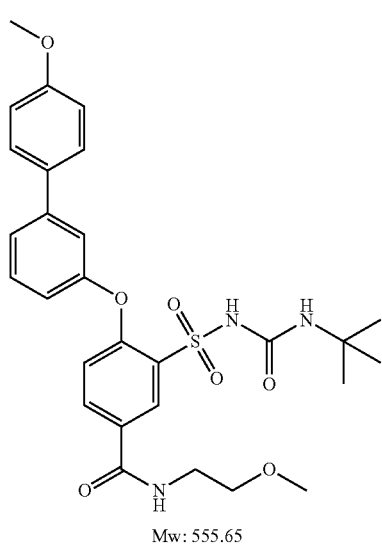
(LXXX)
Mw: 555.65
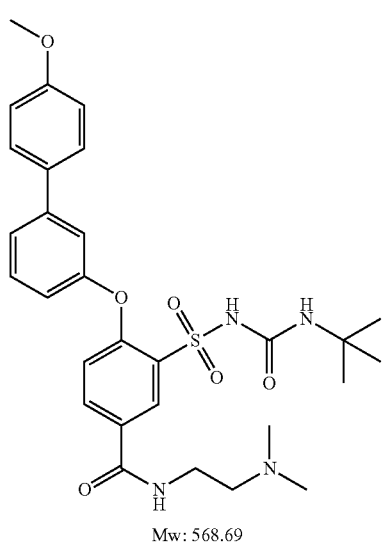
(LXXXI)
Mw: 568.69
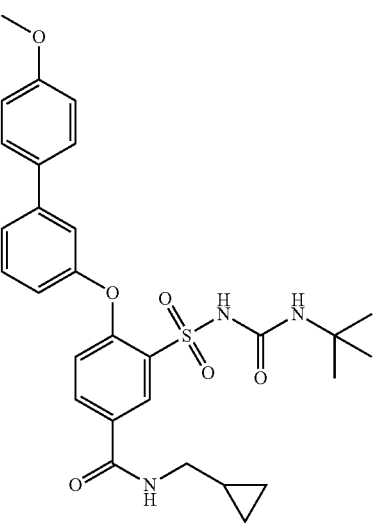
(LXXXII)
Mw: 551.66
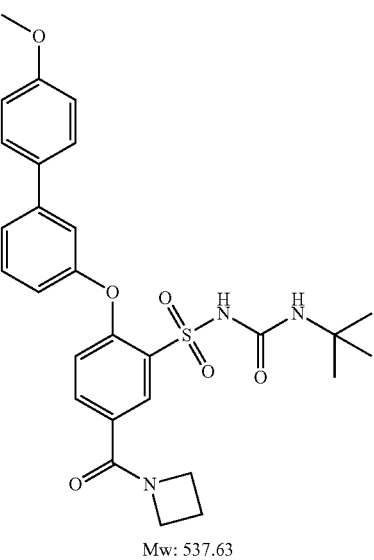
(LXXXIII)
Mw: 537.63
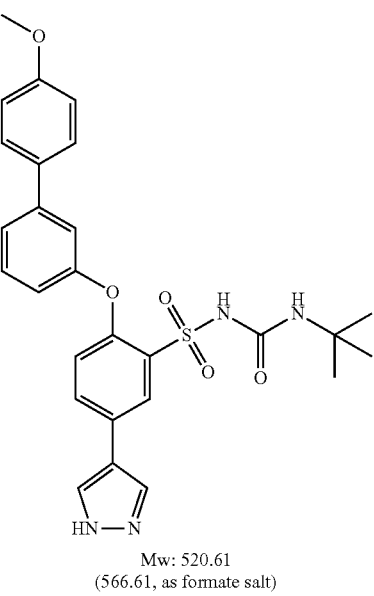
(LXIV)
Mw: 520.61
(566.61, as formate salt)

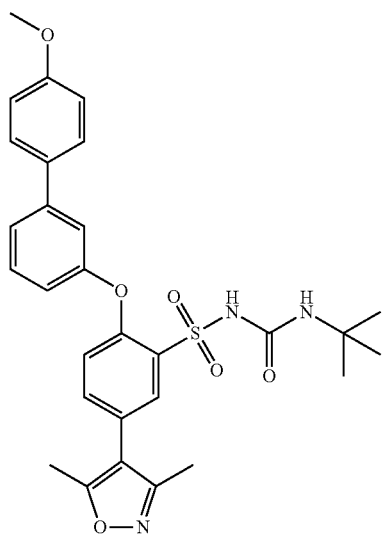
(LXV)
Mw: 549.65
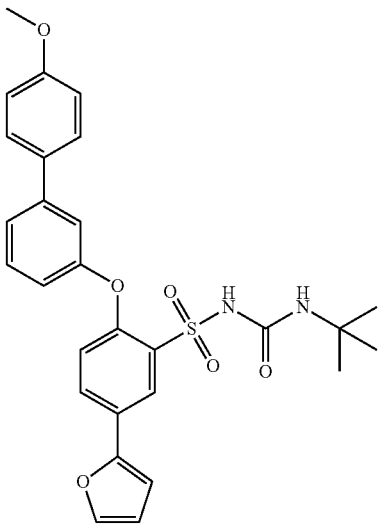
(LXVII)
Mw: 520.60
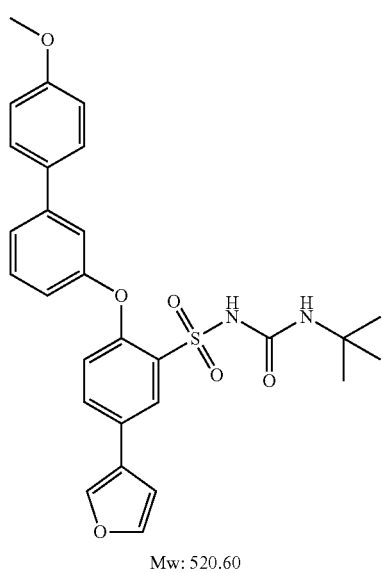
(LXVI)
Mw: 520.60
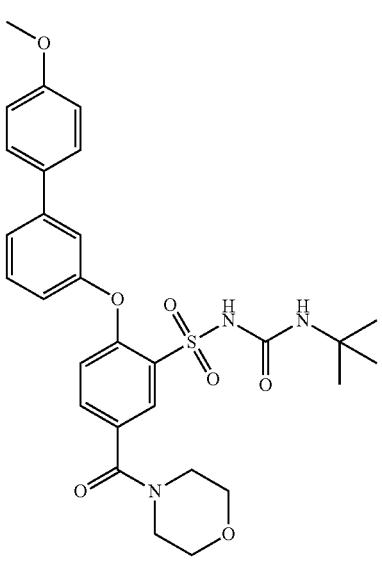
(LXXIX)
Mw: 567.66

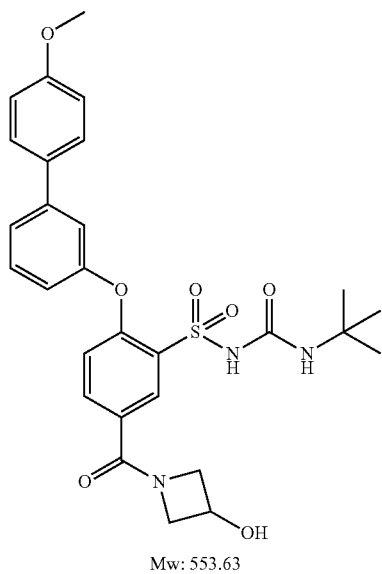
(LXXXVIII)
Mw: 553.63
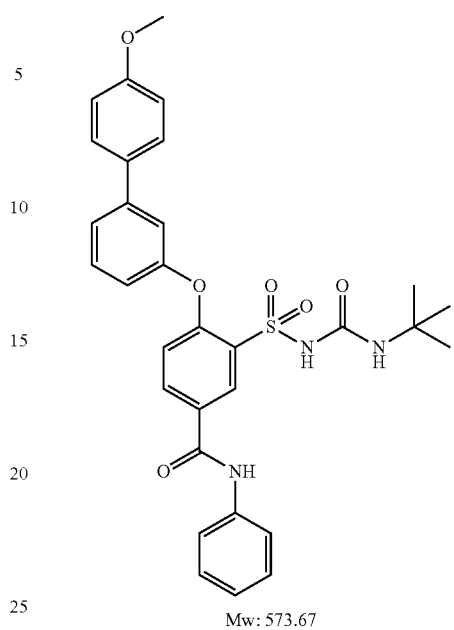
(LXXXIV)
Mw: 573.67
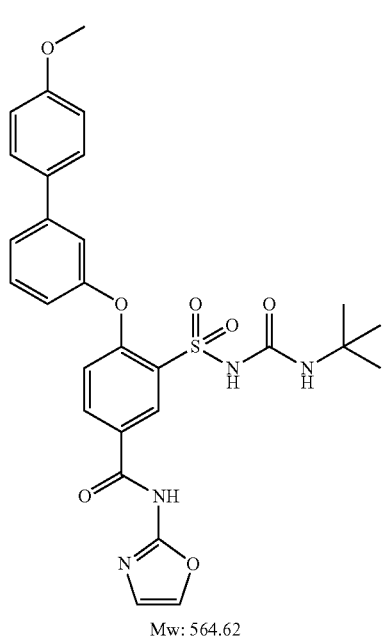
(LXXXIV)
Mw: 564.62
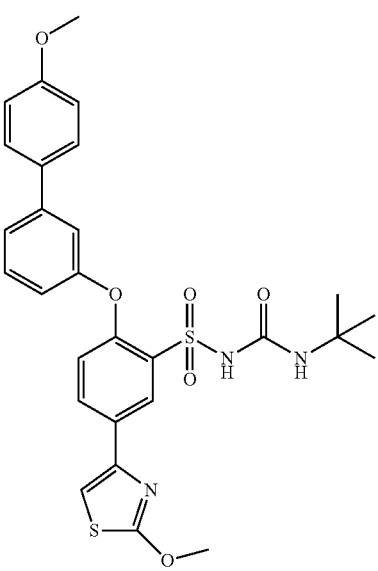
(CIX)
Mw: 567.68

95
-continued
(XCIX)
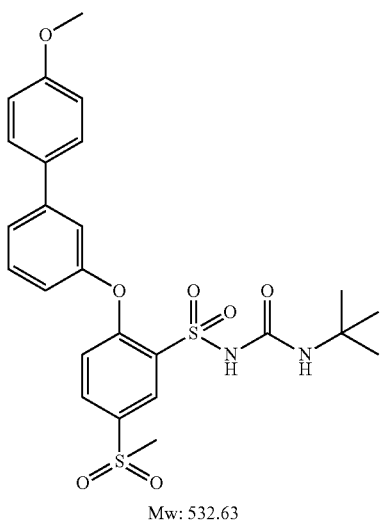
Mw: 532.63
(LXXVII)
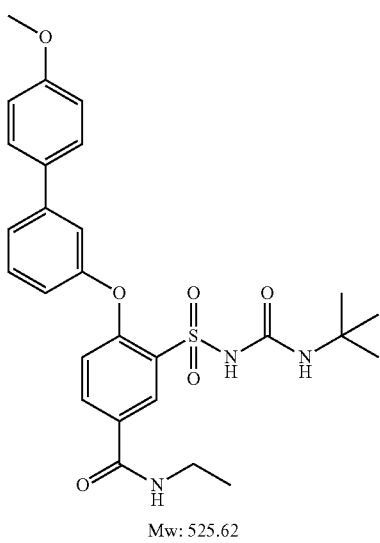
Mw: 525.62
(LXVIII)
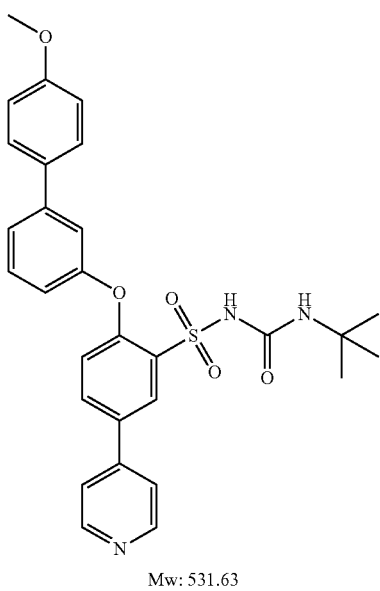
Mw: 531.63
96
-continued
(CX)
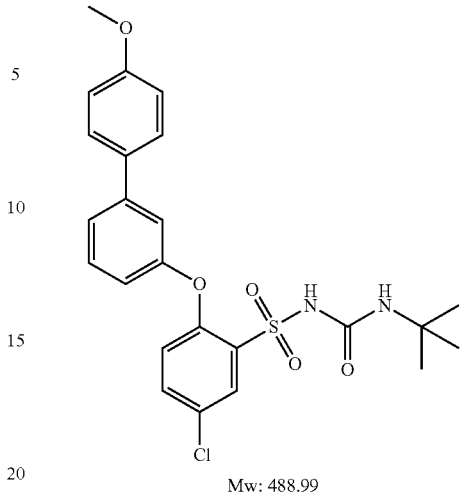
Mw: 488.99
(LVII)
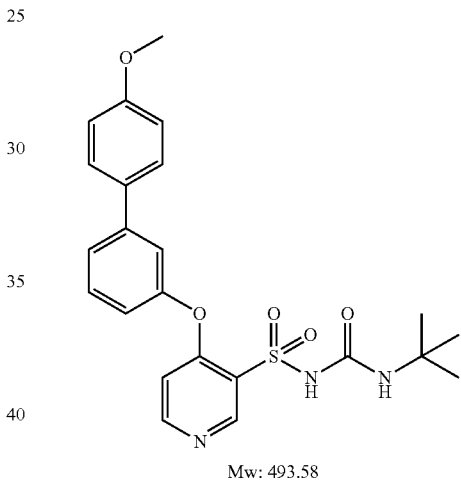
Mw: 493.58
(LVIII)
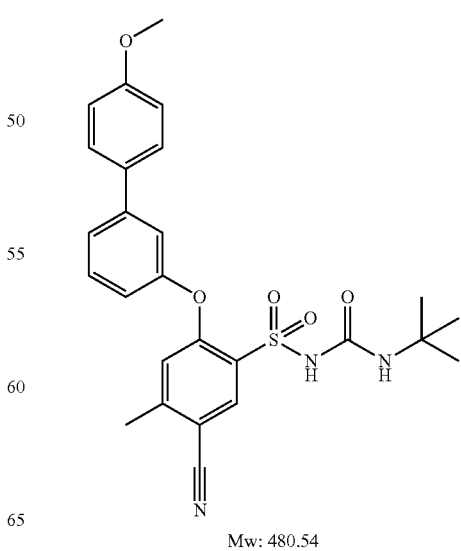
Mw: 480.54

(LIX)

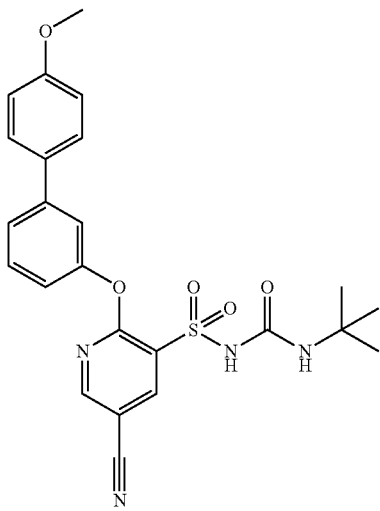

Mw: 479.55

(LX)

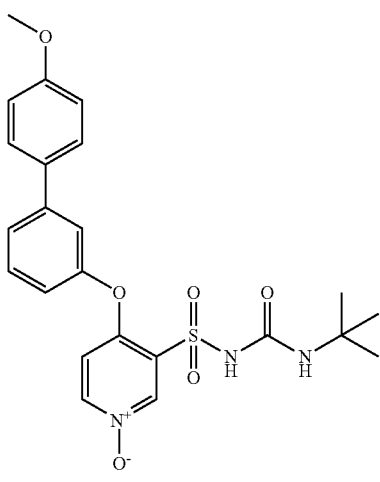

Mw: 471.53

Compounds of the invention can be in a pharmaceutically acceptable salt form or as the free base. Suitable routes of administration include oral, buccal, topical (including transdermal), injection, intravenous, nasal, pulmonary, and with or on an implantable medical device (e.g., stent or drug-eluting stent or balloon equivalents).

In some embodiments, compounds of the invention prevent dampening of the immune system which is mediated by elevated levels of TXA2. Efficient immune activation is important in retarding cancer development and tumor cell eradication. Compounds of the invention will function synergistically with immune-modulating drugs and with oncolytic viruses in retarding and eradicating tumor cells.

The effective dosage of each agent can readily be determined by a skilled person, having regard to typical factors such as the age, weight, sex and clinical history of the patient. A typical dosage could be, for example, 1-1,000 mg/kg, preferably 5-500 mg/kg per day, or less than about 5 mg/kg, for example administered once per day, every other day, every few days, once a week, once every two weeks, or once a month, or a limited number of times, such as just once, twice or three or more times.

A pharmaceutical composition containing each active ingredient may be in a form suitable for oral use, for example, as tablets, troches, lozenges, fast-melts, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874, to form osmotic therapeutic tablets for control release. Preparation and administration of compounds is discussed in U.S. Pat. No. 6,214,841 and U.S. Pub. 2003/0232877, incorporate by reference herein in their entirety.

Formulations for oral use may also be presented as hard gelatin capsules in which the active ingredient is mixed with an inert solid diluent, for example calcium carbonate, calcium phosphate or kaolin, or as soft gelatin capsules in which the active ingredient is mixed with water or an oil medium, for example peanut oil, liquid paraffin or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Each active agent, including the inventive compound, may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Examples of such materials are cocoa butter and polyethylene glycols.

For topical use, creams, ointments, jellies, fast melt tablets, solutions or suspensions are suitable as are nebulized forms for pulmonary delivery. Topical application includes the use of mouth washes and gargles.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Calcium Mobilization

An appropriate functional test for the evaluation of the agonistic and/or antagonistic potency of the compounds of the invention is the determination of calcium flux. Both TPα and TPβ are coupled to the G-protein Gαq. Therefore, stimulation of these receptors ultimately leads to a release of intracellular calcium ($[Ca^{2+}]_i$) from intracellular stores. Consequently, the determination of $[Ca^{2+}]_i$ flux represents an appropriate functional test for the evaluation of the agonistic/antagonistic potency of compounds of the invention. Calcium can be measured using a molecule characterized by the covalent combination of a $Ca^{2+}$ chelating group and a fluorophore group. The $Ca^{2+}$ binding properties of these indicators are formed by the presence of a tetracarboxylic acid core as found for example in EGTA (Ethylene Glycol bis(2-aminoethyl)Tetraacetic Acid). Binding of $Ca^{2+}$ produces a wavelength shift in either the excitation or emission fluorescence spectra or a change in the emission intensity. Whereas the $Ca^{2+}$ binding to EGTA is pH dependent, recent dyes are designed from an EGTA derivative, BAPTA (1,2-Bis(2-Aminophenoxy)ethane-N,N,N',N'-Tetraacetic Acid). Loading of these dyes inside cells commonly uses esterified forms (acetoxymethyl ester), which are able to cross the cell membranes and are subsequently hydrolyzed by esterases inside the cell.

Estimation of $[Ca^{2+}]_i$ flux is calculated from the fluorescence signal (F). For calibration, the maximal fluorescence ($F_{max}$, $Ca^{2+}$-saturated form of the dye) as well as minimal fluorescence ($F_{min}$, $Ca^{2+}$-free form of the dye) must be determined. These parameters are determined usually in situ after the experiment, for example by subsequent addition to the mixture of a cell-disrupting agent that releases all $Ca^{2+}$ such as Triton X100 and a potent $Ca^{2+}$-chelating agent such as EGTA. After subtraction of background fluorescence, $[Ca^{2+}]_i$ flux can be calculated for non-ratiometric indicators.

Intracellular $[Ca^{2+}]_i$ fluxes were measured using a fluorescence plate reader following a modified protocol of Kassack et al., 'Quantitative comparison of functional screening by measuring intracellular $Ca^{2+}$ with radioligand binding at recombinant human dopamine receptors', AAPS Pharmsci, 2002, 4(4); 102-111, in cell lines (e.g. HEK293 or other cell type) endogenously-expressing or over-expressing either TPα, TPβ or any other receptor or protein to be screened.

By way of example, HEK 293 cells which have been grown for 3-4 days in normal growth media (minimum essential media containing 10% FBS and 2 mmol/l L-glutamine), under normal growth conditions (37° C., in humidified 5% $CO_2$ atmosphere) are washed and harvested in KREBs-HEPES buffer (118 mM NaCl, 4.7 mM KCl, 1.2 mM MgSO₄, 1.2 mM KH₂PO₄, 4.2 mM NaHCO₃, 11.7 mM D-glucose, 1.3 mM CaCl₂, 10 mM HEPES, pH 7.4). Cells are then incubated with 3 μM Fluo-4 in KREBs-HEPES buffer containing 1% Pluoronic F-127, for 1 hr at 25° C. with agitation. Then, cells are washed in KREBs-HEPES buffer containing 0.5% BSA and re-suspended at a final concentration of $3 \times 10^5$ cells/ml. Approx. $5.4 \times 10^4$ cells per well are plated in a 96-well plate and pre-incubated with test compounds for 10 m prior to measuring the fluorescence intensity at 520 nm for 25 seconds at 1 s intervals to monitor baseline using the Fluoroskan Ascent. Agonist (e.g., 1 μM U46619) is injected into separate wells by the automatic pipettor and fluorescence intensity is monitored at 520 nm for 75 seconds at 1 s intervals. Thereafter, Triton X100 and EGTA are added sequentially where $F_{max}$ refers to maximal fluorescence intensity measured after permeabilization of the cells with 2% Triton X100 and $F_{min}$ refers to fluorescence intensity measured after addition of 1 mM EGTA. Changes in mobilization of intracellular [Ca²⁺] concentration are calculated as follows:

$$\Delta[Ca^{2+}]_i(nM) = Kd \times (F - F_{min})/(F_{max} - F)$$

where an equilibrium constant (Kd) of 345 nM is used for Fluo-4.

The dye Fluo-4 has its excitation peak at 480 nm, in the visible spectra, which spare cells to be damaged by UV (340-360 nm) stimulation and reduces auto-fluorescence of cells. It is not necessary to determine the precise $[Ca^{2+}]_i$, but rather variations in concentrations.

The method allows the detection of $[Ca^{2+}]_i$ mobilization upon stimulation by U46619 in human TP platelets. Similarly, the $[Ca^{2+}]_i$ mobilization in response to U46619 stimulation (1 μM) in the HEK293 cell lines is assessed. Both TPα and TPβ transfected cells responded in a comparable fashion. The $[Ca^{2+}]_i$ mobilization in response to other agonists in HEK 293 and other cell types either endogenously-expressing or over-expressing other receptors or proteins is assessed.

As reference compounds for screening assays, compounds 9h and 9ag, previously described by Dogne and Hanson et al., (Hanson, J. S., S. Rolin, et al. (2005) *JPET* 313(1):293-301; Hanson et al. (2006) *J Med Chem* 49(12):3701-3709; Hanson et al. (2007) *J Med Chem* 50(16):3928-3936), or SQ29,548, previously described by Ogletree, M. L., Harris, D. N., Greenberg, R., et al. Pharmacological actions of SQ 29,548, a novel selective thromboxane antagonist. *J Pharmacol Exp Ther* 234 435-441 (1985), were used. SQ29,548 and compound 9ag is commercially available from Cayman (CAY10535) while compound 9h was synthesized based on published methodology.

TABLE 1

Reference Compounds

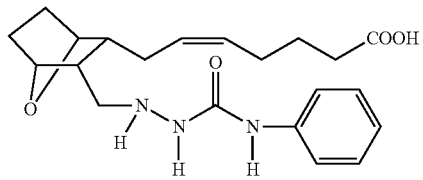 [SMILES: O=C(O)CCC/C=C\CC1C2CCC(O2)C1CNNC(=O)Nc1ccccc1]

SQ29,548

TABLE 1-continued

Reference Compounds

Compound 9h

Compound 9ag

Selected reference compounds (e.g. SQ29,548, 9h or 9ag) and all compounds of the invention were tested for their ability to inhibit $[Ca^{2+}]_i$ mobilization induced by U46619 (1 μM) in a concentration-dependent manner. Examples of calculated IC₅₀ values (concentration able to inhibit 50% of $[Ca^{2+}]_i$ mobilization), obtained for certain reference or invention compounds when tested in HEK293 cells stably over-expressing TPα (HEK.TPα cells) or TPβ (HEK.TPβ cells) are given in Table 2. When such effects of the selected reference and compounds of the invention were tested for antagonism of agonist (U46619)-induced $[Ca^{2+}]_i$ mobilization by the TPα and TPβ isoforms, a selectivity ratio was also determined as the IC₅₀ TPα/IC₅₀ TPβ. Results collected in this evaluation are presented in Table 2.

TABLE 2

Effect of TP antagonists on U46619-induced calcium mobilization in HEK.TPα & HEK.TPβ cell lines.

| TP Antagonist | IC₅₀ data for U46619-mediated [Ca²⁺]ᵢ mobilization (nM) | | TPα:TPβ Selectivity Ratio |
|---|---|---|---|
| | TPα | TPβ | |
| Compound 9ag | 1746 | 379 | 4.5 |
| Compound 9h | 612 | 270 | 2.3 |
| XXXVIII | 4006 | 1991 | 2 |
| IX | 11,620 | 1545 | 7.5 |
| XLI | 106 | 16.5 | 6.4 |
| XLIII | 13,020 | 9325 | 1.4 |
| X | 119 | 7.33 | 16.2 |
| XLVI | 114 | 36.5 | 3 |
| XLV | 185.6 | 33.7 | 5.5 |
| XII | 89.8 | 86 | 1 |

Example 2: Ex Vivo Platelet Aggregation

The effects of selected compounds of the invention on agonist-(U46619)-induced platelet aggregation ex vivo was examined.

A modification of the turbidimetric method originally developed by Born & Cross (Born, G. V. and Cross, M. J., The Aggregation of Blood Platelets, J Physiol, 1963, 168: 178-95) is used. The principle is based on the diffraction of the light by particles. When a light beam passes through a suspension of particles, it is diffracted, depending on the number and the size of the particles in suspension.

In the Born & Cross method, a light beam passes through a platelet suspension and the quantity of light is measured by a detector placed after the sample. Upon platelet aggregation, the size of platelet aggregates will increase while the total number of free platelets will decrease. Consequently, less light will be diffracted and the detector will record an increase in light intensity. The aggregometer has been developed based on these concepts. Variations in light transmission recorded by this device reflects the platelet physiology. When an agonist of platelet aggregation is added to a platelet suspension, platelets undergo activation and shape change. This step is characterized by an increase in platelet's apparent volume and thus a decrease of transmitted light. Subsequent platelet aggregation gradually forms aggregates of increasing size. Transmitted light slightly increases until a plateau is reached. The aggregation of platelet can be confirmed after the experiment by visual direct inspection of the test tube.

Preparation of platelet suspension is achieved by blood centrifugation at 160 g for 10 minutes. The PRP is re-centrifuged at 160 g for 10 min to remove contaminating red and white blood cells. The supernatant which is collected contains the platelets rich plasma (PRP). The remaining blood is subsequently centrifuged at 900 g for 15 min in order to retrieve plasma (platelets poor plasma, PPP). PRP is diluted with PPP to reach a final concentration of $150 \times 10^3$ platelets/4 PRP is kept warmed at 37° C. in the aggregometer and the adequate dilution of drug to test is introduced in the sample. Platelet aggregation is induced after 10 minutes incubation. Light transmission (T) is measured throughout the experiment, which is ended 8 minutes after induction of aggregation. Maximal light transmission (Tmax) is determined in the sample without drugs. Minimal light transmission (Tmin) is measured in PRP without inducer.

Percentage of platelet aggregation inhibition reflects the drug potency and is given by the following equation:

$$\% = 100 \times (1 - ((T - T\text{min})/(T\text{max} - T\text{min})))$$

Results are expressed as $IC_{50}$, which is defined as the drug concentration required to inhibit 50% of platelet aggregation. By way of example, the ability of XLI, X, XLVI, XLV and XII compared to the reference compounds is shown in Table 3.

Compounds XLI, X, XLVI, XLV and XII have improved efficacy over the reference compounds (see Table 3 for summary data) previously identified by Hanson et al. (2007) J Med Chem 50(16):3928-3936).

TABLE 3

Effect of TP antagonists on U46619-induced human platelet aggregation ex vivo.

| TP Antagonist | $IC_{50}$ data for inhibition of U46619-induced platelet aggregation (nM) |
|---|---|
| SQ29,548 | 8.33 |
| Compound 9ag | 985 |
| Compound 9h | 513 |
| XLI | 230 |
| X | 4.71 |
| XLVI | 4.12 |
| XLV | 159 |
| XII | 129 |

The method of assessing platelet aggregation also allows evaluation of the effect of the compounds of the invention on platelet aggregation upon stimulation by other agonists, e.g., adenosine diphosphate (ADP) and thrombin. By way of example, the ability of XLI, X, XLVI, XLV and XII to affect ADP and thrombin-induced platelet aggregation of human platelets ex vivo and all compounds of the invention tested did not affect ADP- or Thrombin-induced aggregation.

Example 3: Screening of Compounds

The effects of selected compounds of the invention on agonist-(U46619)-induced platelet aggregation ex vivo was examined.

Figure 1B:
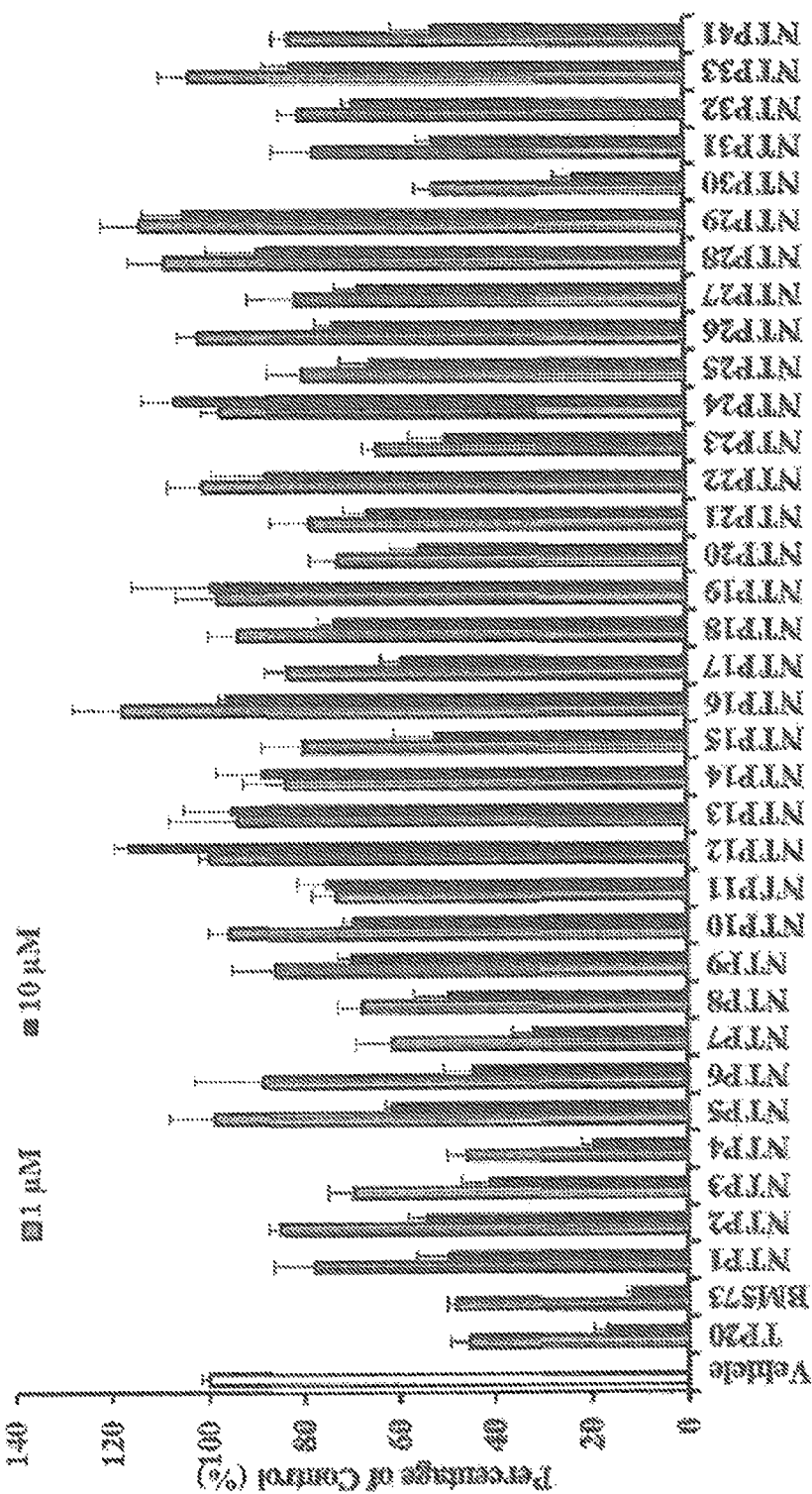

Compounds listed in Table 2.4 were initially screened through calcium mobilisation assays using HEK 293 cells over-expressing the thromboxane (TX) $A_2$ receptor, β isoform (TPβ) referred to as HEK.TPβ cells and thereafter, activity was confirmed in HEK.TPα cells over-expressing the a isoform (TPα). The screening involved examining the effect of the compounds, used at 1 and 10 μM concentrations, on calcium mobilised in response to the $TXA_2$ mimetic U46619 (1 μM). The data was compared to compound Formula (X) (i.e., TP20) and the reference TP antagonist BM573 (1) where the results are shown in FIGS. 1A-1B and Table 2.5 (n≥3). Table 2.4 gives the names used in the study for the compounds by formula reference.

TABLE 2.4

Names in study

| Formula | Name |
|---|---|
| XXI | TP1 |
| XIV | TP2 |
| XV | TP3 |
| XVI | TP4 |
| XVII | TP5 |
| XXIV | TP6 |
| XVIII | TP7 |
| XIX | TP8 |
| XXVI | TP9 |
| III | TP10 |
| VIII | TP11 |
| XXX | TP12 |
| XXXII | TP13 |
| XXXIV | TP14 |
| XXXVI | TP15 |
| XXXVIII | TP16 |
| IX | TP17 |
| XLI | TP18 |
| XLIII | TP19 |
| X | TP20 |
| XLVI | TP21 |

TABLE 2.4-continued

Names in study

| Formula | Name |
|---|---|
| XLVII | TP22 |
| XXV | TP23 |
| XXVII | TP24 |
| XXVIII | TP25 |
| XXIX | TP26 |
| XXXI | TP27 |
| XXXIII | TP29 |
| XXXV | TP30 |
| XXXVII | TP31 |
| XXXIX | TP32 |
| XL | TP33 |
| XLII | TP34 |
| L | TP35 |
| LII | TP36 |
| XLIV | TP37 |
| XLV | TP38 |
| XX | TP39 |
| LIV | TP40 |
| LVI | TP41 |
| XLVIII | TP42 |
| XLIX | TP43 |
| LI | TP44 |
| LIII | TP45 |
| XII | TP46 |
| LV | TP47 |
| XI | TP48 |
| LII | NTP1 |
| LXXV | NTP2 |
| XCI | NTP3 |
| LXII | NTP4 |
| LXXIV | NTP5 |
| LXIII | NTP6 |
| LXI | NTP7 |
| XCIV | NTP8 |
| LXX | NTP9 |
| LXXVI | NTP10 |
| LXXXV | NTP11 |
| LXXXVII | NTP12 |
| LXXVIII | NTP13 |
| LXXX | NTP14 |
| LXXXI | NTP15 |
| LXXXII | NTP16 |
| LXXXIII | NTP17 |
| LXIV | NTP18 |
| LXV | NTP19 |
| LXVI | NTP20 |
| LXVII | NTP21 |
| LXXIX | NTP22 |
| LXXXVIII | NTP23 |
| LXXXVI | NTP24 |
| LXXXIV | NTP25 |
| CIX | NTP26 |
| XCIX | NTP27 |
| LXXVII | NTP28 |
| LXVIII | NTP29 |
| CX | NTP30 |
| LVII | NTP31 |
| LVIII | NTP32 |
| LIX | NTP33 |
| LX | NTP 41 |
| XXIII | Cay10535 |

CONCLUSIONS

Using the definition of activity as an "Antagonist, when used at 1 µM, that leads to greater than 50% inhibition of TP (1 µM U46619)-induced activity (e.g. [$Ca^{2+}$]; mobilization)", a number of compounds were ACTIVE in HEK.TPβ cells, including NTP3 (—$CF_3$), NTP4 (—C≡N), NTP27 (—$SO_2ME$) and the halide variants NTP7 (—Br), NTP8 (—F) & NTP30 (—Cl). Hence, key findings of the SAR that resulted from the synthesis of NTP1-NTP33 & NTP41 are presented here.

In terms of inhibition of TPα/TPβ-induced calcium mobilization in HEK.TPα/HEK.TPβ cell lines, the smaller nitro group replacements, such as —C≡N, the halides (—Br, —Cl & —F), —$CF_3$ and —$SO_2$Me exhibited good ability to antagonize the TPα/TPβ-mediated calcium responses;

A number of other NTP compounds showed limited efficacy in the calcium mobilisation assays in the HEK.TPα/HEK.TPβ cell lines, i.e., ability to inhibit TP-mediated calcium responses, while others showed no affect. Hence, it was possible to group the NTPs into Active and Inactive compounds. With regard to the ACTIVE NTPs, it was also possible to rank them; however, it remains that the smaller substituents are most effective;

NTP4 (—C≡N), when used at 0.1 µM, showed an ability to inhibit TP-mediated platelet aggregation (in response to the TP agonist U46619) in whole blood platelet aggregation assays.

Determination of $IC_{50}$ values of NTP4 in side-by side comparison in (1) the HEK.TPα/HEK.TPβ cell lines and (2) platelets confirmed that while NTP4 is a potent TP antagonist in terms of its ability to inhibit TP-mediated responses.

While NTP4 (—C≡N) is the most active of the nitro replacements synthesized, substitution of the cyanobenzene ring, as in NTP32 (-methyl group) and NTP33 (pyridyl ring), to change the electrophilicity of the cyano group resulted in loss of activity compared to the cyano compound NTP4 and to the key lead TP20.

(1) Calcium Mobilisation Assays: Screening of NTP Compounds in HEK.TPβ & HEK.TPα Cells FIG. 1 shows the effect of the TP antagonist compounds of the invention on U46619-mediated calcium mobilization in HEK.TPα and HEK.TPβ cells. HEK.TPβ (FIG. 1A) and HEK.TPα (FIG. 1B) cells, preloaded with Fluo-4, were incubated with the TP20 (Batch#4), BM573, NTP1-NTP33 and NTP 41 where each antagonist was used at 1 & 10 µM, as indicated, prior to stimulation with 1 µM U46619. Data is presented as the mean (±S.E.M.) percentage of the agonist-induced response in vehicle-treated cells (Percentage of Control; %) and represents data from at least 3 independent experiments were cells were treated in duplicate.

TABLE 2.5

Summary of Calcium Data from Screening Assays.

| TP Antagonist | Percentage of Control (%) | | | |
|---|---|---|---|---|
| | TPα | | TPβ | |
| | 1 µM | 10 µM | 1 µM | 10 µM |
| TP20 | 45.4 ± 4.07 | 17.1 ± 2.46 | 12.6 ± 1.46 | 9.96 ± 1.70 |
| BM573 | 48.5 ± 1.77 | 12.0 ± 0.76 | 23.8 ± 0.68 | 9.90 ± 1.80 |
| NTP1 | 77.8 ± 8.71 | 50.2 ± 6.39 | 101 ± 4.75 | 102 ± 4.15 |
| NTP2 | 85.0 ± 2.71 | 54.9 ± 3.32 | 102 ± 3.59 | 90.1 ± 2.78 |
| NTP3 | 69.6 ± 5.35 | 41.6 ± 5.45 | 46.0 ± 5.92 | 14.8 ± 2.44 |
| NTP4 | 46.1 ± 3.87 | 19.9 ± 2.13 | 22.5 ± 3.70 | 10.2 ± 0.95 |
| NTP5 | 98.7 ± 9.29 | 61.7 ± 1.42 | 88.3 ± 5.27* | 72.0 ± 3.87* |
| NTP6 | 88.6 ± 14.5 | 45.1 ± 5.75 | 94.4 ± 7.70 | 57.4 ± 6.86 |
| NTP7 | 61.5 ± 7.70 | 32.5 ± 3.95 | 49.0 ± 4.41 | 12.2 ± 1.93 |
| NTP8 | 68.0 ± 5.05 | 49.9 ± 6.91 | 59.4 ± 1.85 | 14.6 ± 2.72 |
| NTP9 | 85.9 ± 9.13 | 70.4 ± 2.47 | 46.3 ± 7.33 | 12.2 ± 1.03 |
| NTP10 | 95.5 ± 4.25 | 69.8 ± 1.73 | 96.0 ± 0.94 | 54.7 ± 8.10 |
| NTP11 | 73.1 ± 5.28 | 75.4 ± 5.83 | 49.8 ± 1.86 | 20.7 ± 2.81 |
| NTP12 | 99.7 ± 2.13 | 77.9 ± 2.69 | 84.2 ± 7.51 | 34.4 ± 2.85 |
| NTP13 | 93.8 ± 13.9 | 95.2 ± 9.57 | 74.0 ± 3.66 | 36.2 ± 0.52 |
| NTP14 | 83.5 ± 9.26 | 89.1 ± 9.10 | 86.4 ± 7.06 | 59.4 ± 7.67 |
| NTP15 | 79.8 ± 8.81 | 52.6 ± 8.42 | 87.6 ± 8.28 | 86.1 ± 5.64 |
| NTP16 | 117 ± 10.2 | 96.3 ± 1.24 | 83.0 ± 7.62 | 34.0 ± 3.88 |
| NTP17 | 83.1 ± 4.85 | 59.5 ± 4.07 | 51.1 ± 1.13 | 13.3 ± 5.91 |
| NTP18 | 93.4 ± 6.17 | 73.6 ± 2.98 | 45.0 ± 4.34 | 22.6 ± 2.28 |

TABLE 2.5-continued

Summary of Calcium Data from Screening Assays.

| TP Antagonist | Percentage of Control (%) | | | |
|---|---|---|---|---|
| | TPα | | TPβ | |
| | 1 μM | 10 μM | 1 μM | 10 μM |
| NTP19 | 97.6 ± 8.60 | 99.4 ± 16.0 | 77.7 ± 3.24 | 64.5 ± 4.65 |
| NTP20 | 72.4 ± 5.97 | 55.7 ± 5.84 | 42.5 ± 2.32 | 18.5 ± 3.53 |
| NTP21 | 78.3 ± 8.28 | 66.4 ± 4.95 | 51.0 ± 1.62 | 32.2 ± 2.89 |
| NTP22 | 101 ± 7.28 | 87.6 ± 11.3 | 85.1 ± 4.38 | 50.1 ± 4.06 |
| NTP23 | 64.2 ± 2.89 | 49.9 ± 7.61 | 48.4 ± 2.75 | 20.4 ± 1.94 |
| NTP24 | 96.8 ± 3.94 | 107 ± 6.48 | 87.7 ± 8.18 | 37.9 ± 2.61 |
| NTP25 | 80.0 ± 7.15 | 65.5 ± 6.32 | 61.6 ± 1.93 | 14.8 ± 2.03 |
| NTP26 | 101 ± 4.30 | 73.7 ± 3.56 | 68.6 ± 3.30 | 41.0 ± 3.88 |
| NTP27 | 81.1 ± 10.2 | 68.4 ± 4.56 | 36.4 ± 3.80 | 16.3 ± 2.39 |
| NTP28 | 108 ± 7.64 | 89.5 ± 10.3 | 110 ± 1.85 | 62.3 ± 4.30 |
| NTP29 | 113 ± 8.15 | 105 ± 8.03 | 100 ± 4.69 | 94.6 ± 3.58 |
| NTP30 | 52.2 ± 3.90 | 23.3 ± 3.63 | 46.5 ± 5.86 | 9.31 ± 1.57 |
| NTP31 | 77.3 ± 8.72 | 52.7 ± 2.89 | 74.8 ± 5.49 | 27.7 ± 4.21 |
| NTP32 | 80.3 ± 4.21 | 69.3 ± 2.07 | 93.6 ± 4.06 | 46.2 ± 4.83 |
| NTP33 | 103 ± 6.25 | 82.4 ± 5.86 | 75.6 ± 6.46 | 34.5 ± 1.56 |
| NTP41 | 82.6 ± 3.41 | 52.8 ± 8.03 | 72.2 ± 5.66 | 18.8 ± 1.77 |

Note that reference compound BM573 is shown by Formula (CXI). Also see Rolin, S., Dogne, J. M., Michaux, C., Delarge, J., and Masereel, B. (2001) Prostaglandins Leukot Essent Fatty Acids 65, 67-72.

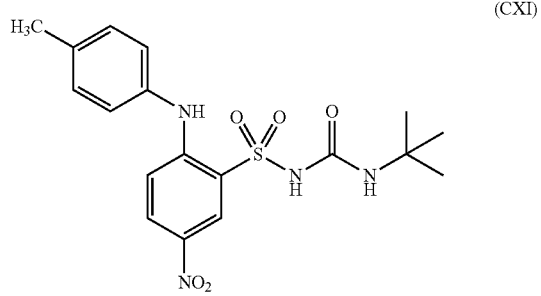 [SMILES: Cc1ccc(Nc2ccc([N+](=O)[O-])cc2S(=O)(=O)NC(=O)NC(C)(C)C)cc1]

(CXI)

TP20 has been identified as a key lead compound. Consistent with this, at 1 & 10 μM concentrations, TP20 potently inhibited U46619-mediated calcium mobilization in HEK.TPβ cells, where responses were reduced by approx. 90%. Likewise, the reference compound BM573, potently inhibited U46619-mediated responses at the concentrations tested. Of the NTP compounds NTP1-NTP33 & NTP41, a number showed good antagonist activity, including NTP3 and NTP4.

Active compounds that showed ≥50% inhibition of U46619-mediated responses in HEK.TPβ cells were subject to further characterization through both calcium and platelet aggregation assays. These compounds include NTP3 (—CF3), NTP4 (—C≡N), NTP7 (—Br), NTP8 (—F), NTP9 (—COMe), NTP11 (amide), NTP17 (amide), NTP18 (C-linked palladium chemistry), NTP20 (C-linked palladium chemistry), NTP21 (C-linked palladium chemistry), NTP23 (amide), NTP25 (amide) and NTP27 (—SO2Me).

Initially, the ability of the selected ACTIVE compounds listed above to inhibit U46619-mediated calcium responses in HEK.TPβ cells was examined, where the concentration were reduced to 0.5 μM and 1 μM, such that the compounds could be ranked in terms of activity.

Figure 2:
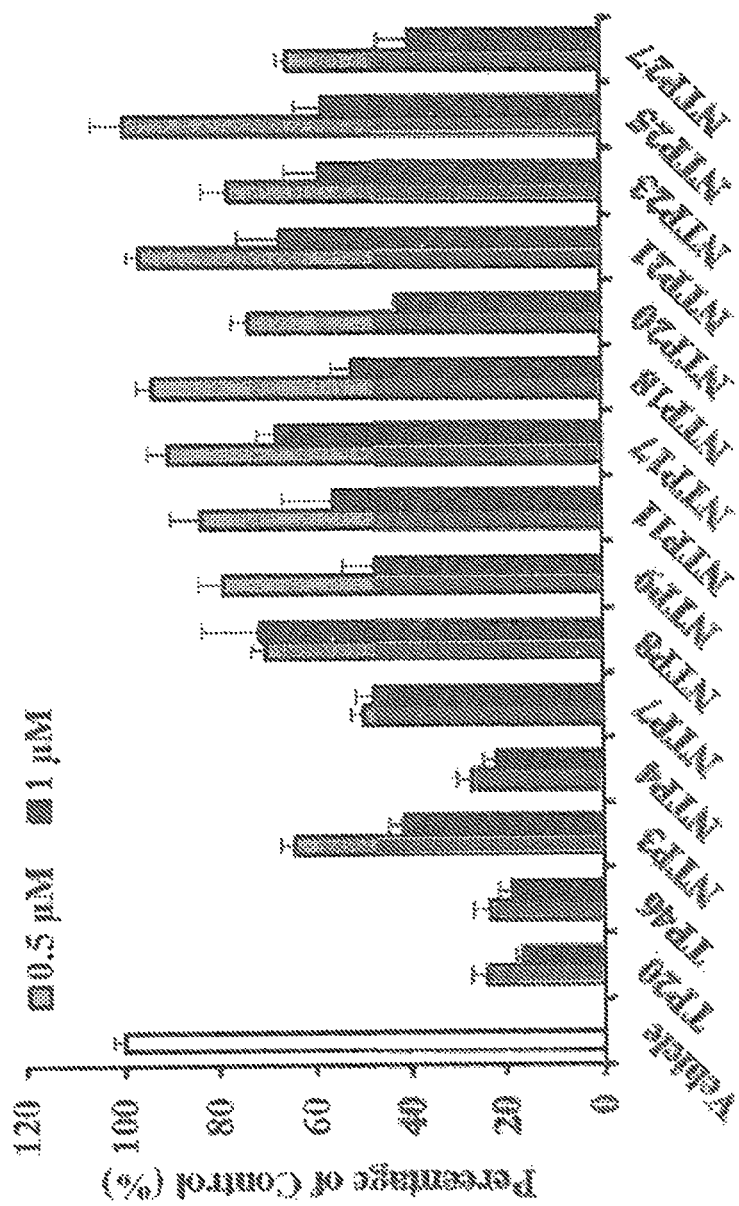
FIG. 2 shows the effect of the TP antagonists on U46619-mediated calcium mobilization in HEK.TPβ cells.

FIG. 2 shows the effect of the TP antagonists on U46619-mediated calcium mobilization in HEK.TPβ cells. HEK.TPβ cells, preloaded with Fluo-4, were incubated with the TP20 and the selected ACTIVE NTP compounds, where each antagonist was used at 0.5 or 1 μM, as indicated, prior to stimulation with 1 μM U46619. Data is presented as the mean (±S.E.M.) percentage of the agonist-induced response in vehicle-treated cells (Percentage of Control; %) and represents data from 4 independent experiments were cells were treated in duplicate.

The selected NTP compounds were ranked based on the data from the calcium responses in HEK.TPβ cells where cells were treated with 0.5 μM of the compound. The compounds, in order in decreasing potency, include NTP4>NTP7>NTP3>NTP27>NTP8>NTP20>NTP23>NTP9>NTP11>NTP17>NTP18>NTP21>NTP25.

It is noteworthy that the smaller nitro group replacements, such as —C≡N, —Br, —CF3, —SO2Me and —F exhibit the greatest ability to antagonize the TPβ-mediated calcium responses. NTP4 exhibited greater than 50% inhibition of U46619-mediated responses when used at 0.5 similar to the previously identified TP20 and TP46. Hence, IC50 value for inhibition of U46619-mediated responses was determined in side-by-side comparison with TP20.

Example 4: Determination of IC50 Values for Inhibition of TP-Mediated [Ca2+]$_i$ Mobilization Determination of IC50 values for NTP4 and TP20, in side-by-side comparison, has been performed in both HEK.TPα and HEK.TPβ cells. Table 2.6 shows the results, where n=5 and n=6 for HEK.TPα and HEK.TPβ, respectively.

TABLE 2.6

$IC_{50}$ values for inhibition of U46619-mediated calcium mobilization in HEK.TPα and HEK.TPβ cells.

| TP Antagonist | $IC_{50}$ values for inhibition of U46619-mediated $[Ca^{2+}]_i$ (nM) | |
|---|---|---|
| | TPα | TPβ |
| TP20 (—NO$_2$) | 240 ± 29.8 | 9.61 ± 1.46 |
| NTP4 (—C≡N) | 593 ± 83.6 | 60.4 ± 8.00 |

NTP4 and TP20 are potent compounds.

Example 5: (2) Ex Vivo Platelet Aggregation Assays (A) Screening of ACTIVE NTP Antagonists: Whole Blood Aggregation Assays In order to evaluate the NTP compounds in a second independent assay, the effect of the ACTIVE NTP compounds (i.e., those compounds, when used at 1 μM, that exhibited ≥50% inhibition of TP (1 μM U46619)-induced activity in the initial screening calcium mobilization assays) on U46619-mediated platelet aggregation assays was examined. From an efficacy point of view, this is an important assay and, physiologically, relevant with respect to the therapeutic target.

Initially, the Sysmex haematological analyzer was used to examine the effect of the TP antagonists at a single concentration (0.1 μM) on U46619 (1 μM)-mediated platelet aggregation in whole blood.

Figure 3:
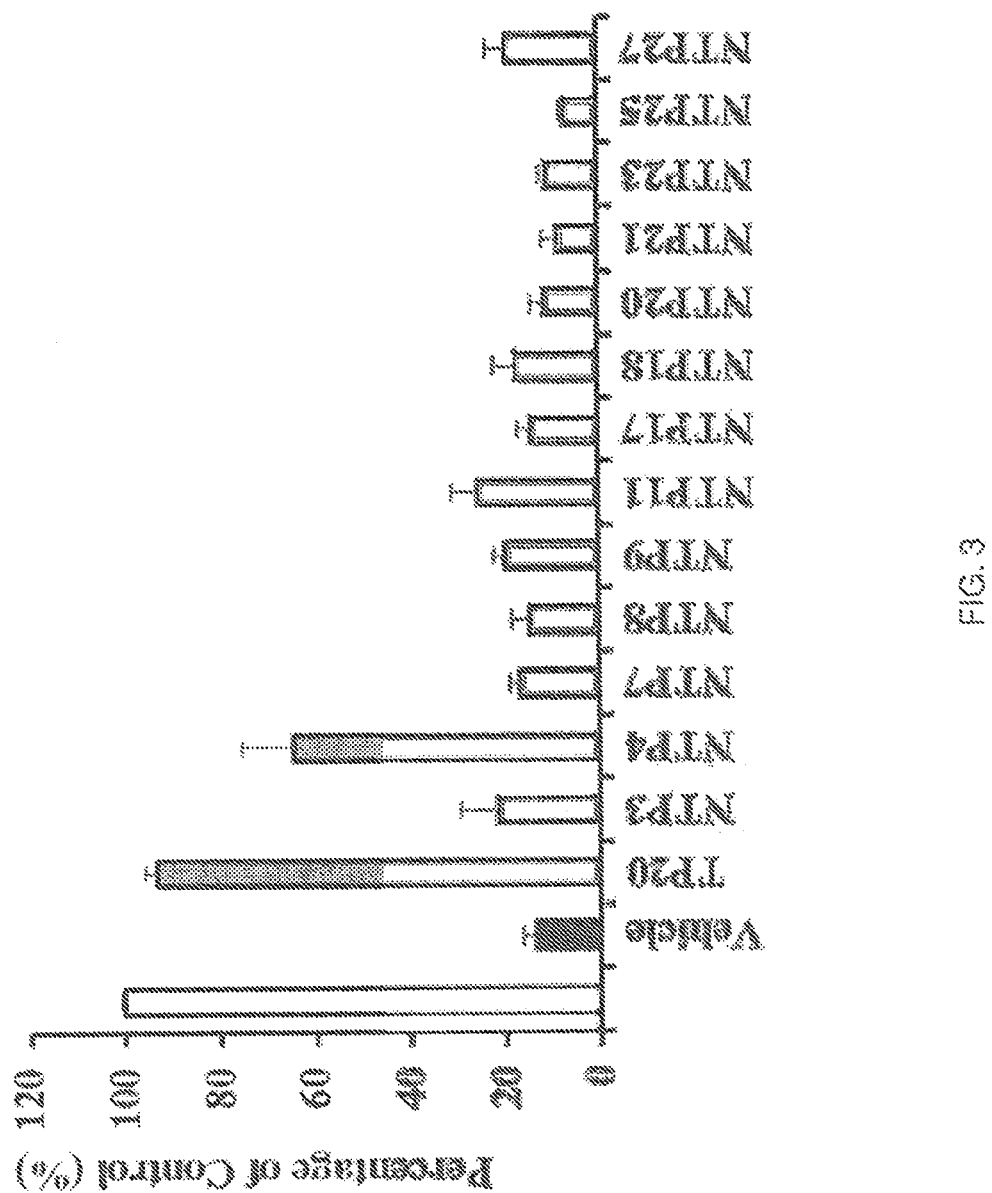
FIG. 3 illustrates effects of the TP antagonist compounds on U46619-mediated platelet aggregation.

FIG. 3 illustrates effects of the TP antagonist compounds on U46619-mediated platelet aggregation. Blood was taken form healthy volunteer by venupuncture into syringes containing 3.8% sodium citrate, 10 μM Indomethacin, such that the ratio of anticoagulant:blood was 1:9. The blood was aliquoted and incubated for 10 min with TP20 and selected NTP compounds, as indicated, where the antagonist were used at 0.1 μM prior to stimulation with 1 μM U46619 for 3 min. The blood was fixed with formaldehyde and platelet numbers counted using the Sysmex haematological analyzer. Data is presented as the mean percentage of control or non-treated blood sample (Percentage of Control; %) and represent data from 3 independent experiments were samples were treated in duplicate.

Consistent with previous data, the identified lead compound TP20, at 0.1 almost completely inhibited the reduction in platelet numbers caused by U46619-mediated platelet aggregation. NTP4 (0.1 μM) in some cases consistently inhibited the U46619-mediated reduction in platelet number by approx. 50%.

(B) Determination of IC50 Values for Inhibition of TP-Mediated Platelet Aggregation The effect of NTP4 and the previously identified lead TP antagonist, TP20, on U46619-mediated platelet aggregation in side-by-side comparisons was performed in platelet rich plasma (PRP) using the PAP-8E platelet aggregometer.

Table 2.7 shows the effect of TP Antagonists on U46619-mediated platelet aggregation and gives a summary of IC50 values for inhibition of U46619-mediated platelet aggregation.

TABLE 2.7

Effect of TP Antagonists on U46619-Mediated Platelet Aggregation: Summary of $IC_{50}$ Values for Inhibition of U46619-Mediated Platelet Aggregation.

| TP Antagonist | $IC_{50}$ Value for Inhibition of U46619-Mediated Platelet Aggregation (Mean ± S.E.M.; nM) |
|---|---|
| TP20 (Batch #4) | 4.62 ± 0.72 |
| NTP4 (Batch #2) | 40.3 ± 7.08 |

Note figures are based on data from ≥ independent experiments

Note figures are based on data from ≥6 independent experiments.

Figure 4A:
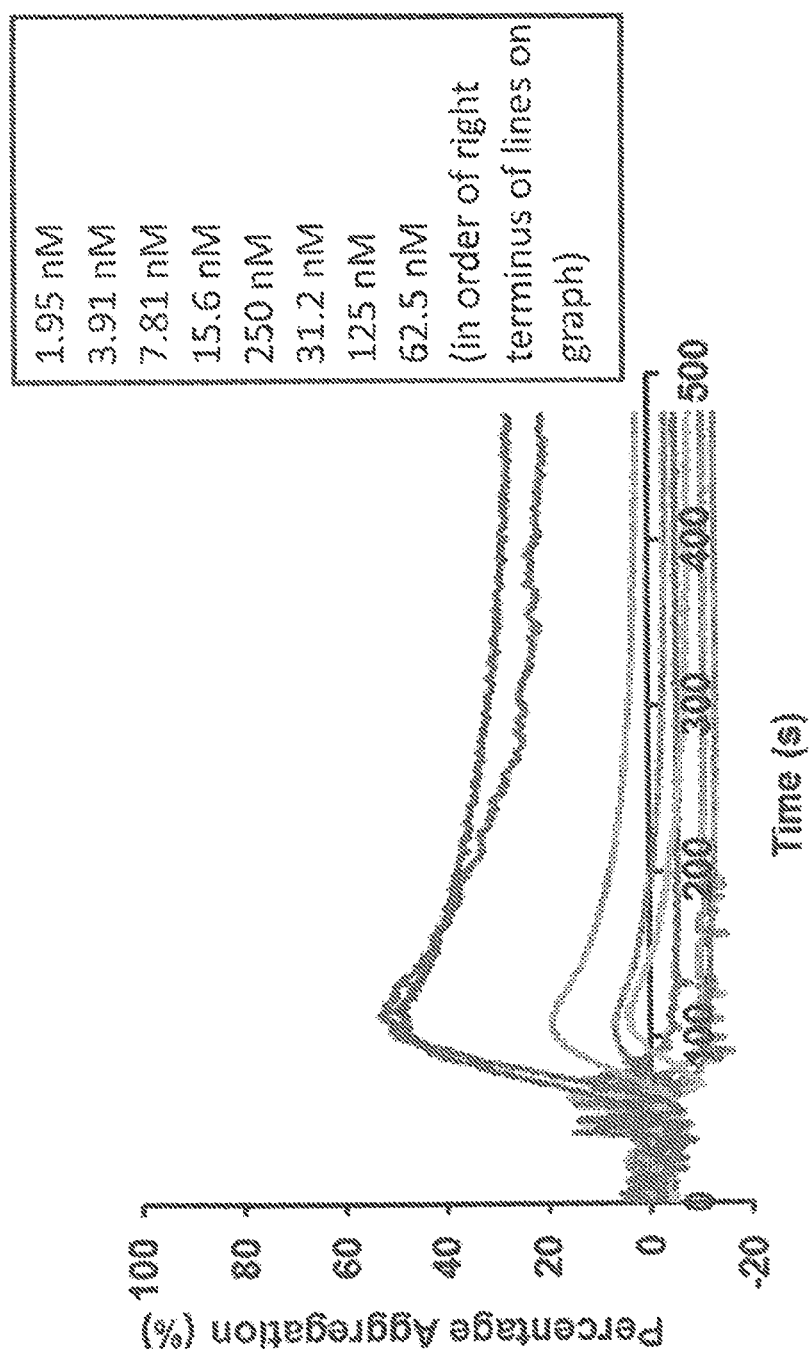
FIG. 4A-4C show the effect of TP20 & NTP4 on U46619-mediated platelet aggregation
Figure 4B:
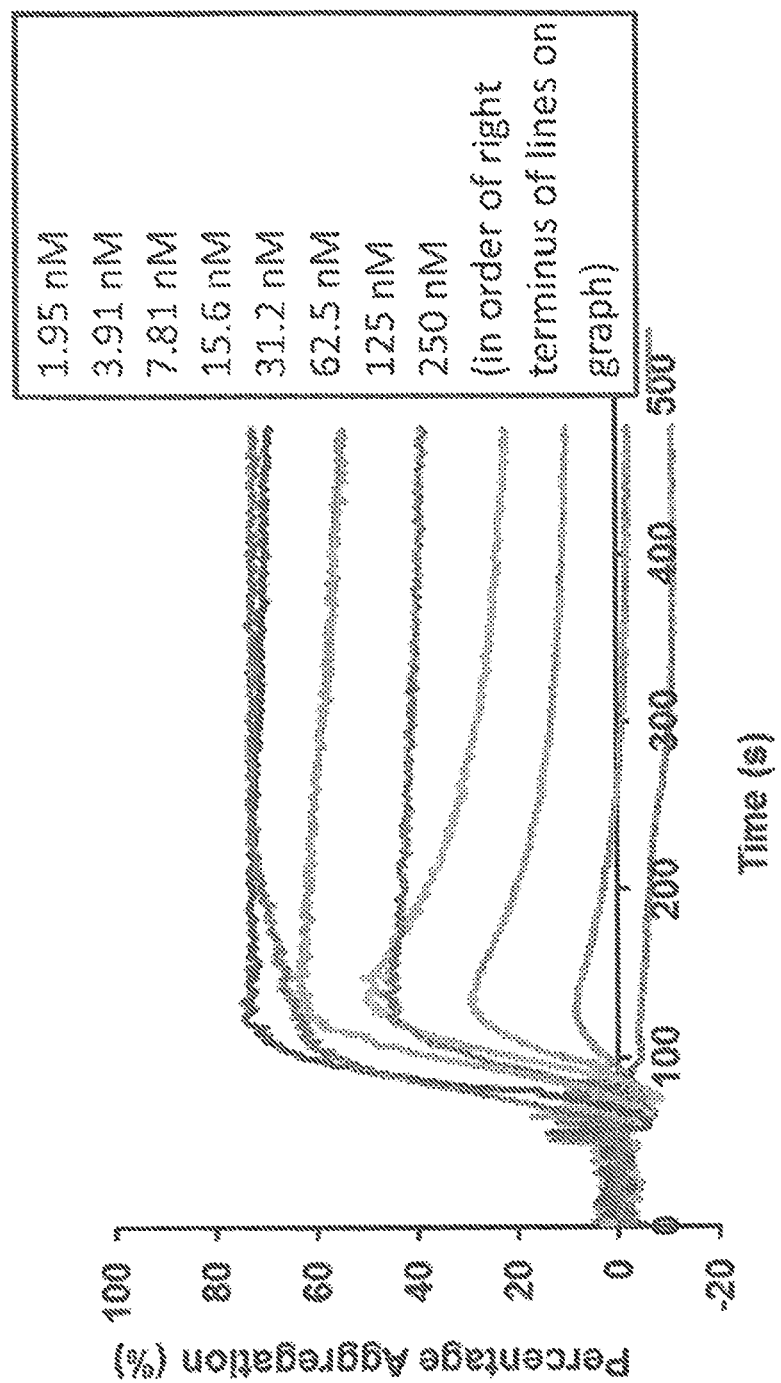
Figure 4C:
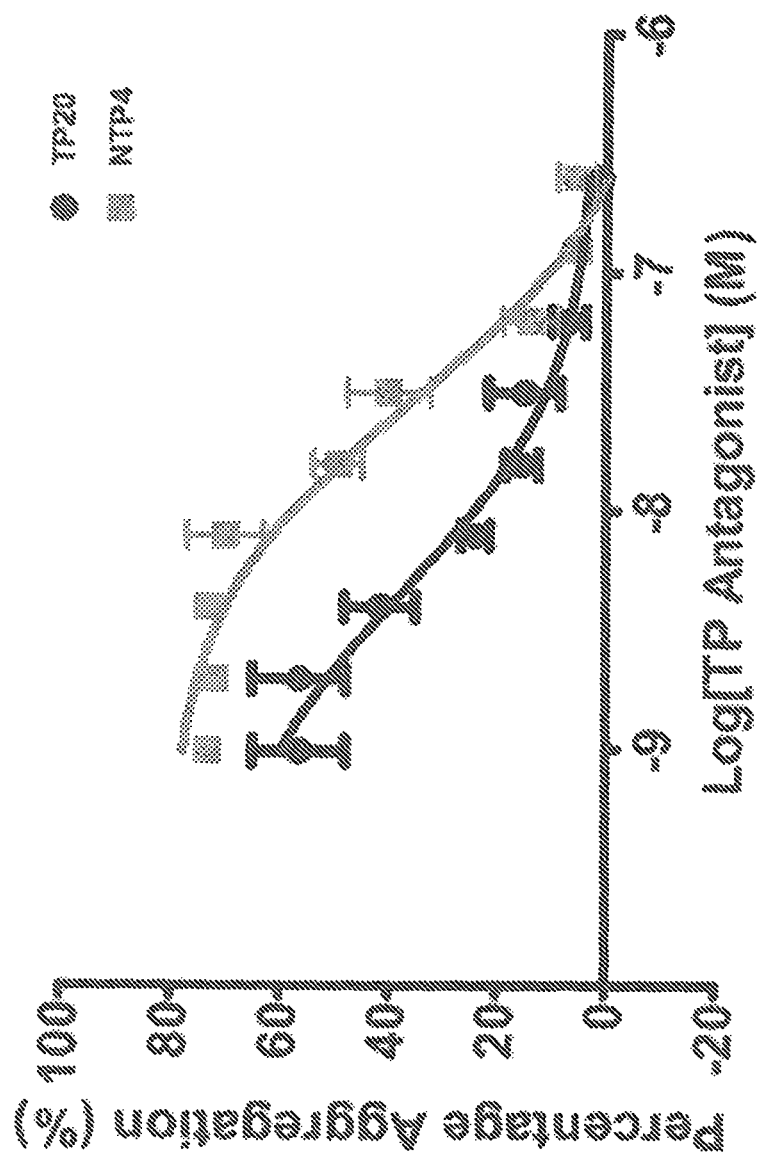

FIG. 4A-4C show the effect of TP20 & NTP4 on U46619-mediated platelet aggregation. PRP was prepared from blood taken from healthy volunteers into syringes containing 3.8% sodium citrate and 10 μM indomethacin such that the final ratio of anticoagulant to blood was 1:9. Aliquots of PRP (300 μl) were pre-incubated for 10 min with the TP antagonists, TP20 and NTP4, where 2-fold serial dilutions from 1 μM were prepared for each, prior to stimulating platelets with 1 μM U46619, incubated at 37° C., with stirring. FIG. 4A and FIG. 4B: Representative dose-response platelet aggregation profiles for TP20 (FIG. 4A) and NTP4 (FIG. 4B), where data is presented as Percentage Aggregation, as determined by changes in light transmission using the PAP-8E Platelet Aggregation Profiler as a function of time. FIG. 4C: The dose-response curves for platelet aggregation are presented as the mean (±S.E.M.) maximum Percentage Aggregation as a function of the log of the TP antagonist concentration. Data presented is representative of ≥6 independent experiments.

In side-by-side dose-response assays, TP20 is a potent TP antagonist with IC50=4.62±0.72 nM (n=7) for inhibition of U46619-mediated platelet aggregation. NTP4 is approx. ten-fold less potent than TP20 with IC50=41.5±7.69 nM (n=6) for inhibition of U46619-mediated platelet aggregation.

Example 6: Tumor and Metastasis Inhibition

An anticancer agent including a compound represented by formula X (hereinafter "X") was evaluated for the ability to inhibit tumor growth and experimental metastasis in a breast tumor xenograft model in immunocompromised (SCID) mice.

MDA-MB-231-2003 breast cancer cells ($1 \times 10^6$ in 0.1 ml PBS) were injected into the lateral tail vein of female SCID mice and the ability of X to inhibit metastasis to the lung was investigated (n=5 for the test X treated-mice or n=4 for the control PBS-treated mice). Mice were initially treated via intraperitoneal (i.p.) injection with either X (360 μg/kg; ~5 μM final concentration in blood; the "test" mice) or with PBS (the "control" mice) some 24 hr. before tumor cell injection. A second injection (i.p.) was given at the same dosage of X (360 μg/kg) at 4 hr. before tumor cell injection to the test mice while the control mice received an equivalent volume of PBS before tumor cell injection. The mice did not receive any additional injections with the test X or PBS prior to or following tumor cell injection. Thereafter, all mice were monitored by image analysis (IVIS® imaging system) every two weeks for tumor cells in their lungs and were sacrificed at day 28 post tumor cell injection.

Figure 5:
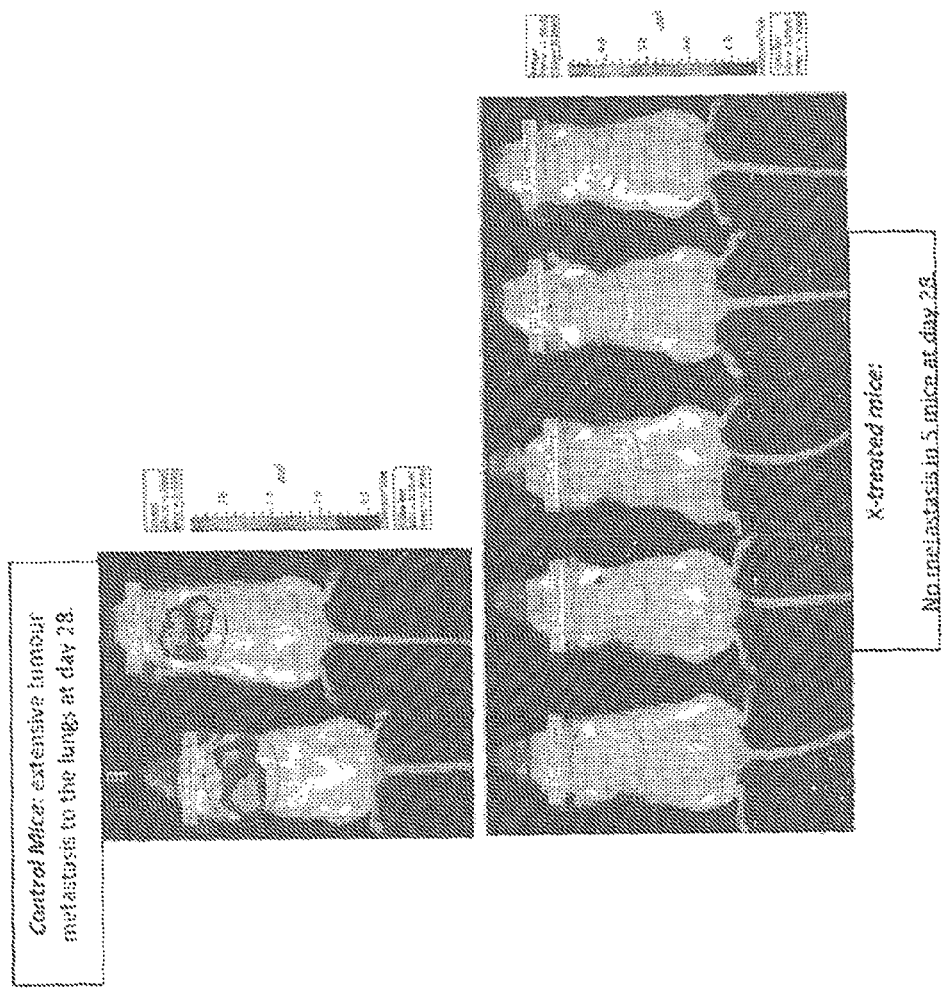
FIG. 5 shows metastasis in treated and control mice.
Figure 6:
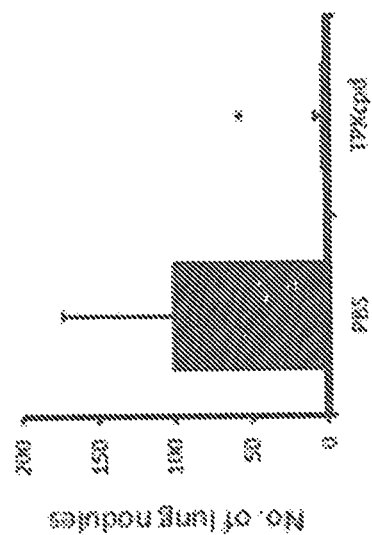
FIG. 6 shows a count of tumor nodules which developed in control and treated mice.
Figure 6:
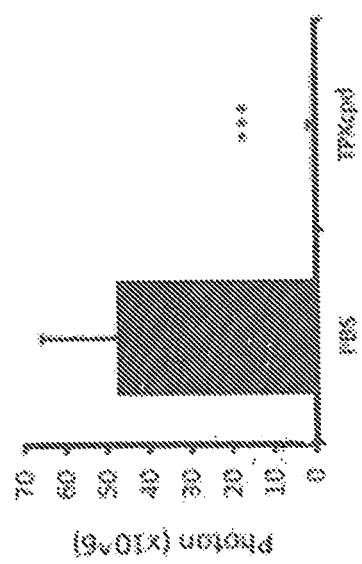

Results: Two of four mice in the control group died within 2-3 weeks following tumor cell injection due to tumor metastasis to the lung (data not shown) while the remaining 2 control mice survived to the end of the experiment at day 28 (FIG. 5; PBS-treated mice, upper 2 mice). As clearly indicated in FIG. 5, the two surviving PBS-treated mice developed extensive tumor nodules in the lung; FIG. 6 quantifies the number of tumor nodules which developed in the lungs of the PBS control versus the X treated mice. Conversely, all 5 of the test group that received X before tumor cell injection survived to the end of the experiment (day 28; lower panels). Furthermore, the X-treated mice did not develop any tumors (FIGS. 5 & 6; the 5 mice in the lower panels; p<0.001 (FIG. 1)), with only a very small trace of tumor metastasis evident in mouse #2.

Example 7: Evaluation of TP20 Efficacy as a Therapeutic for Breast Cancer

Figure 7:
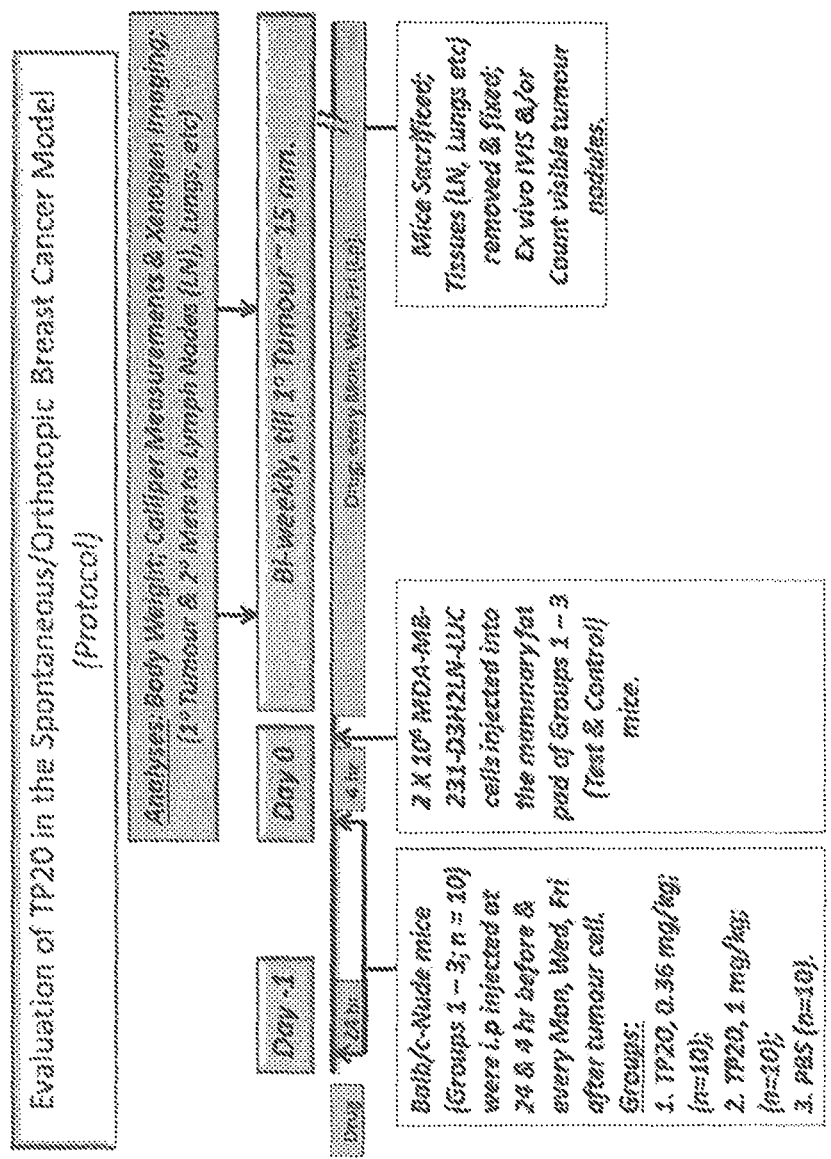
FIG. 7 provides a diagram of a study design.

In order to further assess the efficacy of TP20 for use as an anti-cancer, affecting primary tumor growth, and/or as an anti-metastatic agent, a spontaneous/orthotopic cancer model was employed by injection of the triple negative MDA-MB-231 breast cancer cell line (ER, PR, Her2 negative) into the mammary fat pad of immune compromised Balb-C nude mice. More specifically, in order to increase the growth rate of the primary tumor and increase the incidence of metastasis, a more aggressive variant of the MDA-MB-231 cell line, namely MDA-MB-231-D3H2LN-Luc (Jenkins et al., (2005), Breast Cancer Res, 7, 444-454), was used in the studies described below. Furthermore, the latter MDA-MB-231-D3H2LN-Luc cell line stably over-expresses the firefly luciferase gene (Luc) thereby enabling monitoring and in vivo detection of both the primary tumor and of the secondary metastasis by bioluminescent imaging in addition to assessment of the growth of the primary tumor by standard caliper measurements. In total, three groups of animals were studied and the diagram below gives an overview of the study design. FIG. 7 provides a diagram of a study design.

Summary of Main Findings:

(1) Effect of TP20 on Body Weight:

During the study, in the 3 treatment groups, Groups 1-3, animal body weights increased in line with expectations and there is no weight loss due to the experimental conditions used and, more specifically, due to repeat administration of immune-compromised Balb/c-Nude mice with TP20 at 0.36 mg/kg or at 1 mg/kg. Hence, analysis of animal body weight indicates that repeat administration with TP20 to Groups 1 & 2 animals is well-tolerated and has no adverse effects relative to administration of the drug vehicle (1% DMSO in PBS) to animals in Group 3.

(2) Effect of TP20 on Primary Tumor Growth:

The growth rate of the primary tumor in the TP20-treated mice (Groups 1 & 2) is significantly delayed relative to that of the vehicle-treated Group 3 mice (Non-linear regression, $p<0.0001$; see Table 4, page 7).

(3) Effect of TP20 on Animal Survival (Mean Day to Sacrifice of Animals whose Tumors Reach 15 mm):

The mean day to sacrifice is defined as time to maximum size of the 1° tumor to reach 15 mm. In the case of the Group 2 mice (1 mg/kg), there is a trend toward increased survival relative to the control Group 3 mice ($p=0.0949$ where the mean day to sacrifice for Group 2 mice is 38.4±3.86 days and for Group 3 mice is 30.5±1.20 days). In the Group 1 mice (treated with 0.36 mg/kg TP20), there was a statistically significant increase in mean day to sacrifice ($p=0.039$, compare 38.5±2.83 days vs. Vehicle, 30.5±1.20 days).

(4) Effect of TP20 on Breast Cancer Progression:

Treatment with TP20 (0.36 mg/kg, Group 1 and 1 mg/kg, Group 2) delays the progression of the breast cancer, as evidenced by the delay in the first appearance of metastases in the lymph nodes relative to that observed in the control, vehicle-treated mice (Group 3). Specifically, the mean day to first appearance on metastases in the lymph nodes is 17.2±1.14 days in Group 3, compared to 22.5±2.16 days ($p=0.0357$) and 26.2±3.71 days ($p=0.0265$) for the Group 1 (0.36 mg/kg) and Group 2 (1 mg/kg) animals, respectively.

Example 7.1: Effect of TP20 on Body Weight

Figure 8A:
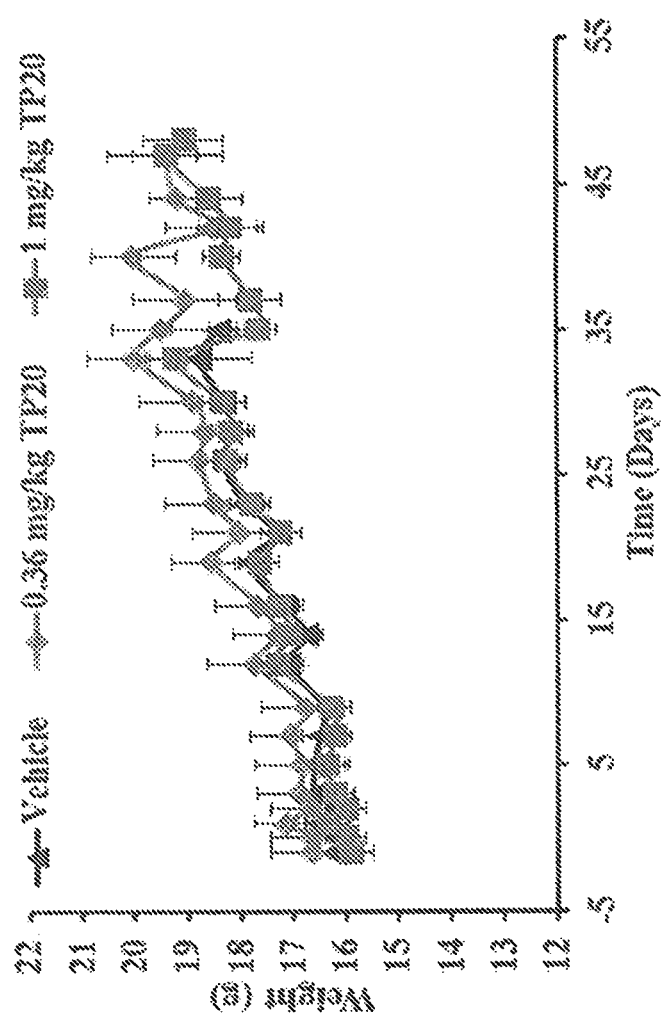
FIGS. 8A and 8B show the effect of TP20 on animal body weight in a study.
Figure 8B:
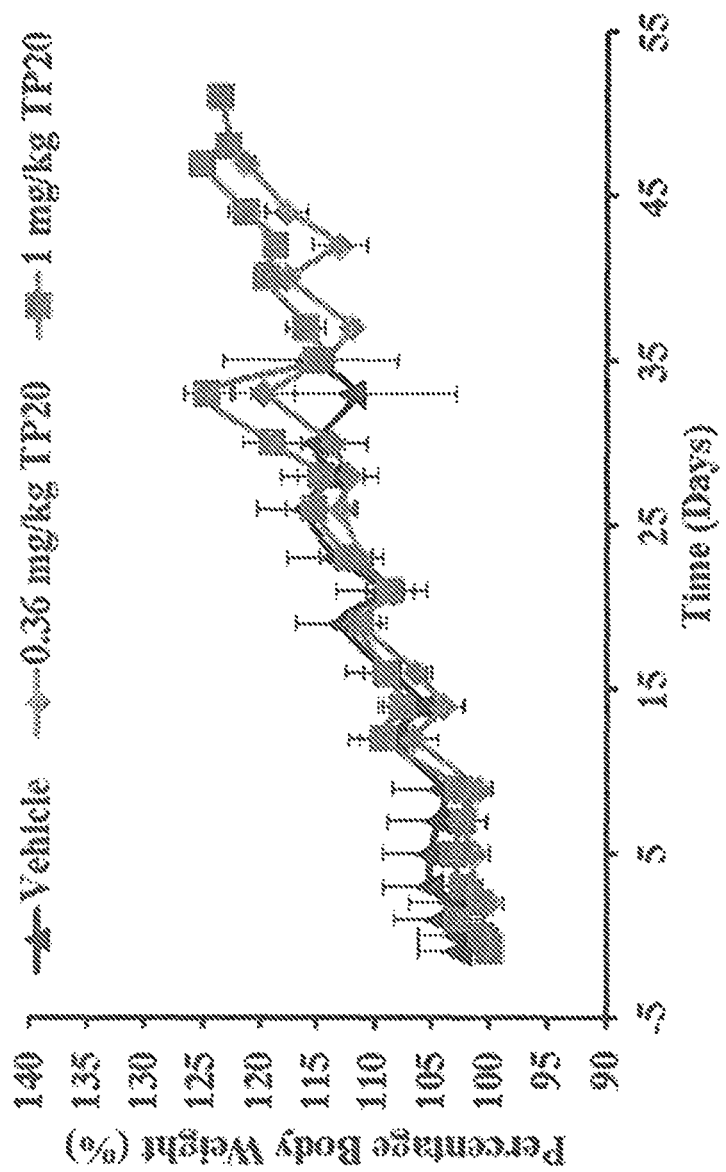

Body weights of the BALB/c nude mice were recorded prior to initiating the study and, thereafter, 3 times per week (Monday, Wednesday & Friday) following the mammary fat pad injection up to the point of sacrifice or death of the animal, as per welfare guidelines. Animals were typically sacrificed once the primary tumor reached 15 mm or, as required, if animals needed to be culled for welfare reasons. The mean change in weight of the animals in each of the treatments groups (Groups 1-3) is shown in FIG. 1 below:

FIGS. 8A and 8B show the effect of TP20 on Body Weight.

BALB/C-nude mice (female, 5-7 weeks old) were pre-treated 24 and 4 hr with TP20 at 0.36 mg/kg (blue line; Group 1), 1 mg/kg (red line; Group 2) or as control, vehicle (1% DMSO in PBS; black line; Group 3) prior to injecting MDA-MB-231-D3H2LN-Luc cells (50 µl, 2×106 suspended in 50% DPBS/50% Matrigel) into the mammary fat pad with a 27.5 G needle. Thereafter, mice were treated with TP20 or vehicle thrice weekly (Monday, Wednesday & Friday) until the primary tumor width reached 15 mm. Body weight was monitored 3 times per week. The data presented represents the mean (FIG. 8A; ±S.E.M.) or Percentage in Body Weight (FIG. 8B; ±S.E.M.), where weight at day −1 is 100%.

Linear regression analysis was performed on the raw body weight data to test for differences between the treatment groups (Groups 1-3) in terms of weight change during the study. The results are summarized in Table 2.8.

TABLE 2.8

Summary of Linear Regression Analysis of the Body Weight in TP20 and Vehicle Treatment Groups.

| | Linear Regression Analysis | |
| --- | --- | --- |
| Comparison | Between Groups (using means ± S.E.M. data) | Between Groups (using replicate data) |
| Group 3, Control vs. Group 1, 0.36 mg/kg TP20 | p = 0.6635 | p = 0.8149 |
| Group 2, 1 mg/kg TP20 vs. Group 2, 1 mg/kg TP20 | p = 0.27 | p = 0.7722 |
| Group 1, 0.36 mg/kg TP20 vs. Group 2, 1 mg/kg TP20 | p = 0.5211 | p = 0.5902 |

In general, the body weight of all animals, independent of drug treatment, increased over the course of the efficacy study, indicating that the experimental procedures involved (intraperitoneal injections, handling etc.) and the drug treatment themselves did not adversely affect the welfare of the animals.

During the study, in all cases the body weight increases and there is no weight loss associated with either the experimental conditions and more specifically with the repeat dosing of TP20. Hence, the body weight data indicates that repeat administration of mice with TP20 at 0.36 mg/kg and at 1 mg/kg is well-tolerated.

Example 7.2 Effect of TP20 on Primary Tumor Growth

Through the duration of the study to monitor the growth of the primary (1°) tumor, for welfare and experimental reasons, caliper measurements were performed thrice weekly (i.e., Monday, Wednesday & Friday) and involved measuring the width and length of the primary tumor mass. These measurements were then used in the following formula to calculate the tumor volume (mm3):

$$\text{Volume of Tumor (mm3)} = \text{length} \times \text{width}^2 \times 0.5$$

Note that the width measurements were used to determine day of sacrifice, i.e., once the diameter of the tumor was 15 mm or close to 15 mm the mice were sacrificed in line with animal welfare guidelines. FIG. 2, below, shows the mean (±S.E.M.) increase in tumor volume over time for each of the treatments groups 1-3.

FIG. 8 shows the effect of TP20 on Primary (1°) Tumor Volume.

BALB/C-nude mice (female, 5-7 weeks old) were pre-treated 24 and 4 hr with TP20 at 0.36 mg/kg (blue line; Group 1), 1 mg/kg (red line; Group 2) or as control, vehicle (1% DMSO; black line; Group 3) prior to injecting MDA-MB-231-D3H2LN-Luc cells (50 µl, 2×106 suspended in 50% DPBS/50% Matrigel) into the mammary fat pad with a 27.5 G needle. Thereafter, mice were treated with TP20 or vehicle thrice weekly (Monday, Wednesday & Friday) until the primary tumor diameter reached 15 mm. Primary tumor growth was monitored thrice weekly using caliper measurements where tumor volume (mm3) is calculated by the formula Volume=Length×width2×0.5. The data presented represents the mean (±S.E.M.) tumor volume (mm3) for each of the treatment groups as a function of time (days). Fine black lines represent the linear trend for each of the treatment groups.

Table 2.9 below provides the results of the Linear regression analysis for the comparisons of the primary tumor volume data for Groups 1-3.

TABLE 2.9

Summary of Non-Linear Regression Analysis of the Tumor Volume in TP20 and Vehicle Treatment Groups.

| Comparison | Linear Regression Analysis |
|---|---|
| Group 3, Control vs. Group 1, 0.36 mg/kg TP20 | p < 0.0001 |
| Group 3, Control vs. Group 2, 1 mg/kg TP20 | p < 0.0001 |
| Group 1, 0.36 mg/kg TP20 vs. Group 2, 1 mg/kg TP20 | p = 0.2836 |

As indicated in Table 2.9, there are significant differences between each of the TP20 treatment groups and the vehicle, where TP20 significantly decreases the primary tumor growth (compare Group 1, 0.36 mg/kg vs. Group 3, Control, p<0.0001; compare Group 2, 1 mg/kg vs. Group 3, Control, p<0.0001). There is no significant difference between the two TP20 groups (compare Group 1, 0.36 mg/kg vs. Group 2, 1 mg/kg, p=0.2836).

Both Group 1 (p<0.0001) and Group 2 (p<0.0001) mice exhibit significantly reduced rate of primary tumor growth compared to the control Group 3, indicating that TP20 impedes the primary tumor growth. There is no difference between the TP20 treatments groups, Group 1 and Group 2, where p=0.2836.

Example 7.3: Effect of TP20 on Animal Survival (3i) Survival Analysis

As the 1° tumors reached 15 mm in diameter, for welfare reasons the animals were sacrificed. The day of sacrifice was analyzed using Kaplan-Meier survival analysis and subsequent Log-Rank and Wilcoxon tests to compare any differences between the treatments groups in terms of time of death.

Figure 9:
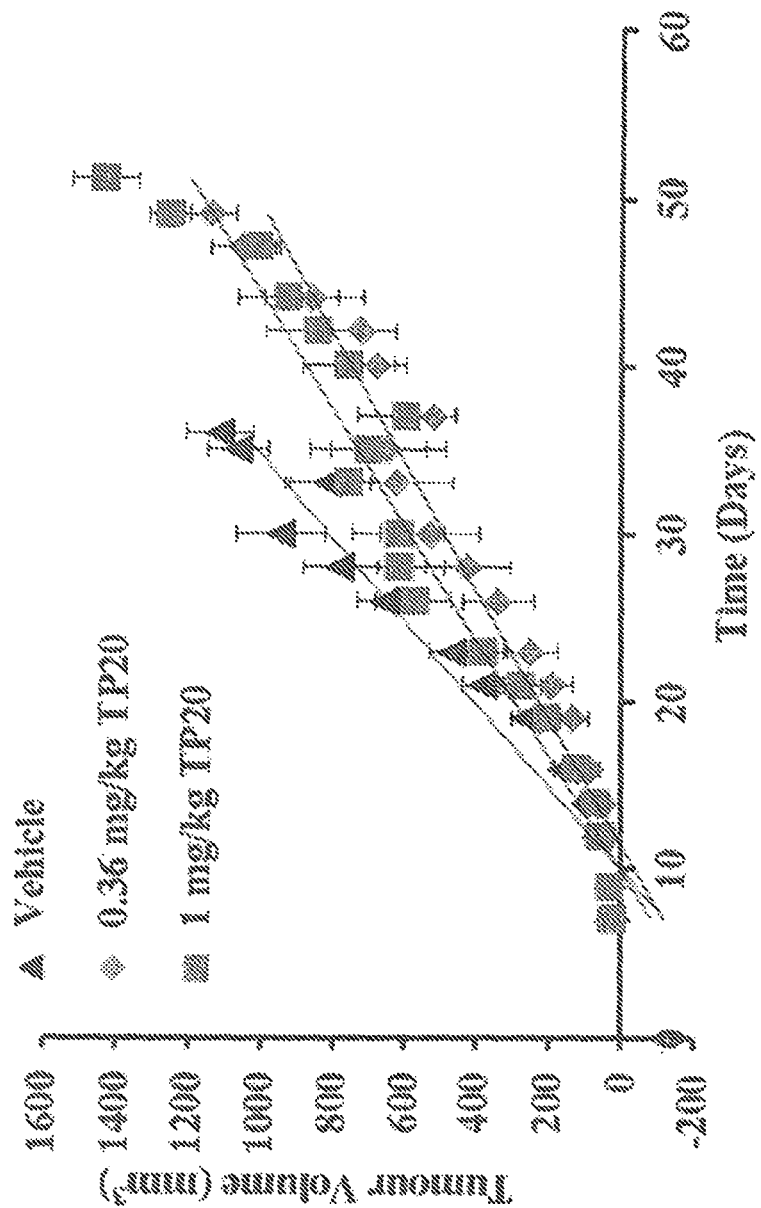
FIG. 9 shows the effect of TP20 on primary tumor volume.
Figure 10:
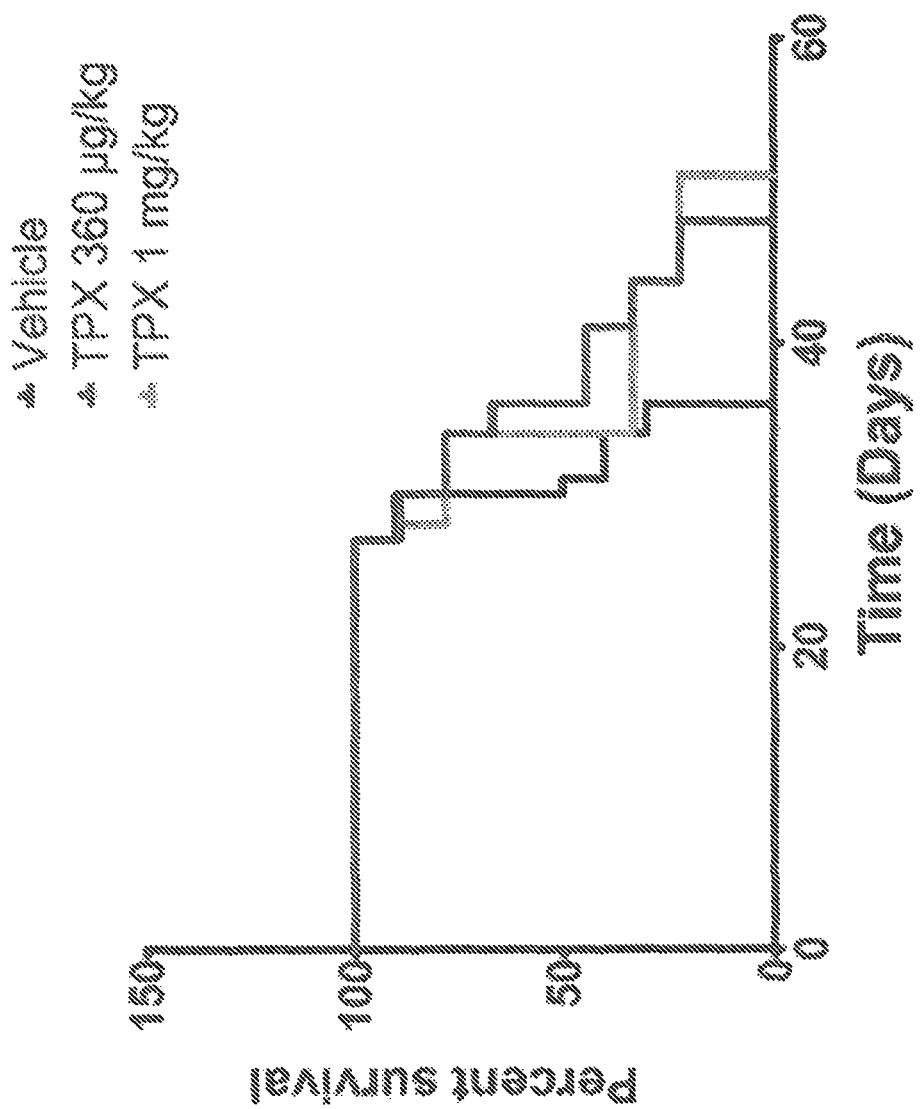
FIG. 10 shows effects of compounds on animal survival.

FIG. 9 illustrates the effect of TP20 on Animal Survival. BALB/C-nude mice (female, 5-7 weeks old) were pretreated 24 and 4 hr with TP20 at 0.36 mg/kg (blue line; Group 1), 1 mg/kg (red line; Group 2) or as control, vehicle (1% DMSO; black line; Group 3) prior to injecting MDA-MB-231-D3H2LN-Luc cells (50 µl, 2×106 suspended in 50% DPBS/50% Matrigel) into the mammary fat pad with a 27.5 G needle. Thereafter, mice were treated with TP20 or vehicle thrice weekly (Monday, Wednesday & Friday) until the primary tumor diameter reached 15 mm at which point animals were sacrificed. The data is presented as Kaplan-Meier survival plots where Panel A represents the uncensored data and Panel B represents the censored data. FIG. 10 shows percent survival over days.

The Kaplan-Meier charts (FIG. 10) show that there is a trend toward increased survival of the TP20-treated mice (Groups 1 and 2) compared to vehicle-treated mice (Group 3). However, this is only significant in the case of the Group 1 mice (0.36 mg/kg group; p=0.0392). There was no significant difference between the Group 2 mice (1 mg/kg) group relative to the control Group 3 mice ((p=0.1264) or between the 2 TP20-treated groups (p=0.5559). In the case of the former, the Kaplan-Meier chart indicates a distinct trend toward prolonged survival of the animals.

(3ii) Mean Day to Sacrifice

In order to assess the effect of TP20 on the survival of the animals, the mean day of sacrifice for each treatment was calculated from the day at which each animal reached maximum primary tumor width, i.e., 15 mm, where in the case of an animal being sacrificed for a reason other than attaining the maximum tumor diameter, i.e., welfare issues or unexpected death, data was excluded. The results of the subsequent T-test analyses to compare the mean day to sacrifice between Groups 1-3 are shown in Table 2.10 below.

TABLE 2.10

Effect of TP20 on Animal Survival.

| Treatment Group | Day of Sacrifice Mean ± S.E.M. (N = x) | T-test Analysis vs. Group 3, Control | T-test Analysis vs. Group 2, 1 mg/kg TP20 |
|---|---|---|---|
| Group 1, 0.36 mg/kg TP20 | 38.5 ± 2.83 (N = 8) | p = 0.0391 | p = 0.9881 |
| Group 2, 1 mg/kg TP20 | 38.4 ± 3.86 (N = 7) | p = 0.0949 | — |
| Group 3, Control | 30.5 ± 1.20 (N = 6) | — | — |

Using the data from the mice that were sacrificed when their primary tumor reached 15 mm T-test analysis of the mean day to sacrifice indicated that the Group 1 (0.36 mg/kg TP20) was significantly increased relative to the vehicle treated animals (compare Group 1, 0.36 mg/kg vs. Group 3, Control, p=0.0391). In other words, the survival in the TP20 treated mice was significantly prolonged in the Group 1 mice. While 2 mice from the Group 2 (1 mg/kg) had extended survival, up to 51 days, there was no significant difference in mean day to death compared to the vehicle (compare Group 2, 1 mg/kg vs. Group 3, Control, p=0.095).

There is a trend toward increased survival in mice treated with TP20, where in the case of Group 1 (0.36 mg/kg) this is significant (p=0.039) while in Group 2 (1 mg/kg), a larger group is required to establish significance.

Example 7.4: Effect of TP20 on Breast Cancer Progression

Bioluminescent imaging (IVIS) was carried out twice weekly to monitor primary tumor growth and to detect secondary metastases sites. Lymph node metastases were detected from Day 13 onwards were the day of first appearance is analyzed below through Kaplan-Meier (4i) and T-test analysis (4ii).

Figure 11:
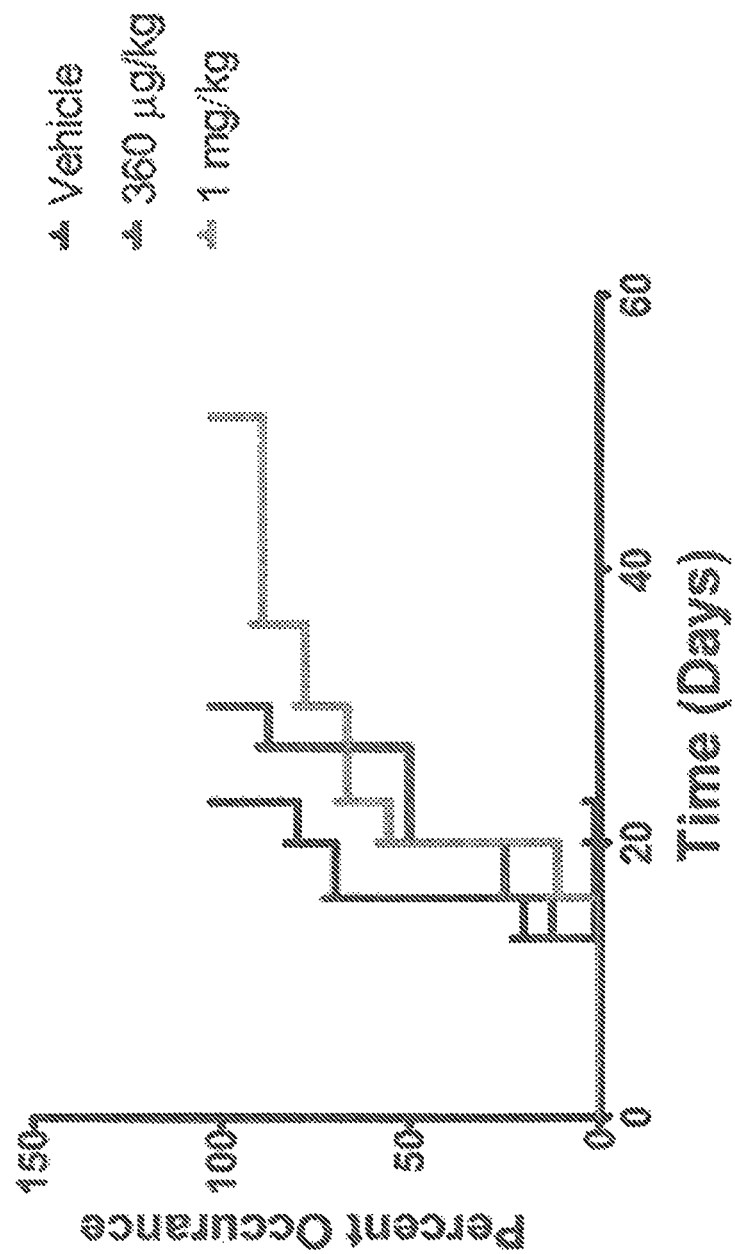
FIG. 11 shows the effect of TP20 on cancer progression in an animal study.

(4i) Kaplan-Meier Analysis on Day to First Appearance of Metastasis:

FIG. 11 shows the effect of TP20 on Cancer Progression: Appearance of Lymph Node Metastases. BALB/C-nude mice (female, 5-7 weeks old) were pre-treated 24 and 4 hr with TP20 at 0.36 mg/kg (blue line; Group 1), 1 mg/kg (red line; Group 2) or, as controls, vehicle (1% DMSO; black line; Group 3) prior to injecting MDA-MB-231-D3H2LN-Luc cells (50 2×106 suspended in 50% DPBS/50% Matrigel) into the mammary fat pad with a 27.5 G needle. Thereafter, mice were treated with TP20 or vehicle thrice weekly (Monday, Wednesday & Friday). The appearance of lymph node metastases was monitored twice weekly using IVIS imaging. The data is presented as Kaplan-Meier plots.

TABLE 2.11

Effect of TP20 on Onset of Metastasis.

| | Log-Rank Test | |
|---|---|---|
| Treatment Group | Analysis vs. Group 3 | Analysis vs. Group 1 |
| Group 1, 0.36 mg/kg TP20 vs. Group 3, Control | p = 0.0274 | — |
| Group 2, 1 mg/kg TP20 vs. Group 3, Control | p = 0.0173 | p = 0.7198 |

The Kaplan-Meier plot indicates a trend towards a delay in the first appearance of metastases in the lymph nodes in the TP20-treated mice. This was confirmed in the subsequent Mantel Cox analysis which indicated that TP20 significantly increased the time for metastases to appear (compare Group 1, 0.36 mg/kg vs. Group 3, Control, p=0.0274; compare Group 2, 1 mg/kg vs. Group 3, Control, p=0.0173).

(4ii) Mean Day to First Appearance of Metastasis:

The onset of metastasis or day to first appearance of lymph node metastasis was assessed through T-test analysis, where significance from control was observed at both the 1 (p=0.0265) & 0.36 (p=0.0357) mg/kg dose.

TABLE 2.12

Effect of TP20 on Onset of Metastasis.

| | First Appearance of | T-test | |
|---|---|---|---|
| Treatment Group | Mets, Mean ± S.E.M. (N = x) | Analysis vs. Group 3 | Analysis vs. Group 1 |
| Group 1, 0.36 mg/kg TP20 | 22.5 ± 2.16 (N = 8) | p = 0.0357 | — |
| Group 2, 1 mg/kg TP20 | 26.2 ± 3.71 (N = 9) | p = 0.0265 | p = 0.4156 |
| Group 3, Control | 17.2 ± 1.14 (N = 10) | — | — |

TP20 delays the progression of the breast cancer, as evidence by the delay in the first appearance of metastases in the lymph nodes.

There is a significant difference in the onset of metastasis or day to first appearance of metastases in the lymph nodes between the vehicle and TP20-treatment groups, independent of concentration of TP20. There is no difference between the two TP20-treatment groups, suggesting that the higher concentration of TP20 (1 mg/kg) does not offer any additional benefit over the lower concentration (0.36 mg/kg).

Example 8: Efficacy Study of TP20 as an Agent for Use in Flu-Infected Mice

In order to assess the potential efficacy of TP20 (for reasons of confidentiality, is also called TPX in this document) for use in the treatment of mice infected with the influenza virus, a 14-day efficacy study was carried out as detailed below. As a prelude to this 14-day efficacy study, it was first necessary to carry out a preliminary safety/tolerability study to assess whether TP20 itself had an inherent effects on the mice. As outlined below, the work was carried out in two phases: Phase 1, representing the Safety/Tolerability study and Phase 2, representing the 14-day efficacy study.

Topline Summary of IITRI Study:

1. Preliminary/Phase I study—The tolerability of repeat daily dosing of TP20 (0.36 mg/kg/dose×twice daily by oral gavage) was monitored in BABL/c mice for 5 days, where survival and body weights were measured over a 0-14 day period and compared to placebo control animals (PBS-treated animals). Conclusion: TP20 was well tolerated and there were no safety issues in the TP20-treated animals relative to the placebo (PBS-treated) group.

2. Phase II Analysis (Viral-treated Animals):

The effect of TP20 on BABL/c mice infected with the Influenza A/Puerto Rico/8/1934 H1N1, where the challenge was 5 MLD50 units (100% mortality within 10 days), was compared to that of Tamiflu, the combination of both TP20 and Tamiflu or placebo. To this end, four groups of 19 animals (Groups 1-4; see below for treatment groups and dosages) were treated twice a day by oral gavage, where the first drug treatment was 2 hr before viral inoculation. The drug treatments were continued for 5 days where animals were monitored for body weight and survival for up to Day 14 post-viral infection. Animals (3 per group) were harvested on Days 3 & 7 for viral titers following bronchiolar lavage and Day 4 for histopathological assessment of microscopic evidence of responses in H&E stained lung tissue sections. The animal groups were as follows:

Group 1=Placebo (PBS-treated).
Group 2=10 mg/kg/dose Tamiflu
Group 3=0.36 mg/kg/dose TP20 (Note, TP20 is also referred to as TPX).
Group 4=0.36 mg/kg/dose TP20+10 mg/kg/dose Tamiflu.

(A) Survival Analysis:

A(i). All animals in Groups 1 and 3 died, while all animals in Groups 2 and 4 survived to the end of the study (day 14). Hence, in the latter, TP20 was well tolerated even when used in flu-infected mice and in combination with Tamiflu.

A(ii). In terms of Group 1 versus Group 3 mice—while all animals died in these groups, there was a trend toward a better response in the TP20-treated (Group 3) animals compared to the Placebo (PBS-treated mice) in Group 1. Specifically, in Group 1, of the 10 animals in the survival arm of the study, 3 died on Day 6 and the remaining 7 died on Day 7. In contrast, of the 10 animals in Group 3, only 2 died on Day 6, 5 died on Day 7, 2 survived to Day 8 and 1 actually survived to day 9.

The TP20/TPX mice in Group 3 showed a tendency toward better survival than the Placebo (PBS-treated mice) in Group 1.

(B) Body Weight Analysis:—

B(i). Body Weight Loss: This mainly occurs during the initial stages post-viral infection (Days 0-7).

In line with their non-survival, animals in Groups 1 and 3 had significantly greater body weight loss than animals in Groups 2 and 4. Furthermore, there was no significant difference in the amount or rate of total body weight loss between animals in Group 1 relative to Group 3. Similarly, there was no significant difference of the amount or rate of total body weight loss between animals in Group 2 relative to Group 4.

B(ii). Body Weight Recovery: this only occurred in Group 2 and Group 4 animals and mainly occurred ~7-9 Days, i.e., in the Recovery Phase post-viral infection. The following conclusions can be made:

B(iia). There was no significant difference in the overall weight loss between animals in Group 2 (Tamiflu only) versus animals in Group 4 (TP20+Tamiflu).

B(iib). However, animals in Group 2 recovered between Day 7 (n=3) and Day 9 (n=7), with a Mean Day to Recovery of 8.4±0.31 days (days±SEM; n=10). Animals in Group 4 recovered between Day 7 (n=8) and Day 9 (n=2), with a Mean Day to Recovery of 7.4±0.267 days (days±SEM;

n=10). Hence, there was a significant difference in the Day to Recovery between the 2 groups of mice, with the Group 4 (TP20+Tamiflu) mice recovering 24 hr faster than the Group 2 (Tamiflu only) mice where p=0.024.

B(iic). Note, consistent with point B (iib), on Day 9, mice in Group 4 also showed an improved weight gain (Weight on Day 9 expressed as a Percentage relative to Minimum Weight) relative to mice in Group 2, where p=0.0602 using Student's two tailed T-test or p=0.0301 using the one-tailed T-test.

B(iid). By day 14, mice in Groups 2 and Groups 4 had fully recovered from flu infection and there was no difference on their weights between: Day 0 and Day 14—Group 2: p=0.6653 (Unpaired T-test); p=0.4840 (Paired T-test) and Day 0 and Day 14—Group 4: p=0.5778 (Unpaired T-test); p=0.0422 (Paired T-test).

B(iie). In terms of actual Rates of Recovery, linear regression analysis of the Rates of Recovery between animals in Group 2 and in Group 4 didn't indicate a significant difference. However, this is likely to be due to the fact that so few weight measurements were made during the recovery phase—Days 7/9—Day 14 and by Day 14—all mice had fully recovered. Hence, those few measurements didn't support a difference in Rates of Recovery per se.

Promising data were obtained on the Mean Day to Recovery for animals in Group 4 versus Group 2, where the former recovered 24 hr faster, as well as the trend toward better survival of the animals in Group 3 (TP20 alone) relative to the placebo (Group 1) animals.

(D) Histopathology:—Lung Tissue Harvested on Day 4 Post-Viral Infection (n=3/Group).

(Di) Pathological Assessment: lungs were harvested from 3 mice in each Group 1-4 at Day 4 post-viral infection; were fixed and stained (H & E staining), analyzed and scored (minimal, mild, moderate, marked and severe) for the following 6 parameters:

Perivascular edema (cellular & fluid accumulation associated with acute inflammation)
Bronchiolar acute inflammation
Bronchiolar exudates (fluid with high protein content from blood vessels; a measure of response to injury and part of the healing process)
Bronchiolar erosion
Vascular necrosis
Alveolar acute inflammation For results, refer to Table 2.13 from the pathological assessment and to FIG. 18.

TABLE 2.13

Histopathology Females

| | Group | | | |
|---|---|---|---|---|
| | 1 | 2 | 3 | 4 |
| | Dose (mg/kg/dose) | | | |
| | 0 | 10 Tami | 0.36 TP20 | 10 Tam + 0.36 TP20 |
| No of Animals Analyzed | 3 | 3 | 3 | 3 |
| Lung (No examined) | 3 | 3 | 3 | 3 |
| Perivascular Edema | (3) | (2) | (3) | (1) |
| Minimal | 2 | 1 | 3 | 1 |
| Mild | 1 | 1 | 0 | 0 |
| Bronchiolar acute Inflammation | (3) | (3) | (3) | (3) |
| Minimal | 2 | 0 | 3 | 1 |
| Mild | 1 | 3 | 0 | 2 |

TABLE 2.13-continued

Histopathology Females

| | Group | | | |
|---|---|---|---|---|
| | 1 | 2 | 3 | 4 |
| | Dose (mg/kg/dose) | | | |
| | 0 | 10 Tami | 0.36 TP20 | 10 Tam + 0.36 TP20 |
| Bronchiolar Exudate | (3) | (3) | (3) | (3) |
| Minimal | 3 | 1 | 2 | 1 |
| Mild | 0 | 2 | 1 | 1 |
| Moderate | 0 | 0 | 0 | 1 |
| Bronchiolar Erosion | (3) | (3) | (3) | (3) |
| Minimal | 0 | 0 | 0 | 1 |
| Mild | 3 | 2 | 3 | 1 |
| Moderate | 0 | 1 | 0 | 1 |
| Vascular Necrosis | (2) | (0) | (0) | (0) |
| Minimal | 2 | — | — | — |
| Alveolar Acute Inflammation | (0) | (1) | (0) | (0) |
| Minimal | — | 1 | — | — |

Note:
number in parentheses represent the number of animals with the finding.

Taking the 6 parameters listed in Table 2.13, there was a tendency toward decreased Perivascular edema and Bronchiolar acute inflammation in the TP20-treated (Group 3) relative to the PBS-treated (Group 1) mice and in the TP20+Tamiflu—(Group 4) relative to the Tamiflu alone—(Group 2)-treated mice. Hence, there was a tendency toward less inflammation with TP20.

Also, in examining the Bronchiolar exudates, (a measure of response to injury and part of the healing process showing increased fluid with high protein content from blood vessels), there was a tendency toward increased exudates in the Group 3 relative to Group 1 mice. Also, there was a tendency toward increased exudates in the Group 4 relative to Group 2 mice, again suggesting that TP20 may be encouraging the healing process, lessening the lung burden post-viral infection.

In terms of Bronchiolar erosion, it was mild in both Groups 1 and 3 mice but slightly reduced in the Group 4 relative to Group 2 mice. Vascular necrosis was only observed in the PBS-treated (Group 1, n=2/3) mice while Alveolar acute inflammation was only observed in one of the Tamiflu-treated (Group 2) mice and not in the others in Group 2 or other Groups 1, 3 or 4.

Overall conclusion from histopathology, while not statistically significant, bearing in mind study group size (n=3), TP20 does appear to show reduced inflammation (i.e., act as an anti-inflammatory agent) and in improvement in terms of production of Bronchiolar exudates, a component of the healing process.

(Dii) Quantification of Perivascular Edema in Lung Tissue:

In an attempt to quantify the pathological changes in the viral infected mice, the H&E slides provided by IITRI/Charles River were electronically scanned using the Aperio slide scanning system and the extent of perivascular edema assessed using Image J. Quantification and subsequent T-test analysis indicates that while Tamiflu alone does not reduce the extent of edema (p=0.2793), TP20, either alone (p=0.0003) or in combination with Tamiflu (p<0.0001), reduces it by 20-30% compared to vehicle. The data supports TP20 as an anti-inflammatory agent that when used alone or in combination with Tamiflu reduces perivascular edema associated with acute inflammation.

Detailed Description and Analysis of the Phase 1 and Phase 2 Studies.

(1) Preliminary/Phase 1 Study (Safety/Tolerability Study)

Effect of TP20 on Survival & Body Weight of BALB/c mice

The tolerability of TP20, measured as survival and change in body weight, was examined in BALB/c mice administered TP20 or placebo by oral gavage twice daily at 360 Mg/kg (100 μl dosing volume), for 6 days. Mice were monitored for 14 days and weighed 3 times a week. The results are shown below.

Figure 12A:
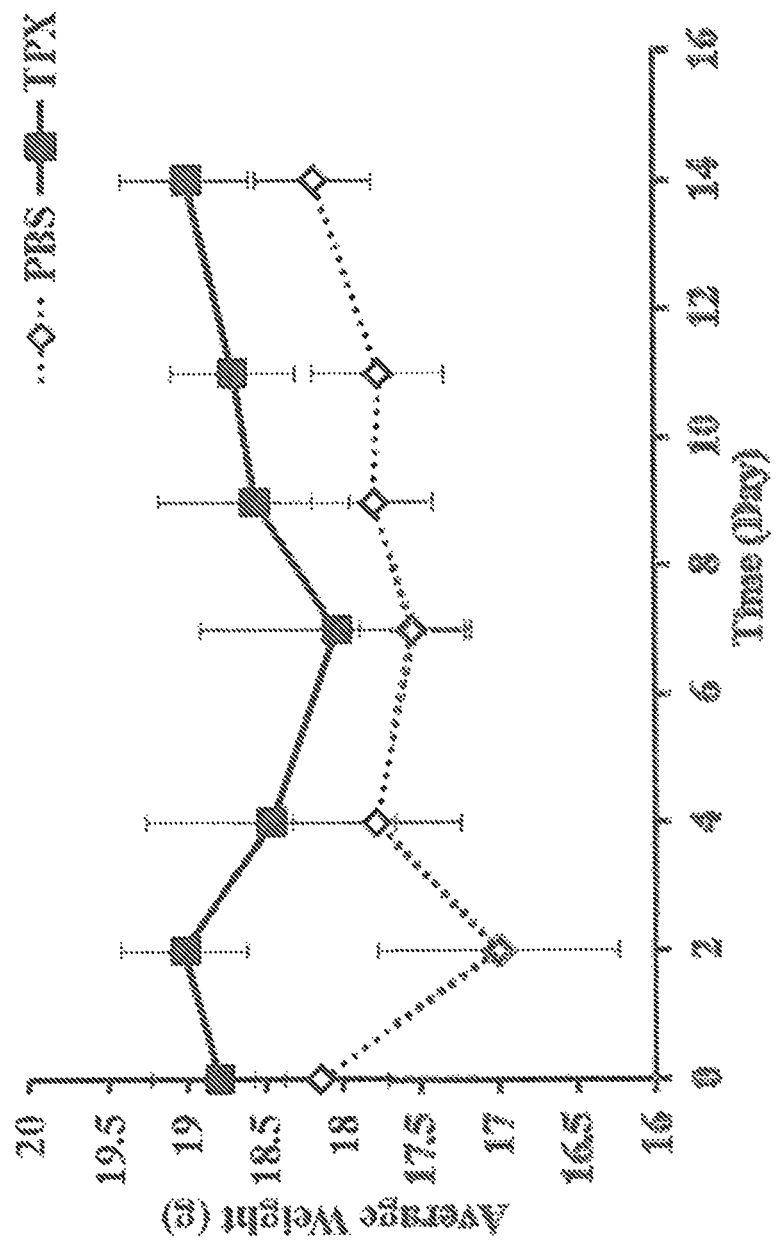
FIGS. 12A and 12B show the effect of TP20 on body weight of BABL/c Mice.
Figure 12B:
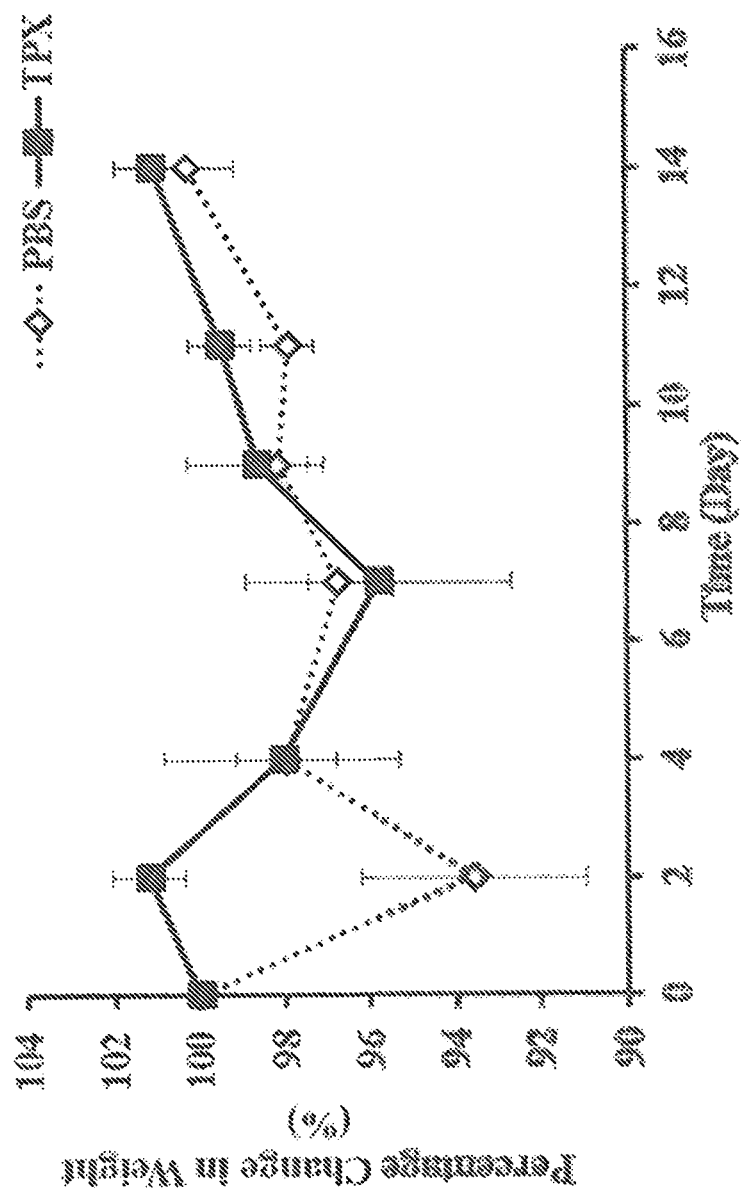

FIGS. 12A and 12B show the effect of TP20 on Body Weight of BABL/c Mice. BALB/c mice (7-8 weeks, female), 5 animals per treatment group, were administered TP20 (TPX; solid lines, ■) at 360 μg/kg or placebo (dashed lines, ◊) by oral gavage twice daily (100 μl dosing volume), for 6 days. Mice were monitored for 14 days and weighed 3 times a week. Data is presented as mean body weight (±S.E.M.; FIG. 12A) or as mean percentage change in body weight (±S.E.M.; FIG. 12B) as a function of time.

All mice survived repeat dosing of TP20/TPX. The placebo treated mice suffered weight loss (~6% at Day 2) initially but the weights recovered by the end of the 14-day monitoring period. The TP20 mice also suffered weight loss, albeit at a reduced level and at a later time point (~4% at Day 7). Two-way ANOVA analysis of the body weight data shows that the difference in body weights between placebo and TP20 treated mice is not significant (p=0.2341). Hence, overall conclusion, TP20/TPX is well tolerated with no safety issues/concerns.

(2) Phase 2 Analysis (Efficacy Study)

Effect of TP20 on Flu-Infected BALB/c Mice

The effect of TP20 (360 μg/kg, oral gavage, twice daily), either alone or in combination with Tamiflu (10 mg/kg, oral gavage, twice daily) was examined in BALB/c mice infected intra-nasally with a dose 5 times the MLD50 of the A/Puerto Rico/8/1934 (H1N1) influenza A virus and compared with Tamiflu alone. BALB/c mice were split into 4 groups of 19 animals and treated twice daily by oral gavage starting at 2 hr prior to viral challenge. The second dose was administered 4 hr post-viral challenge and continued thereafter, twice daily, 8 hr apart for 5 days post-challenge (6 days treatment). The drug groups are described below:

Group 1: Placebo;
Group 2: Tamiflu, 10 mg/kg/dose;
Group 3: TP20, 360 μg/kg/dose;
Group 4: Tamiflu, 10 mg/kg/dose plus TP20, 360 μg/kg/dose.

While 19 animals were used per treatment group, 3 animals per treatment were used for bronchoalveolar lavage (BALs) on Days 3 and 7 post viral challenge and 3 animals per treatment group were sacrificed on Day 4 for pathological analysis. Hence, in the following statistical analysis of the survival and body weight data, only the 10 animals remaining in each group were used.

Figure 13:
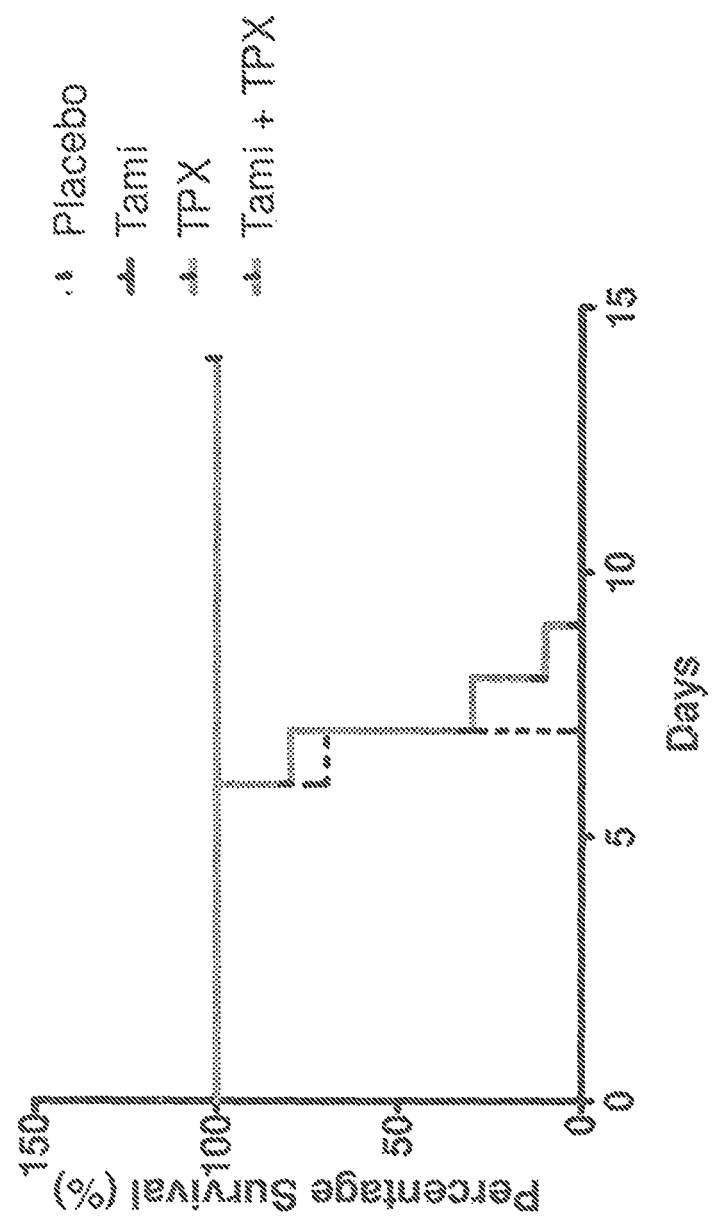
FIG. 13. Effect of TP20 on survival of BABL/c mice infected with 5 MLD50 of the A/Puerto Rico/8/1934 (H1N1) influenza A virus.

(A) Survival Analysis:

Effect of TP20 on Flu-Infected BALB/c mice: Survival Analysis FIG. 13. Effect of TP20 on survival of BABL/c Mice Infected with 5 MLD50 of the A/Puerto Rico/8/1934 (H1N1) influenza A virus. BALB/c mice (7-8 weeks, female), 10 animals per treatment group, were administered Tamiflu (10 mg/kg; blue line), TP20 (TPX; 360 μg/kg; red line), either singly or in combination (green line) or as control, placebo (dashed line) by oral gavage twice daily for 6 days, where the first and second treatment were 2 hr pre- and 4 hr post-viral challenge, respectively. Mice were monitored for 14 days for morbidity. Data is presented as percentage survival as a function of time (Kaplan-Meier survival curve).

Only animals in the groups treated with Tamiflu (10 mg/kg), either alone or in combination with TP20 survived the full duration (14 days) of the study. The placebo and TP20 (360 μg/kg) treated animals died where the mean time of death was 6.7 and 7.2 days post-viral challenge, respectively. Statistical analysis of the complete set of survival data, using the Log-rank (Mantel-Cox) Test, indicates that there is significance between the all 4 of the groups (p<0.0001). Statistical analysis of paired treatment groups are summarized in Table 2.14.

TABLE 2.14

Summary of Statistical Analysis of Paired Treatment Groups

| Paired Group Comparison | Mantel-Cox Test P-Value |
| --- | --- |
| Placebo vs. Tamiflu | p < 0.0001 |
| Placebo vs. TP20 | p = 0.1363 |
| Placebo vs. Tami + TP20 | p < 0.0001 |
| Tami vs. TP20 | p < 0.0001 |
| Tami vs. Tami + TP20 | p = 1 |
| TP20 vs. Tami + TP20 | p < 0.0001 |

The data suggests that there may be a trend toward increased survival for animal treated with TP20 compared to placebo treated animals. More specifically, all of the animals in the Placebo (PBS) group died during Day 6 (n=3) or Day 7 (n=7) while the TP20 treated-mice showed a slower death profile with deaths on Day 6 (n=2), 7 (n=5), 8 (n=2) and Day 9 (n=9). Hence, bearing in mind group size (n=10), while not statistically significant, the TP20 mice showed a tendency toward better survival than the Placebo (PBS) group.

Figure 14A:
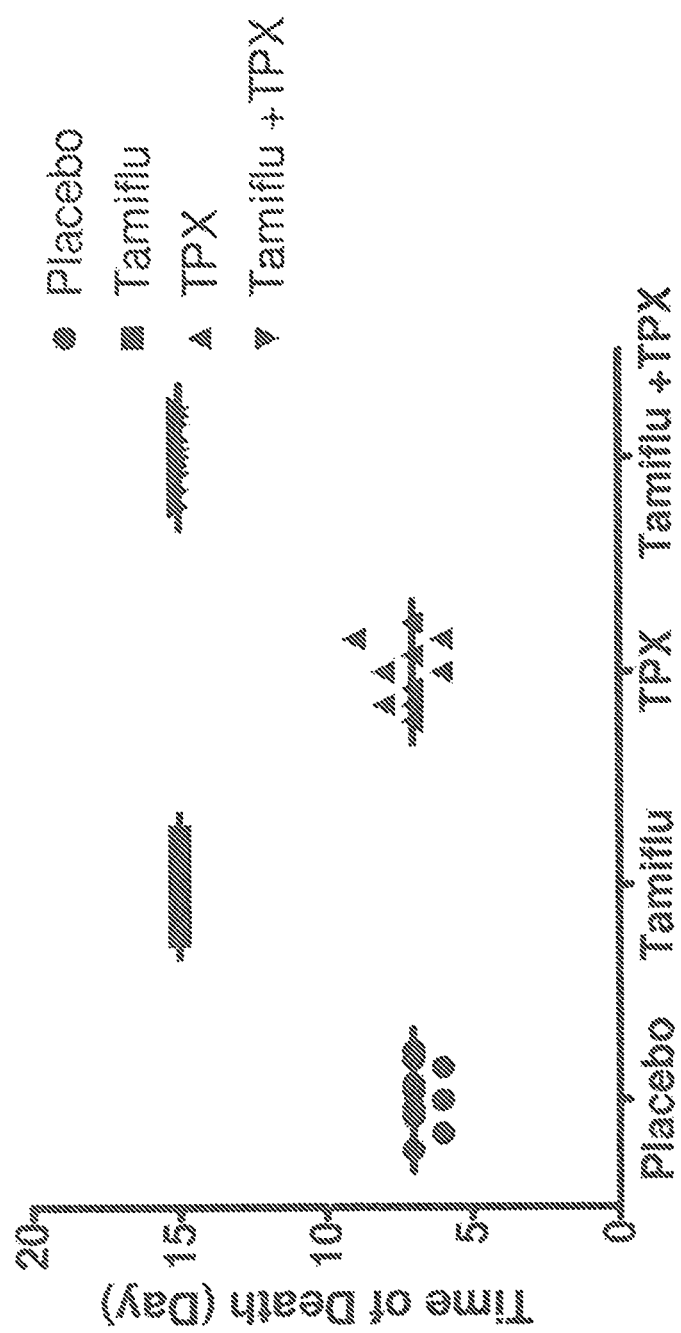
FIGS. 14A and 14B show the effect of TP20 on survival of BABL/c mice infected with 5 MLD50 of the A/Puerto Rico/8/1934 (H1N1) influenza A virus.
Figure 14B:

FIGS. 14A and 14B show the effect of TP20 on survival of BABL/c Mice Infected with 5 MLD50 of the A/Puerto Rico/8/1934 (H1N1) influenza A virus. BALB/c mice (7-8 weeks, female), 10 animals per treatment group, were administered Tamiflu (10 mg/kg), TP20 (TPX; 360 μg/kg), either singly or in combination or as control, placebo by oral gavage twice daily for 6 days, where the first and second treatment were 4 hr pre- and post-viral challenge, respectively. Mice were monitored for 14 days for morbidity. Data is presented as Time to Death (Days) after viral infection as a function of drug treatment.

Figure 15A:
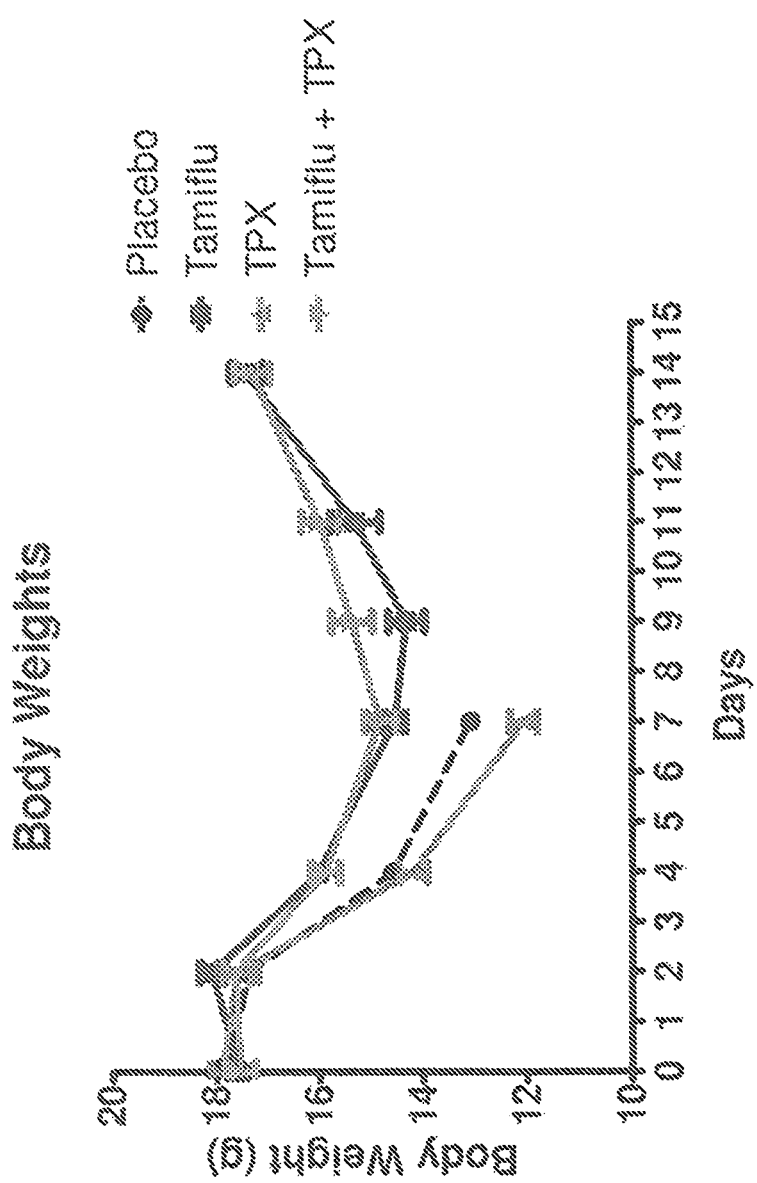
FIGS. 15A and 15B show the effect of TP20 on body weight of BABL/c mice.
Figure 15B:
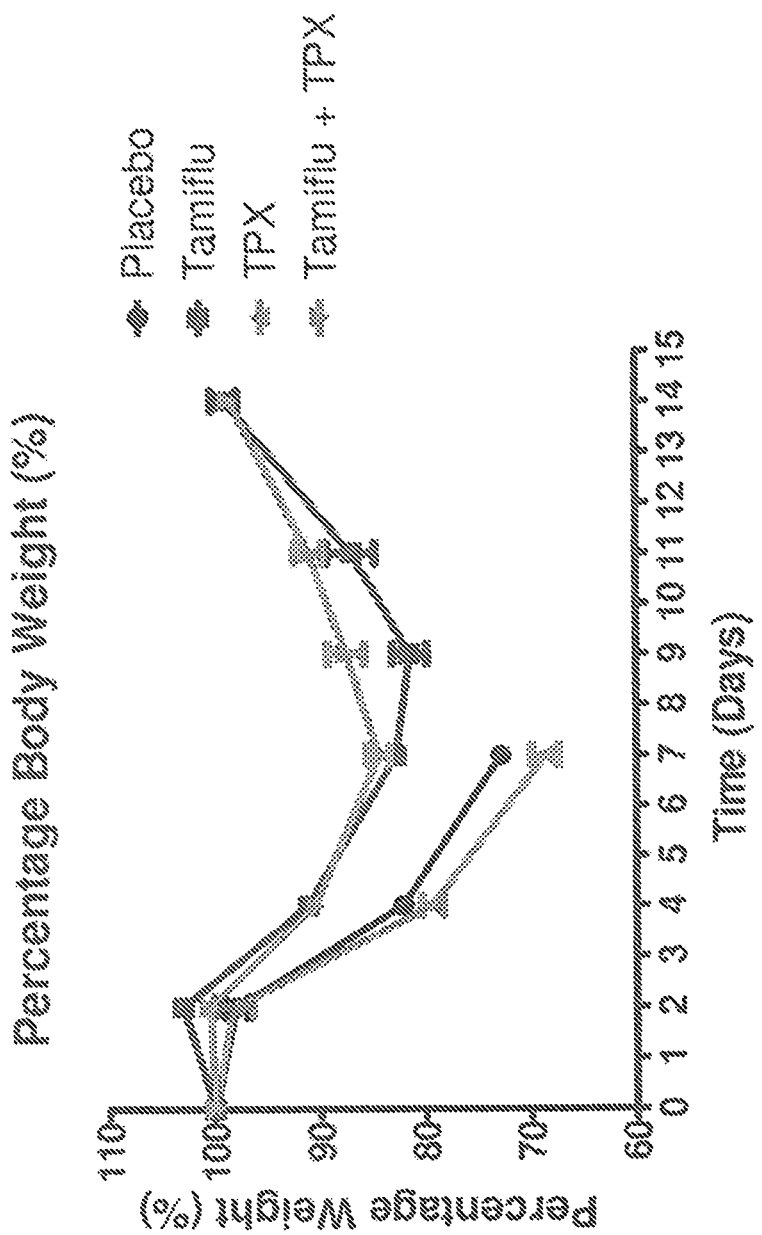

FIG. 14A shows all groups. FIG. 14B shows placebo & TP20 groups only (B) Body Weight Analysis Effect of TP20 on Flu-Infected BALB/c Mice: Body Weight Analysis FIGS. 15A and 15B show the effect of TP20 on Body Weight of BABL/c Mice. BALB/c mice (7-8 weeks, female), 10 animals per treatment group, were administered placebo, Tamiflu (10 mg/kg), TP20 (TPX; 360 μg/kg) and Tamiflu+TP20 (Tamiflu+TPX; 10 mg/kg and 360 μg/kg, respectively) by oral gavage twice daily (100 μl dosing volume), for 6 days. Mice were monitored for 14 days and weighed on Days 0, 2, 4, 7, 9, 11 and 14. Data is presented as mean body weight (±S.E.M.; FIG. 15A) or as mean percentage of body weight (±S.E.M.; FIG. 15B), calculated from the percentage of body weight of each individual mouse relative to the weight at Day 0, which was set at 100%, as a function of time.

The Percentage in body weight was calculated for each individual mouse, where the weight at Day 0 is 100% and the weight for each mouse on Days 2, 4, 7, 9, 11 & 14 are expressed as a percentage of their weight at Day 0. The means and S.E.M. were calculated from those values.

Figure 16A:
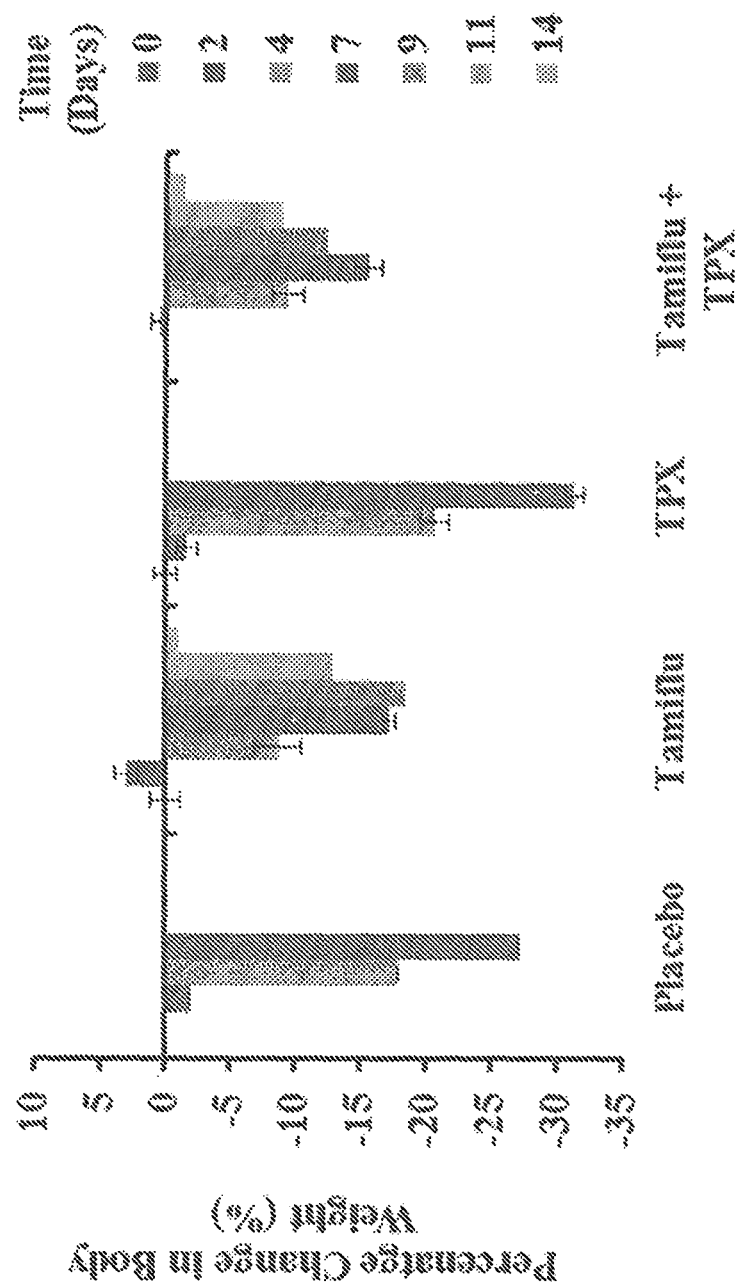
FIGS. 16A and 16B show the effect of TP20 on body weight of BABL/c mice.
Figure 16B:
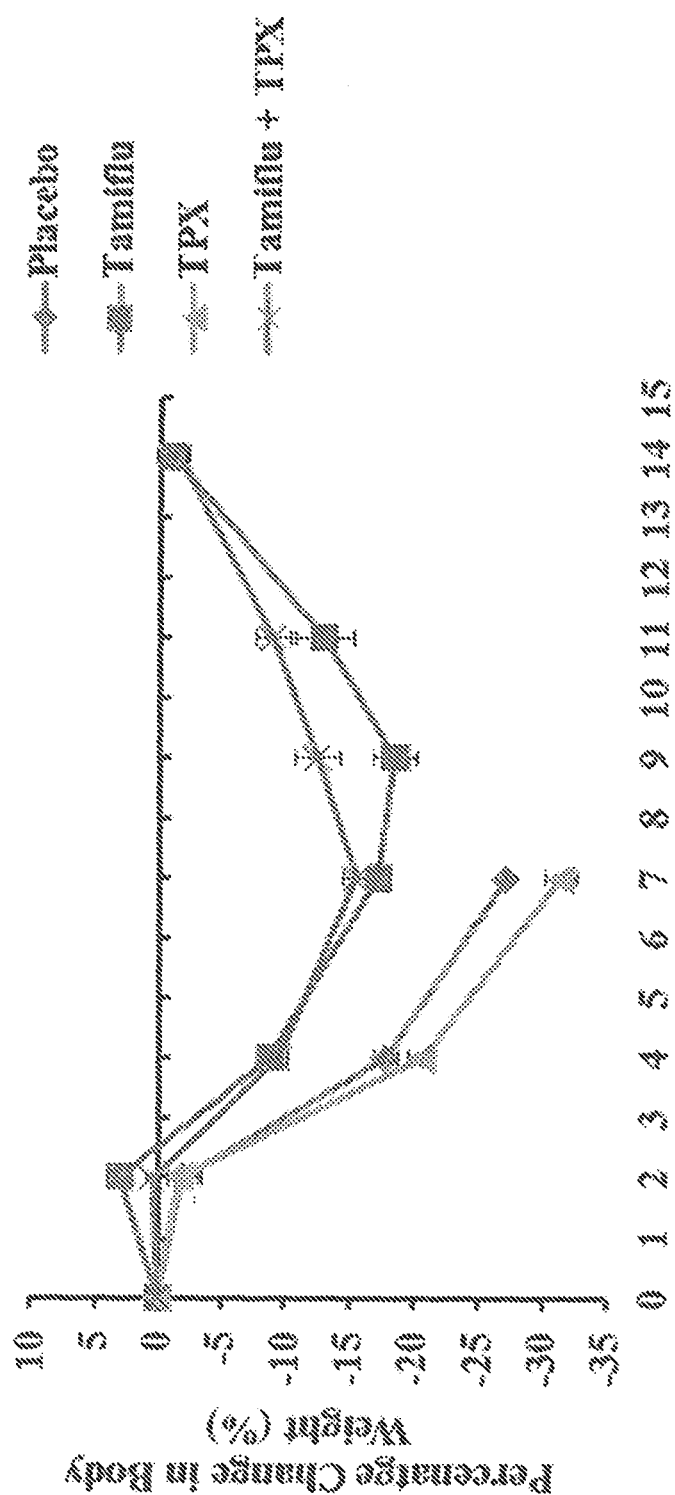

FIGS. 16A and 16B show the effect of TP20 on Body Weight of BABL/c Mice. BALB/c mice (7-8 weeks, female), 10 animals per treatment group, were administered placebo, Tamiflu (10 mg/kg), TP20 (TPX; 360 µg/kg) and Tamiflu+TP20 (Tamiflu+TPX; 10 mg/kg & 360 µg/kg, respectively) by oral gavage twice daily (100 µl dosing volume), for 6 days. Mice were monitored for 14 days and weighed on Days 0, 2, 4, 7, 9, 11 and 14. Data is presented as mean percentage change in body weight (±S.E.M.) over time for each treatment group where the percentage change was calculated as the percentage difference in body weight of each mouse from their weight at Day 0, which was set at 0%, either as a bar chart (FIG. 16A) or as a line graph (FIG. 16B).

During the initial phase post-viral infection (e.g., Days 1-7), all mice in the study lost weight, where the placebo and TP20 treated mice lost as much as 30% body weight. Those animals treated with Tamiflu, either alone or in combination with TP20 (360 µg/kg), exhibited a loss of up to 20% body weight, with weight gain (recovery) observed after 7-9 days. Note that the weight loss is much greater in the animal groups in Phase 2 study compared to those the Phase 1 (Safety) study due to the viral infection.

Given the deaths of the animals in the placebo and TP20-treated groups, statistical analysis by 2-way ANOVA for a comparison of all the treatment groups for days 0-14 was not permitted. Therefore, two-way ANOVA, with Bonferroni post-hoc tests, was performed on:

(1) All groups, where weight from Days 0, 2, & 4 were included in the analysis.

(2) The treatment groups were paired, where weights from Days 0, 2, 4 and, where permitted (Groups 2 & 4), from Days 0, 2, 4, 7, 9, 11 & 14 were included in two-way ANOVA analysis, as indicated.

(1) Two-way ANOVA of the body weights from the 4 treatments groups on days 0, 2 & 4 indicates that there is no significant difference in the weight between the drug treatment groups (p=0.107). The Bonferroni post-hoc tests indicated that at Day 4, the weights were significantly different between:

| | |
|---|---|
| (i) Placebo vs. Tamiflu | p < 0.001; |
| (ii) Placebo vs. Tamiflu + TP20 | p < 0.001; |
| (iii) Tamiflu vs. TP20 | p < 0.001; |
| (iv) TP20 vs. Tamiflu + TP20 | p < 0.001. |

There was no significant difference in weights at 0 or 2 Days. There was no significant difference between Placebo vs. TP20 (p>0.05) and between Tamiflu vs. Tamiflu+TP20 (p>0.05) at either Day 0, 2 or 4.

(2) Two-way ANOVA analysis with Bonferroni post-hoc tests, were performed between pairs of treatment groups were the results are summarized in Table 2.15.

TABLE 2.15

Summary of Two-Way ANOVA Analysis of Body Weights in Paired Treatment Groups.

| Paired Group | Weights Data Included (Days) | Two-Way ANOVA p-value | Bonferroni post-hoc test results |
|---|---|---|---|
| Placebo vs. Tamiflu | 0, 2 & 4 | 0.0116 | Day 2, p < 0.05 Day 4, p > 0.001 |
| Placebo vs. TP20 | 0, 2 & 4 | 0.9736 | No significance indicated in body weights at any time point, p < 0.05 |
| Placebo vs. Tamiflu + TP20 | 0, 2 & 4 | 0.1660 | Day 4, p > 0.001 |
| Tamiflu vs. TP20 | 0, 2 & 4 | 0.0550 | Day 4, p > 0.001 |
| Tamiflu vs. Tamiflu + TP20 | 0, 2, 4, 7, 9, 11 & 14 | 0.6311 | No significance indicated in body weights at any time point, p < 0.05 |
| TP20 vs. Tamiflu + TP20 | 0, 2 & 4 | 0.2463 | Day 4, p > 0.001 |

There is no significant difference in the body weights between the placebo (Group 1) and TP20-(Group 3)-treated animals. Hence, TP20 alone does not prevent the weight loss caused by viral infection. Tamiflu alone (Group 2) or Tamiflu with TP20 (Group 4) significantly decreases the weight loss observed 4 days post-viral infection (p<0.001) compared to placebo or indeed TP20 treated animals and recovery in body weight is noticed after ~Day 9. The combination of TP20 and Tamiflu does not significantly decrease the body weight loss compared to Tamiflu alone at any of the time points analyzed. Hence, taken together, TP20 administered at 360 µg/kg, twice daily, does not significantly reduce or increase the changes in body weight, either when used alone compared to Placebo (compare Group 1 vs. Group 3) or in combination with Tamiflu when compared with Tamiflu treatment alone (compare Group 2 vs. Group 4).

Analysis of Recovery:

All of the above is centered on Body weight loss, relative to that on Day 0 (prior to viral administration) and does not take into account RECOVERY of weight. For example, analysis of data in FIGS. 4A and 4B suggests that there is no difference between the Tamiflu group and the Tamiflu+TP20 group in terms of initial weight loss during days 1-7. However, following the initial weight loss, the mice in these two groups start to recover, but at different rates where the Tamiflu+TP20 group appears to recover at Days 9 and 11 at faster rates than the Tamiflu alone group. However, at Day 14, both groups of mice appear to have fully recovered and, hence, there is no difference in the body weights of the animals in the group between Day 0 (before viral infection) and Day 14 (after full recovery from the viral insult). Hence, to capture this and to establish if there is a statistical difference in the recovery (including rates of recovery) between mice in the Tamiflu+TP20 group relative to those in the Tamiflu alone group, it is necessary to take the weights of the animals at the point of minimum weight/maximum weight loss (appears to be Day 9—but on Day 7, it appears that some of the Tamiflu+TP20 group are starting to recover), express this as a 100% and then express animal weights at Days 9, 11 and 14 as a percentage of that at the day of maximum weight loss (e.g., Day 7/9). This will establish if TP20+Tamiflu is statistically inducing better recovery than Tamiflu alone.

Furthermore, to determine if the mice in the Tamiflu+TP20 and in the Tamiflu alone have fully recovered from the viral insult on Day 14, a statistical comparison of the animal body weights at Day 0 (before viral infection) and on Day 14 should be performed.

In order to look at the recovery of the animals from viral infection, the following analyses were performed:

(1) Comparison of the weights at Day 0 and Day 14 in both the Tamiflu and Tamiflu+TP20 animal groups;

(2) Comparison of the Day of Minimum Body Weight was observed during 14-day study in the Tamiflu (Group 2) vs. Tamiflu+TP20 (Group 4) animals;

(3) Comparison of the Rate of Recovery of body weight of the animals in the Tamiflu (Group 2) vs. Tamiflu+TP20 (Group 4) animals; and (4) Point-by-point comparison of body weights between Tamiflu and Tamiflu+TP20 animal groups using T-test analysis.

Unless otherwise stated, statistical analysis involving T-tests was performed using the unpaired or Student's T-test with two-tailed analysis, where significance was indicated by $p<0.05$.

(1) T-Test Analysis of Weights at Day 0 & Day 14 in the Tamiflu and Tamiflu+TP20-Treated Groups T-test analysis of the weights in the Tamiflu (Group 2) & Tamiflu+TP20-(Group 4) treated animals, comparing the weights at Day 0 and Day 14 are summarized in Table 2.16.

TABLE 2.16

Summary of T-Test Analysis of Body Weights at Day 0 and Day 14 in the Tamiflu & Tamiflu + TP20-Treated Groups.

| Treatment Group | Weight @ Day 0 | Weight @ Day 14 | Paired T-Test, P-Value | Unpaired T-Test, P-Value |
|---|---|---|---|---|
| Tamiflu | 17.56 ± 0.18 | 17.4 ± 0.32 | 0.4840 | 0.6652 |
| Tamiflu + TP20 | 17.55 ± 0.30 | 17.3 ± 0.33 | 0.0422 | 0.5778 | n = 10/group

Paired T-test analysis, where data for each mouse is matched, shows that while there is no significant difference between the weights at Day 0 and Day 14 in the Tamiflu-treated group of mice, the weights of the Tamiflu+TP20 treated mice at Day 14 is slightly less than at Day 0 (p=0.0422). Unpaired T-test analysis, where data is compared as groups, shows that there is no significant difference between the weights at Day 0 and Day 14 in the Tamiflu-treated group of mice (p=0.6652), or in the Tamiflu+TP20-treated mice (p=0.5778). In other words/in conclusion, at day 14, both Groups 2 and 4 had fully recovered their mean weight after flu virus-infection.

(2) T-test analysis of Time/Day to Minimum Body Weight Post-viral Infection.

In order to examine Recovery in the Tamiflu (Group 2) and Tamiflu+TP20 (Group 4)-treated animals, it was initially necessary to determine the day of Minimum Body Weight for each animal in Groups 2 and 4. For this, the 10 animals in each group were used (excluding those animal sacrificed for BALs and Pathology at days 3, 4 & 7) and data is summarized in Table 2.17 including the T-test analyses. T-test analysis shows that there is significant difference in the time/day of minimum body weight and Mean Day to Recovery between the 2 treatment groups. Specifically, animals in Group 2 recovered between Day 7 (n=3) and Day 9 (n=7), with a Mean Day to Recovery of 8.4±0.31 days (days±SEM; n=10). Animals in Group 4 recovered between Day 7 (n=8) and Day 9 (n=2), with a Mean Day to Recovery of 7.4±0.267 days (days±SEM; n=10). Hence, there was a significant difference in the Day to Recovery between the 2 groups of mice, with the Group 4 (TP20+Tamiflu) mice recovering 24 hr faster than the Group 2 (Tamiflu only) mice, where p=−0.024, using the unpaired T-test.

TABLE 2.17

Summary of Day of Minimum Body Weight Recorded

| Animal | Tamiflu | Tamiflu + TP20 | Tamiflu + TP20 |
|---|---|---|---|
| 1 | 9 | 8* | 9 |
| 2 | 9 | 8* | 9 |
| 3 | 9 | 7 | 7 |
| 4 | 7 | 7 | 7 |
| 5 | 9 | 7 | 7 |
| 6 | 9 | 7 | 7 |
| 7 | 9 | 7 | 7 |
| 8 | 7 | 7 | 7 |
| 9 | 9 | 7 | 7 |
| 10 | 7 | 7 | 7 |
| Mean | 8.4 | 7.2 | 7.4 |
| S.E.M. | 0.31 | 0.13 | 0.267 |
| P (Unpaired) | | 0.002 | 0.0239 |

Note, that in Group 4, for two mice the same weights were observed on days 7 & 9 which were also the minimum weight.
Note, that if the numbers for these two mice are retained at 7, it is not possible to do T-tests as all the figures in that group would be the same with no variation. Hence, for analysis, the average was taken and tested, i.e., day 8 for both mice and the significance is p = 0.002 if both data points are changed to 8. However, even if both values were changed to 9, the p value is still significant (p = 0.0239).

Hence, in conclusion, TP20 when used with Tamiflu (Group 4) shows a definite improvement in the actual recovery relative Tamiflu (Group 2) alone using the T-test. Specifically, animals in Group 2 showed a Mean Day to Recovery of 8.4±0.31 days (n=10) and in Group 4 a Mean Day to Recovery of 7.4±0.266 days (n=10). Hence, there was a significant difference in the Day to Recovery between the 2 groups of mice, with the Group 4 (TP20+Tamiflu) mice recovering 24 hr faster than the Group 2 (Tamiflu only) mice where p=0.024.

(3) Linear Regression Analysis of the Rate of Recovery

The rate of increase in body weight data for each mouse after maximum weight loss, i.e., body weight from day 9 to day 14 for the Tamiflu (Group 2) and Tamiflu+TP20 (Group 4)-treated animals was compared by linear regression analysis using GraphPad Prism. The statistical analysis shows that the Rate of Recovery in body weight between the treatment groups is not statistically significant (p=0.1181). In conclusion, the fact that there isn't a difference in the RATE of Recovery is not surprising given that there are only a few measurements of body weights available for the Recovery Phase (day 9, 11 and 14) post-viral infection.

(4) T-Test Analysis of Body Weights Comparing Tamiflu and Tamiflu+TP20 Treated Mice.

The body weights for the Tamiflu (Group 2) and Tamiflu+TP20 (Group 4) animals were compared for each day using T-test analysis. The results are summarized in Table 2.18

TABLE 2.18

Summary of T-Test Analysis of Body Weights by Day between Tamiflu & Tamiflu + TP20 Treatment Groups

| Day | Two-Tailed T-Test | One-Tailed T-Test |
|---|---|---|
| 0 | 0.9771 | 0.4886 |
| 2 | 0.2270 | 0.1135 |
| 4 | 0.7037 | 0.3518 |
| 7 | 0.4456 | 0.2228 |
| 9 | 0.0602 | 0.0301 |
| 11 | 0.2693 | 0.1347 |
| 14 | 0.8291 | 0.4145 |

The t-test analysis indicates that only the body weights on Day 9 differ significantly between the Tamiflu and Tamiflu+TP20 treatment mice is greater than the Tamiflu mice (p=0.03, one tailed t-test).

In conclusion and taken together, Tamiflu+TP20 (Group 4) mice start to recover their body weight some 24 hr prior to animals treated with Tamiflu alone (Group 2) where Mean Day to Recovery=7.4±0.267 for Group 4 compared to Mean=8.4±0.31 for Group 2 (p=0.024) and animals in Group 4 have significantly greater body weight at Day 9 (p=0.0301, one-tailed T-test) relative to those in Group 3. However, the available measurements are not sufficient to support improvements in the Rate of recovery of mice in Group 4 relative to Group 2 per se. This is not surprising given the few available body weight measurements available for the recovery phase of the study (day 9, 11 and 14)—where the mice in both Groups 2 and 4 had fully recovered by day 14.

(D) Histopathology

In an attempt to quantify some of the changes observed in the lungs harvested on Day 4 post viral infection from 3 animals per treatment group (Groups 1-4), Image J was used to quantify perivascular edema. In brief, perivascular edema is used as a measure of the extent of inflammation. Specifically, the extent of perivascular edema or fluid accumulation surrounding the blood vessels in the lungs was quantified in the H&E stained lung sections and, as stated, is used as a measure reflective of the extent of inflammation.

To this end, Imagescope was used to capture multiple (11-15 images per lung) 4× mag images of the scanned in H&E slides for each of the animals or lung tissue. Image J was then used to quantify the perivascular edema in each image, to estimate the extent of perivascular edema. Measurements were taken in four directions and the average obtained for each instance of perivascular edema for each image. Statistical analysis (t-test) was performed to compare differences between the treatment groups.

BABL/c mice were treated twice-daily by oral gavage with Tamiflu (10 mg/kg/dose) or TP20 (0.36 mg/kg/dose), either alone or in combination, as indicated, initiated 2 hr before Influenza A/Puerto Rico/8/1934 H1N1 inoculation (5 MLD50 units) and continued for 5 days. Three animals per treatment group were harvested at Day 4, post-viral infection when lungs were harvested, fixed and processed for histopathology. H&E stained slides were scanned using the Aperio slide scanner and Imagescope was used to capture multiple 4× magnification images of each pair of lungs which were then analyzed using Image J to quantify perivascular edema. Data represents the mean (±S.E.M.; AU, arbitrary units) extent of perivascular edema as a function of treatment group. Asterisks indicate that the TP20 or the combined treatment of TP20 & Tamiflu significantly reduces the extent of perivascular edema, where ***, p<0.001.

FIG. 18 shows the effect of TP20 on Perivascular Edema in Influenza A/Puerto Rico/8/1934 H1N1 Infected Mice. BABL/c mice were treated twice-daily by oral gavage with Tamiflu (10 mg/kg/dose) or TP20 (0.36 mg/kg/dose), either alone or in combination, as indicated, initiated 2 hr before Influenza A/Puerto Rico/8/1934 H1N1 inoculation (5 MLD50 units) and continued for 5 days. Three animals per treatment group were harvested at Day 4, post-viral infection when lungs were harvested, fixed and processed for histopathology. H&E stained slides were scanned using the Aperio slide scanner, where the images below are representative images of lung tissue, captured at 10× magnification, from each of the mice indicating the extent of perivascular edema (black arrows). The horizontal scale bar in the top, left-hand image corresponds to 300 µM.

In conclusion, perivascular edema in the lungs is associated with acute and chronic inflammation, where the space around the capillaries of the lungs becomes infiltrated with fluids and inflammatory cells such as neutrophils. In the lungs of the Influenza A/Puerto Rico/8/1934 H1N1-infected mice, there is evidence of acute inflammation, including perivascular edema. The extent of inflammation in the

TABLE 2.19

Summary of Perivascular Edema in Viral-Infected Mice Treated with Vehicle, Tamiflu and/or TP20.

| Treatment Group | Animal # | Extent of Perivascular Edema (Mean ± S.E.M.; arbitrary units)* | | T-Test Analysis | | |
|---|---|---|---|---|---|---|
| | | Per Animal | Per Treatment Group | P value, vs. Vehicle | P value, vs. Tamiflu | P value, vs. TP20 |
| Vehicle | 2 | 21.9 ± 1.54 (82) | 22.1 ± 0.95 | N/A | — | — |
| | 7 | 22.8 ± 1.43 (64) | | | | |
| | 16 | 19.5 ± 1.32 (67) | | | | |
| Tamiflu (10 mg/kg) | 21 | 21.2 ± 1.71 (52) | 20.6 ± 0.90 | 0.2793 | N/A | — |
| | 27 | 20.7 ± 1.21 (66) | | | | |
| | 35 | 19.3 ± 1.24 (77) | | | | |
| TP20 (0.36 mg/kg) | 40 | 16.9 ± 1.09 (70) | 18.0 ± 0.59 | p = 0.0003 | p = 0.0146 | N/A |
| | 45 | 17.4 ± 0.98 (89) | | | | |
| | 54 | 19.2 ± 1.10 (78) | | | | |
| TP20 + Tamiflu | 59 | 17.6 ± 1.58 (71) | 15.2 ± 0.70 | p < 0.0001 | p < 0.0001 | p = 0.0021 |
| | 64 | 16.2 ± 1.36 (70) | | | | |
| | 73 | 12.0 ± 0.88 (68) | | | | |

*Note: Numbers in brackets indicate the number of blood vessels with measured perivascular edema in the 12 images captured per animal lungs.

Figure 17:
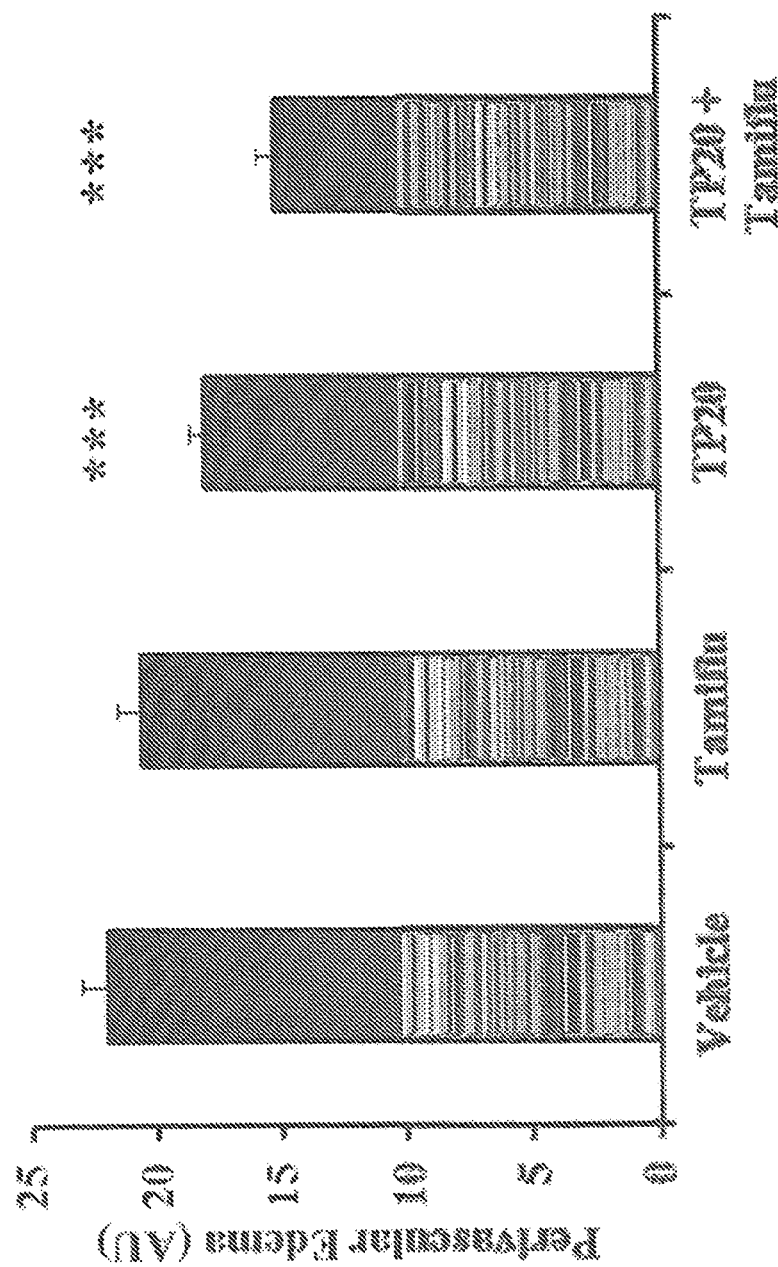
FIG. 17 shows the effect of TP20 on Perivascular Edema in Influenza A/Puerto Rico/8/1934 H1N1 Infected Mice.

FIG. 17 shows the effect of TP20 on Perivascular Edema in Influenza A/Puerto Rico/8/1934 H1N1 Infected Mice. different treatments groups was made by quantifying the extent of perivascular edema.

Quantification and subsequent statistical analysis indicates that Tamiflu alone does not reduce the extent of perivascular edema in the flu-infected mice (p=0.2793). However, when viral-infected mice are treated with TP20, either on its own or in combination with Tamiflu, there is approx. 20 or 30% reduction in the edema compared to vehicle (p=0.0003 and p<0.0001, respectively). Furthermore, there is significantly less perivascular edema in the combined treatment of TP20 and Tamiflu compared to Tamiflu alone (p<0.0001) or TP20 alone (p=0.0021). Taken together, in conclusion, the data supports TP20 as an anti-inflammatory agent that when used alone or in combination with Tamiflu reduces at least one of the signs of acute inflammation, i.e., perivascular edema.

What is claimed is:

1. A method of treating breast or lung cancer, the method comprising administering an anticancer compound represented by a formula selected from the group consisting of (IV), (VI), (VII), (IX), and (X):

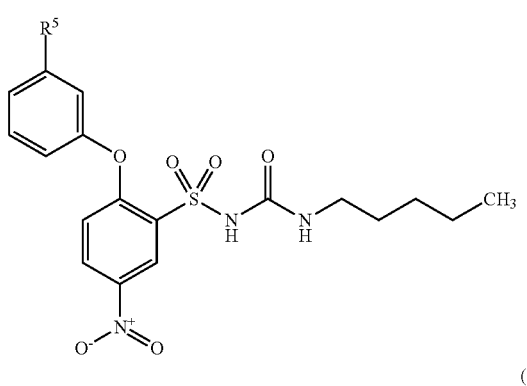
(IV)

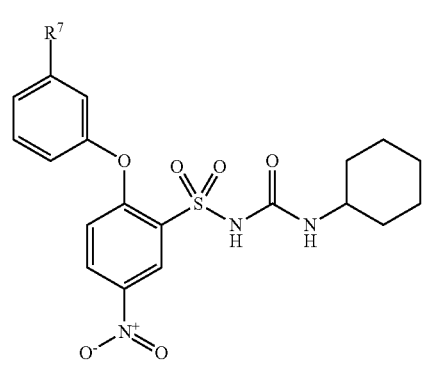
(VI)

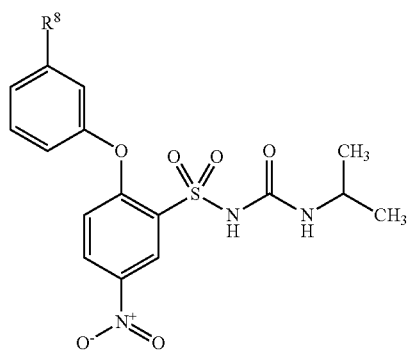
(VII)

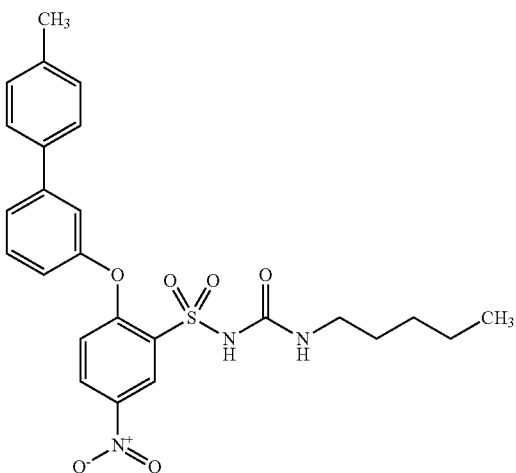
(IX)

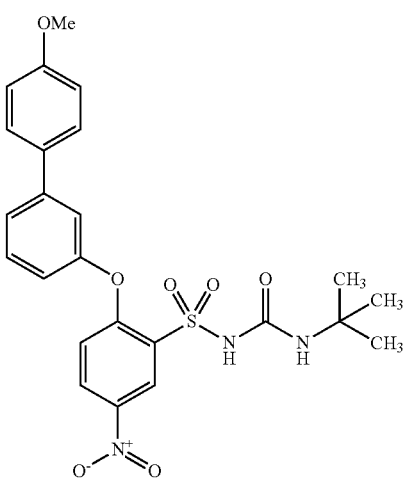
(X)

wherein $R^5$ is

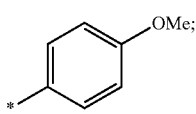

wherein $R^7$ is selected from the group consisting of

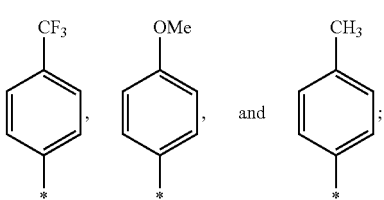

wherein R⁸ is selected from the group consisting of

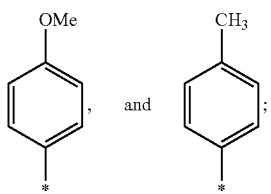

or a pharmaceutically acceptable salt thereof.

2. A method of treating breast or lung cancer, the method comprising administering an anticancer compound of formula (XII):

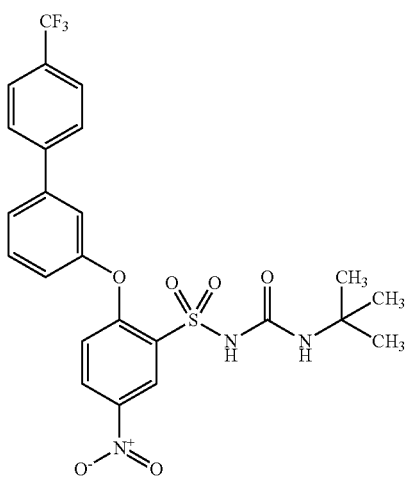

(XII)

or a pharmaceutically acceptable salt thereof.

3. A method of treating breast or lung cancer, the method comprising administering an anticancer compound of formula (XIII):

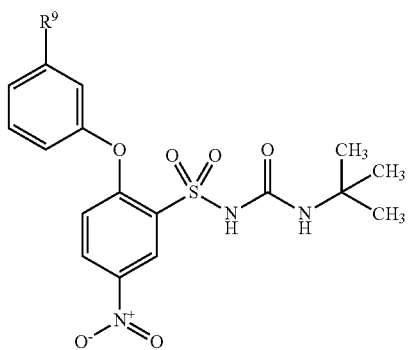

(XIII)

wherein R⁹ is selected from the group consisting of

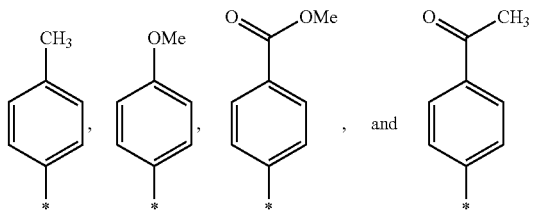

or a pharmaceutically acceptable salt thereof.

4. A method as in any one of the preceding claims, wherein the anticancer compound or the salt thereof binds preferentially to a thromboxane receptor and has preferential binding for either TP-alpha or TP-beta receptor subtype.

* * * * *